US008198428B2

(12) United States Patent
Tuschl et al.

(10) Patent No.: US 8,198,428 B2
(45) Date of Patent: Jun. 12, 2012

(54) IDENTIFICATION OF NOVEL GENES CODING FOR SMALL TEMPORAL RNAS

(75) Inventors: Thomas Tuschl, New York, NY (US); Mariana Lagos-Quintana, New York, NY (US); Winfried Lendeckel, Hohengandern (DE); Jutta Meyer, Bispingen (DE); Reinhard Rauhut, Goettingen (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 12/775,952

(22) Filed: May 7, 2010

(65) Prior Publication Data

US 2010/0286246 A1    Nov. 11, 2010

Related U.S. Application Data

(62) Division of application No. 11/747,409, filed on May 11, 2007, now Pat. No. 7,723,510, which is a division of application No. 10/490,955, filed as application No. PCT/EP2002/010881 on Sep. 27, 2002, now Pat. No. 7,232,806.

(30) Foreign Application Priority Data

Sep. 28, 2001 (EP) .................. 01123453
Mar. 22, 2002 (EP) .................. 02006712
Jul. 26, 2002 (EP) .................. 02016772

(51) Int. Cl.
*C07H 21/04* (2006.01)
*C07H 21/02* (2006.01)
*C12N 15/63* (2006.01)

(52) U.S. Cl. ............. 536/24.5; 536/23.1; 536/24.3; 536/24.31; 536/24.33; 435/320.1

(58) Field of Classification Search .................. None
See application file for complete search history.

(56) References Cited

U.S. PATENT DOCUMENTS

| | | | |
|---|---|---|---|
| 5,801,154 A | 9/1998 | Baracchini et al. | |
| 5,861,310 A | 1/1999 | Freeman et al. | |
| 6,506,559 B1 | 1/2003 | Driver et al. | |
| 6,821,724 B1 | 11/2004 | Mittman et al. | |
| 6,905,827 B2 | 6/2005 | Wohlgemuth et al. | |

OTHER PUBLICATIONS

Ambros V: "microRNAs: Tiny Regulators with Great Potential" Cell, Cell Press, Cambridge, NA, US LNKD D0I:10.1016/S0092-8674(01)00616-X, vol. 107, Dec. 28, 2001, pp. 823-826, XP002978397 ISSN: 0092-8674.
Database EMBL [Online] Oct. 20, 2000, "CM1-HT0877-190900-426-b01 HT0877 *Homo sapiens* cDNA, mRNA sequence."
XP002591547 retrieved from EBI accession No. EMBL:BF088470 Database accession No. BF088470 compound.
Database Geneseq [Online] Jun. 26, 2001, "Human cDNA sequence SEQ ID No. 13278." XP002591548 retrieved from EBI accession No. GSN:AAH15188 Database accession No. AAH15188 compound.
Quintana et al., "Identification of Novel Genes Coding for Small Expressed RNAs", Science, vol. 294, Oct. 26, 2001, pp. 853-858.
Lee et al., "An Extensive Class of Small RNAs in *Caenorhabditis elegans*", Science, vol. 294, Oct. 26, 2001, pp. 862-864.
Elbashir et al., "Functional anatomy of siRNAs for mediating efficient RNAi in *Drosophila melanogaster* embryo lystae", The EMBO Journal, vol. 20, No. 23, pp. 6877-6888, 2001.
*Drosophila melanogaster* sequence (P1 DS08416(D52)), complete sequence; retrieved from Database EMBL Accession No. AC 002442 (Mar. 3, 2000).
Krutzfeldt et al, Strategies to determine the biological function of microRNAs, 2006, Nature Genetics, vol. 37, No. 11, pp. 1163-1165.
Cullen, RNAi the natural wayy, 2005, Nature Genetics, vol. 37, No. 11, pp. 1163-1165.
Lee et al., The *C. elegans* Heterochronic Gene lin-4 Encodes Small RNAs with Antisense Complementarity to lin-14, 1993, Cell, vol. 75, pp. 843-854.
Marra et al., AA209594, EST Feb. 18, 1997, see search results labeled "20090122_121332_US-11-747-409-88.rst", result #3 in SCOPE (enclosed in office action).
Pasquinelli et al., "Conservation of the sequence and temporal expression of let-7 heterochronic regulatory RNA", Nature, vol. 408, No. 6808, 2000, pp. 86-89.
Reinhart et al., "The 21-nucleotide let-7 RNA regulates developmental timing in *Caenorhabditis elegans*", Nature, vol. 403, No. 6772, Feb. 24, 2000, pp. 901-906.
Moss et al., "The cold shock domain protien LIN-28 controls developmental timing in *C. elegans* is rgulated by the lin-4 RNA", Cell, vol. 88, No. 5, 1997, pp. 637-646.
Database.Geneseq [Online] Dec. 15, 1982, "Partial RNA sequence corresponding to cattle pre-somatotropin.", XP002659796, retrieved from EBI accession No. GSN:AAN20038 Database accession No. AAN20038.
Database Geneseq [Online] Jan. 25, 2001, "Mouse glycosyl sulfotransferase-6 (GST-6) genomic DNA.", XP002659797, retrieved from EBI accession No. GSN:AAD02705 Database accession No. AAD02705. Database Geneseq [Online] Aug. 2, 2001, "Human cardiovascular system antigen genomic DNA SEQ ID No. 2411.", XP002659798, retrieved from EBI accession No. GSN:AAS36911 Database accession No. AAS36911.
Database Geneseq [Online] Feb. 7, 2002, "Mouse spliced transcript detection oligonucleotide SEQ ID No. 24151.", XP002659630, retrieved from EBI accession No. GSN:ABN51403 Database accession No. ABN51403.

(Continued)

*Primary Examiner* — Amy Bowman
(74) *Attorney, Agent, or Firm* — Rothwell, Figg, Ernst & Manbeck, P.C.

(57) ABSTRACT

In *Caenorhabditis elegans*, lin-4 and let-7 enclode 22- and 21-nucleotide RNAs, respectively, that function as key regulators of developmental timing. Because the appearance of these short RNAs is regulated during development, they are also referred to as "small temporal RNAs" (stRNAs). We show that many more 21- and 22-nt expressed RNAs, termed microRNAs, (miRNAs), exist in invertebrates and vertebrates, and that some of these novel RNAs, similar to let-7 stRAN, are also highly conserved. This suggests that sequence-specific post-transcriptional regulatory mechanisms mediated by small RNAs are more general than previously appreciated.

24 Claims, 59 Drawing Sheets

OTHER PUBLICATIONS

Figure 1A:
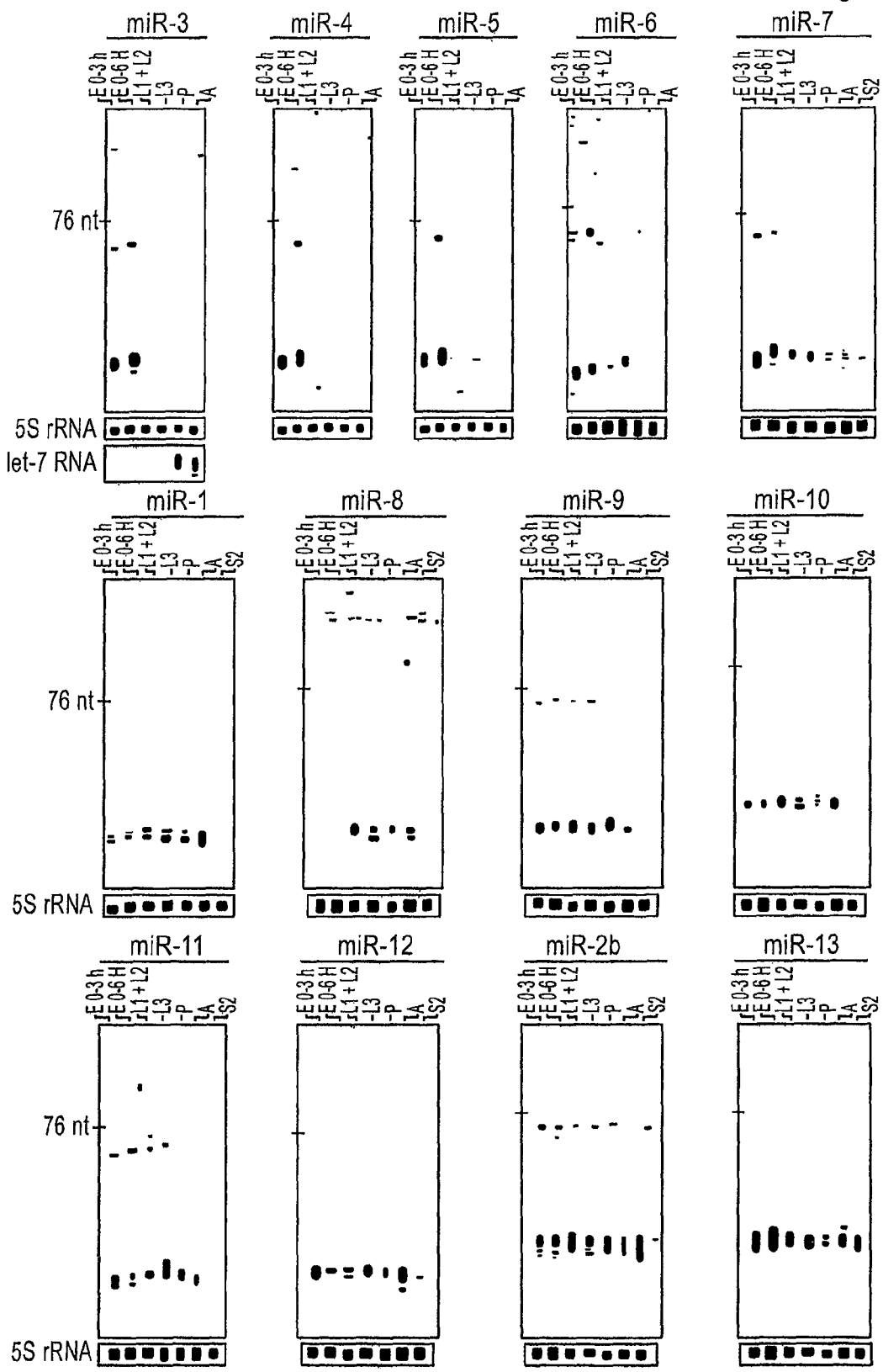

Database Geneseq [Online] Aug. 9, 2001, "Human immune/haematopoietic antigen encoding cDNA SEQ ID No. 9362.", XP002659777, retrieved from EBI accession No. GSN:AAK64302 Database accession No. AAK64302.

Database Geneseq [Online] Oct. 23, 1997, "*Streptococcus pneumoniae* leucyl tRNA synthetase gene.", ../ XP002659778, retrieved from EBI accession No. GSN:AAT88991 Database accession No. AAT88991.

Database Geneseq [Online] Jul. 5, 2001, "Human SNP oligonucleotide #288.", XP002659790, retrieved from EBI accession No. GSN:AAL27080 Database accession No. AAL27080.

Database Geneseq [Online] Aug. 9, 2001, "Human immune/haematopoietic antigen genomic sequence SEQ ID No. 22901.", XP002659791, retrieved from EBI accession No. GSN:AAK68089 Database accession No. AAK68089.

Database Geneseq [Online] Oct. 28, 1999, "*D. pteronyssius* 98 kD mite allergen gene nDerp98-1470 complement.", XP002659792, retrieved from EBI accession No. GSN:AAZ38590 Database accession No. AAZ38590.

Database Geneseq [Online] Aug. 16, 2001, "Human 6-finger VEGF3a/1 DNA constructing oligonucleotide.", XP002659780, retrieved from EBI accession No. GSN:AAD15343 Database accession No. AAD15343.

Database Geneseq [Online] Sep. 27, 2001, "*Drosophila melanogaster* expressed polynucleotide SEQ ID No. 4649.", XP002659781, retrieved from EBI accession No. GSN:ABL03389 Database accession No. ABL03389.

Database Geneseq [Online] Oct. 19, 1995, "Amplification primer BK83.", XP002659793, retrieved from EBI accession No. GSN:AAT08183 Database accession No. AAT08183.

Database Geneseq [Online] Sep. 30, 1999, "Tobacco plant resistance-associated cDNA fragment 81.", XP002659794, retrieved from EBI accession No. GSN:AAZ33756 Database accession No. AAZ33756.

Wu et al.: ,,Suppression of cell growth and invasion by rniR-205 in breast cancer, Cell Research, vol. 19, 2009, pp. 439-448.

Iorio et al.: ,,MicroRNA Signatures in Human Ovarian Cancer,Cancer Research, vol. 67, No. 18, 2007, pp. 8699-8707.

Calin et al.: "Frequent deletions and down-regulation of microRNA genes miR15 and miR16 at 13q14 in chronic lymphocytic leukemia", PNAS, vol. 99, No. 24, Nov. 26, 2002, pp. 15524-15529.

Chan et al.: "MicroRNA-21 is an antiapoptotic factor in human glioblastoma cells", Cancer Research, No. 65, vol. 14, Jul. 15, 2005, pp. 6029-6033.

Kulshreshtha et al.: "A MicroRNA Signature of Hypoxia", Molecular and Cellular Biology, No. 27, 2007, pp. 1859-1867.

Van Rooij et al.: "Dysregulation of rnicroRNAs after myocardial infarction reveals a role of rniR-29 in cardiac fibrosis", PNAS, vol. 105, No. 35, Sep. 2, 2008, pp. 13027-13032.

Database Geneseq [Online] Aug. 8, 1996 ,,S. Mutants antigen I/II (aa1024-1044) DNA., retrieved from EBI accession No. GSN:AAT36119, Database accession No. AAT36119.

Database Geneseq [Online] Aug. 2, 2001 ,,Human cardiovascular system antigen genomic DNA SEQ ID No. 1605., retrieved from EBI accession No. GSN:AAS36105, Database accession No. AAS36105.

Database Geneseq [Online] Apr. 19, 2001 "Tobacco rpL34 promoter region.", retrieved from EBI accession No. GSN:AAH19667, Database accession No. AAH19667.

Database Geneseq [Online] Aug. 9, 2001 "Human immune/haernatopoietic antigen genomic sequence SEQ ID No. 34996.", retrieved from EBI accession No. GSN:AAK80184, Database accession No. AAK80184.

Kusenda et al.: ,,MicroRNA Biogenesis, Functionality and Cancer Relevance, Biorned Pap Med Fac Univ Palacky Olomouc Czech Repub., vol. 150, No. 2, 2006, pp. 205-215.

Cheng et al.: ,,Antisense inhibition of human rniRNAs and indications for an involvement of rniRNA in cell growth and apoptosis, Nucleic Acids 2005 Researc1290-1297h, vol. 33, No. 4, pp. 1290-1297.

Wang et al.: ,,Prostate apoptosis response protein 4 sensitizes human colon cancer cel,s to chemotherapeutic 5-FU through mediation of an NFKB and microRNA network, Molecular Cancer, vol. 9, No. 98, 2010, pp. 1-19.

Wahlestedt et al., "Potent and nontoxic antisense oligonucleotides containing locked nucleic acids", PNAS, 2000, vol. 97, No. 10, pp. 5633-5638.

Database Geneseq [Online] Sep. 27, 2001, "Drosophila melanogaster genomic polynucleotide SEQ ID No. 10495.", XP002668047, retrieved from EBI accession No. GSN:ABL19674 Database accession No. ABL19674

Database Geneseq [Online] Sep. 21, 2000, "Human cancer associated gene sequence SEQ ID No:356.", XP002668268, retrieved from EBI accession No. GSN:AAC77962 Database accession No. AAC77962.

Database Geneseq [Online] Aug. 6, 1998, "LM609 antibody light chain variable region DNA fragment.", XP002668049, retrieved from EBI accession No. GSN:AAV49823 Database accession No. AAV49823.

Database Geneseq [Online] Aug. 8, 1996, "S. mutans antigen I/II (aa1024-1044) DNA.", XP002659848, retrieved from EBI accession No. GSN:AAT36119 Database accession No. AAT36119.

Database Geneseq [Online] D, Aug. 2, 2001, "Human cardiovascular system antigen genomic DNA SEQ ID No. 1605.", XP002659849, retrieved from EBI accession No. GSN:AAS36105 Database accession No. AA536105 .

Database Geneseq [Online] Aug. 2, 2001, Human reproductive system related antigen DNA SEQ ID No: 5635. 11,XP002668053,retrieved from EBI accession No. GSN:AAL02947 Database accession No. AAL02947.

Database Geneseq [Online] Feb. 7, 2002, "Human spliced transcript detection oligonucleotide SEQ ID No:5959.", XP002668054,retrieved from EBI accession No. GSN:ABN33211 Database accession No. ABN33211.

Database Geneseq [Online] Sep. 13, 2001, "Novel human)diagnostic and therapeutic gene #2158.", XP002668055, retrieved from EBI accession No. GSN:AAS39100 Database accession No. AAS39100.

Database Geneseq [Online] Aug. 9, 2001, "Probe #3307 used to measure gene expression in human breast sample.", XP002668109, retrieved from EBI accession No. GSN:AAI03316 Database accession No. AA103316.

Database Geneseq [Online] Aug. 9, 2001, "Human brain expressed single exon probe SEQ ID No: 3386.", XP002668176, retrieved from EBI accession No. GSN:AAK03395 Database accession No. AAK03395.

Database Geneseq [Online] Aug. 9, 2001, "Probe #14654 for gene expression analysis in human heart cell sample.", XP002668111, retrieved from EBI accession No. GSN:ABA36188 Database accession No. ABA36188.

Database Geneseq [Online] Aug. 5, 1999, "Human gene expression product cDNA sequence SEQ ID No:1651.", XP002668167, retrieved from EBI accession No. GSN:AAZ14182 Database accession No. AAZ14182.

Database Geneseq [Online] Aug. 5, 1999, "Human gene expression product cDNA sequence SEQ ID No:5028.", XP002668168, retrieved from EBI accession No. GSN:AAZ17555 Database accession No. AAZ17555.

Database Geneseq [Online] May 10, 2001, "Gene expression profile sequence #181.", XP002668169, retrieved from EBI accession No. GSN:AASO4681 Database accession No. AAS04681.

Database Geneseq [Online] Aug. 2, 2001, "Human EST-derived coding sequence SEQ ID No: 908.", XP002668164, retrieved from EBI accession No. GSN:AAH99051 Database accession No. AAH99051.

Database Geneseq [Online] Oct. 11, 2001, "DNA encoding novel human diagnostic protein #4753.", XP002668165, retrieved from EBI accession No. GSN:AAS68949 Database accession No. AAS68949.

Database Geneseq [Online] Jul. 28, 1993, "HIV-1 gag gene branched probe strand 2 forms structure 1.", XP002668166, retrieved from EBI accession No. GSN:AAQ54102 Database accession No. AAQ54102.

Database Geneseq [Online] R 4 Sep. 27, 2001, "Drosophila melanogaster genomic polynucleotide SEQ ID No. 10495.", XP002668047, retrieved from EBI accession No. GSN:ABL19674 Database accession No. ABL19674.

Database Geneseq [Online] 2 Sep. 21, 2000, "Human cancer associated gene sequence SEQ ID No:356.", XP002668268, retrieved from EBI accession No. GSN:AAC77962 Database accession No. AAC77962.

Database Geneseq [Online] R6 Aug. 6, 1998, "LM609 antibody light chain variable region DNA fragment.", XP002668049, retrieved from EBI accession No. GSN:AAV49823 Database accession No. AAV49823.

Database Geneseq [Online] Jul. 15, 2002, "Human spliced transcript detection oligonucleotide SEQ ID No:7641.", XP002671443, retrieved from EBI accession No. GSN:ABN34893 Database accession No. ABN34893.

Database Geneseq [Online] Jun. 24, 2002, "Human ORFX polynucleotide sequence SEQ ID No:19021.", XP002671444, retrieved from EBI accession No. GSN:ABN25272 Database accession No. ABN25272.

Database Geneseq [Online] Feb. 13, 2002, "DNA encoding novel human diagnostic protein #421.", XP002671445, retrieved from EBI accession No. GSN:AAS64617 Database accession No. AAS64617.

A

B

Fig. 4 (cont.)

A

| SEQ ID NO.414 | *C. elegans* lin-4 | UCCCUGAGACCUC--AAG-UGUGA |
| SEQ ID NO.415 | *D. melanogaster* miR-125 | UCCCUGAGACCCU--AACUUGUGA |
| SEQ ID NO.416 | *M. musculus/H. sapiens* miR-125b | UCCCUGAGACCCU--AACUUGUGA |
| SEQ ID NO.417 | *M. musculus/H. sapiens* miR-125a | UCCCUGAGACCCUUUAACCUGUGA |

B

Fig.7

| name | sequence | structure |
|------|----------|-----------|
| let-7a-1 | UGAGGUAGUAGGUUGUAUAGUU SEQ ID NO: 105 | SEQ ID NO: 271 |
| let-7a-2 | UGAGGUAGUAGGUUGUAUAGUU SEQ ID NO: 106 | SEQ ID NO: 272 |
| let-7a-3 | UGAGGUAGUAGGUUGUAUAGUU SEQ ID NO: 106 | SEQ ID NO: 273 |
| let-7b | UGAGGUAGUAGGUUGUGUGGUU SEQ ID NO: 107 | SEQ ID NO: 274 |
| let-7c | UGAGGUAGUAGGUUGUAUGGUU SEQ ID NO: 108 | SEQ ID NO: 275 |
| let-7d | AGAGGUAGUAGGUUGCAUAGU SEQ ID NO: 109 | SEQ ID NO: 276 |
| let-7e | UGAGGUAGGAGGUUGUAUAGUU SEQ ID NO: 110 | SEQ ID NO: 277 |

Fig.7 (cont)

| | | | SEQ ID NO |
|---|---|---|---|
| let-7f-1 | UGAGGUAGUAGAUUGUAUAGUU SEQ ID NO: 111 | (stem-loop structure) | 278 |
| let-7f-2 | UGAGGUAGUAGAUUGUAUAGUU SEQ ID NO: 111 | (stem-loop structure) | 279 |
| let-7g | UGAGGUAGUAGUUUGUACAGUA SEQ ID NO: 112 | (stem-loop structure) | 280 |
| let-7h | UGAGGUAGUAGUCUGUACAGUU SEQ ID NO: 113 | | |
| let-7i | UGAGGUAGUAGUUUGUGCUGUU SEQ ID NO: 114 | (stem-loop structure) | 281 |
| miR-1 | UGGAAUGUAAAGAAGUAUGAG SEQ ID NO: 98 | (stem-loop structure) | 282 |
| miR-1b | UGGAAUGUAAAGAAGUAUGUAA SEQ ID NO: 115 | (stem-loop structure) AL449263.5 | 283 |

Fig.7 (cont)

| | | |
|---|---|---|
| miR-1c | UGGAAUGUAAAGAAGUAUGUAC SEQ ID NO: 116 | GCUUGGGA ACAUAACUCUUUAUAU GC CCAUA UGAACC C<br>CGAACUUU UGUAUGAAGAAAUGUA GGUAU A G<br>A- CGAAUC<br>SEQ ID NO: 284 |
| miR-1d | UGGAAUGUAAAGAAGUAUGUAU SEQ ID NO: 117 | GCUGGCUC UCAAAG UCCUUGGGA A AUUUC UU<br>CGAUUCGAG AGUUUC ACCGAACCCU AGC GCC CGC GGG<br>C G A CG<br>SEQ ID NO: 285 |
| miR-2a-1 | UAUCACAGCCAGCUUUGAUGAGC SEQ ID NO: 59 | A C UG UCAUCAAG UGGUUGUGAUAG GAUAC C<br>AUCU AGC UCUUCAAAG UCCUUCAAAG UGGUUGUGAUAG<br>UAGG UCG AGUUUUC ACCGACACU UAG ACC GCAAC<br>CG A C<br>SEQ ID NO: 286 |
| miR-2b-1 | UAUCACAGCCAGCUUUGAGGAGC SEQ ID NO: 59 | CU CAAC UCUUCAAAG UGGC GUGA C AUGUG C<br>GG GUUG AGGAGUUUC ACCG CACU CAGU A<br>C G A AUACU<br>SEQ ID NO: 287 |
| miR-2b-2 | UAUCACAGCCAGCUUUGAGGAGC SEQ ID NO: 60 | UUGUGUC UCCUUCAAAG UGGUUGUGA ABC U UUU-- GC CUU<br>AGCGCAG AGGAGUUUC ACCGACACU UAC CG CG UAU<br>A G C UAUC<br>SEQ ID NO: 288 |
| miR-3 | UCACUGGGCAAAGUGUGUCUCA SEQ ID NO: 61 | C G U G D UCA<br>GAUC UGGGAUGCAU UUGU CAGU AUGU A<br>CUAG ACUCCGUG AAGG GUCA UACA CUCU<br>A G C<br>SEQ ID NO: 289 |

Fig.7 (cont)

Fig.7 (cont)

| | | |
|---|---|---|
| miR-9 | UCUUUGGUUAUCUAGCUGUAUGA SEQ ID NO: 67 | (structure) SEQ ID NO: 297 |
| miR-10 | ACCCUGUAGAUCCGAAUUUGUG SEQ ID NO: 68 | (structure) SEQ ID NO: 298 |
| miR-11 | CAUCACAGUCUGAGUUCUUGC SEQ ID NO: 69 | (structure) SEQ ID NO: 299 |
| miR-12 | UGAGUAUUACAUCAGGUACUGGU SEQ ID NO: 70 | (structure) SEQ ID NO: 300 |
| miR-13a | UAUCACAGCCAUUUUGACGAGU SEQ ID NO: 71 | (structure) SEQ ID NO: 301 / SEQ ID NO: 302 |
| miR-13b-1 | UAUCACAGCCAUUUUGACGAGU SEQ ID NO: 72 | (structure) SEQ ID NO: 303 |
| miR-13b-2 | UAUCACAGCCAUUUUGACCAGU SEQ ID NO: 72 | |

Fig.7 (cont)

Fig. 7 (cont.)

| | | SEQ ID NO. 311 | SEQ ID NO. 312 | SEQ ID NO. 313 | SEQ ID NO. 314 | SEQ ID NO. 315 | SEQ ID NO. 316 | SEQ ID NO. 317 |
|---|---|---|---|---|---|---|---|---|
| miR-19a | UGUGCAAAUCUAUGCAAAACUGA SEQ ID NO. 85 | (structure) | | | | | | |
| miR-19b-1 | UGUGCAAAUCCAUGCAAAACUGA SEQ ID NO. 86 | | (structure) | | | | | |
| miR-19b-2 | UGUGCAAAUCCAUGCAAAACUGA SEQ ID NO. 86 | | | (structure) | | | | |
| miR-20 | UAAAGUGCUUAUAGUGCAGGUAG SEQ ID NO. 87 | | | | (structure) | | | |
| miR-21 | UAGCUUAUCAGACUGAUGUUGA SEQ ID NO. 88 | | | | | (structure) | | |
| miR-22 | AAGCUGCCAGUUGAAGAACUGU SEQ ID NO. 89 | | | | | | (structure) | |
| miR-23a | AUCACAUUGCCAGGGAUUUCC SEQ ID NO. 127 | | | | | | | (structure) |

Fig.7 (cont.)

Fig. 7 (cont.)

| | | | | | | |
|---|---|---|---|---|---|---|
| miR-27b | miR-28 | miR-29a | miR-29b | miR-29c | miR-30a-5 | miR-30a-as |
| UUCACAGUGGCUAAGUUCUG SEQ ID NO. 133 | AAGGAGCUCACAGUCUAUUGAG SEQ ID NO. 86 | CUAGCACCAUCUGAAAUCGGUU SEQ ID NO. 134 | UAGCACCAUUUGAAAUCAGUGUU SEQ ID NO. 135 | UAGCACCAUUUGAAAUCGGuua SEQ ID NO. 136 | UGUAAACAUCCUCGACUGGAAGC SEQ ID NO. 137 | CUUUCAGUCGGAUGUUUGCAGC SEQ ID NO. 138 |

Fig.7 (cont.)

| | | |
|---|---|---|
| miR-30b | UGUAAACAUCCUACACUCAGC SEQ ID NO: 139 | AUGUAAACAUCC—AGA CUCACUCUG UCAUA C A<br>UGCCAUUUGCAG UGU GGGGUGGCU UCCGU<br>— U A SEQ ID NO: 331 |
| miR-30c | UGUAAACAUCCUACACUCUCAGC SEQ ID NO: 140 | UACU U ACA GUGGAA A C<br>AGA GUAAACA CCU CACUCUCAGCU A<br>UCU CAUUUGU GGA GUGGGAGUCGA G<br>UUCU C A— — AACAAU SEQ ID NO: 332 |
| miR-30d | UGUAAACAUCCCCGACUGGAAG SEQ ID NO: 141 | U U CCC GUAAGA C A<br>GU GGU GUAAACAUC GACUUGGAAGCU<br>CA CG CGUUUGUAG CUGACUUUCGA AUCGAC<br>, A— — chr 8 human SEQ ID NO: 333 |
| miR-31 | GGCAAGAUGCUGGCAUAGCUG SEQ ID NO: 98 | GA G C GAA G<br>GGAGAG GGCAA AUG UGGCAUAGCU GGU U<br>CCUUUC UCGUU UAC ACCGUAUCGA CAA C<br>UA A A— — UC UC GGG SEQ ID NO: 334 |
| miR-32 | UAUUGCACAUUACUAAGUUGC SEQ ID NO: 100 | U UU C<br>CUGGCAUCAUUAU ACUAAGUUGCAU GU C A C<br>GACCGUAGUAACA UGAUUAACGUA CAA G G G<br>U UU — A UU SEQ ID NO: 335 |
| miR-33 | GUGCAUUGUAGUUGCAUUGC SEQ ID NO: 101 | A UU UGCAG UUCU G GG UG A G<br>CUGUGG AGUG UGGCAUGU UG CC C<br>GACACU UCGU ACCGUACG GAACGC GC G<br>C UU — G U — — — AU SEQ ID NO: 336 |
| miR-99a | ACCCGUAGAUCCGAUCUUGU SEQ ID NO: 142 | A UC U G AAG UU<br>CAUA ACCCGUAGA UCC GAUCUUGUG AG CUUGUC UG G<br>GUGU UGGGCAUCU AGG CUAGAACGU UC GAACGC GC G<br>C — — — — — CAG SEQ ID NO: 337 |

Fig.7 (cont.)

| | | | SEQ ID NO: 143 | | SEQ ID NO: 338 |
|---|---|---|---|---|---|
| miR-99b | CACCCGUAGAACCGACCUUGCG | SEQ ID NO: 143 | GGCAC ACCGUAGA AC C CU UGCCG GG C<br>CG ACCGUAGA CGA CU UGCCG GG C<br>CUGUG UGGCUGGCU GCU GA XCGCC CU C<br>CC G C ACAC G U | | SEQ ID NO: 338 |
| miR-101 | UACAGUACUGUGAUAACUGA | SEQ ID NO: 144 | UCAGUUAUCACAGUGCUG UGCC U<br>AGUCAAUAGUGUCACGAC AUGG U<br>A AAAUC | | SEQ ID NO: 339 |
| miR-122a | UGGAGUGUGACAAUGGUGUUUGU | SEQ ID NO: 145 | AGCUACU GG C UGUCC<br>ACCUGU AGUGUGA AAUGGUGUUUG A<br>UGGACA UCACACU UUACACU UAACA<br>XA A | SEQ ID NO: 340 woodchuck |
| miR-122b | UGGAGUGUGACAAUGGUGUUUGA | SEQ ID NO: 146 | | |
| miR-122a,b | UGGAGUGUGACAAUGCUGUUUG | SEQ ID NO: 147 | | |
| miR-123 | CAUUAUUACUUUUGGUACGCG | SEQ ID NO: 148 | UGAC A A UGA A C<br>ACUG GC CAUUAUUACUU UGGUAC CGCUG U<br>G C GUAAUAAUGGG GCCAUG GCGAC ACU C<br>UCAA UAAUC | SEQ ID NO: 341 |
| miR-124a* | UUAAGGCACGCGGUGAAUGCCA | SEQ ID NO: 149 | UAAUG<br>CGUU C GUGUUCAC GCG CCUUGAUU U<br>GAGA C CGUAAGUG CGC GGAAUUAA C<br>A - AC CAUAU | SEQ ID NO: 342 |

Fig.7 (cont.)

| | | | |
|---|---|---|---|
| miR-124b | UUAAGGCACGCGGUGAAUGC SEQ ID NO: 190 | CC A GA CCUUGAUU UAAUG<br>CGCU GGGUUCAC GCG CCUUGAUU U<br>GAGA CGUAAGUG CGC GGAAUUAA CAUAC<br>AC G AC | SEQ ID NO: 343 AC021510 |
| miR-125a | UCCCUGAGACCCUUAACCUGUG potential lin-4 ortholog SEQ ID NO: 191 | C A GG C CC G U<br>CUGGGU CCUGAGA CCUU ACCUGUGA GG C CC G<br>GGUCCG GGACUUU GGAC UGGACACU CC G CCGA<br>A U | SEQ ID NO: 344 |
| miR-125b | UCCCUGAGACCCUAACUUGUGA potential lin-4 ortholog SEQ ID NO: 192 | UC A GG- U UAU U<br>GC CCUGAG CCU ACUUGUGA AUG U<br>CG GGACUCU GGA UGAACACU AUG A<br>CA C ACA A | SEQ ID NO: 345 |
| miR-126 | UCGUACCGUGAGUAAUAAUGC SEQ ID NO: 193 | A U CGCUC C<br>GC CAUUAUUACU UGGUACG UGA A<br>CG GUAAUAAUGAG GCCAUGC ACU U<br>C UCAA- U | SEQ ID NO: 346 |
| miR-127 | UCGGAUCCGUCUGAGCUUGGCU SEQ ID NO: 194 | A U G AG \<br>CC GCC GCU AAGCUCAGA GG UCUUGAU UC A<br>GG UGG CGG UUCGAGUCU CC AGGCCUA AG A<br>C U - CU AA | SEQ ID NO: 347 |
| miR-128 | UCACAGUGAACCGGUCUCUUU SEQ ID NO: 195 | UUC UAC CU U U<br>GUUGGA CACUGCU CAGAGGU CUCUUUA A<br>CGACUU GUGACGA GUCUCCA CGAGAAU C<br>UUUC CAA - | SEQ ID NO: 348 |
| miR-129 | CUUUUUGCGGUCUGGGCUUGC SEQ ID NO: 196 | C C CU G UUCCU CU A<br>GGAU CUUUUUG CGGC GGGCAGU CUG CG A<br>UCCA GAAAAAC GCCG CCCGGCA GAC GA C<br>- C U UGAU- UGAU- GA A | SEQ ID NO: 349 human |

Fig.7 (cont)

| | | |
|---|---|---|
| miR-130 | CAGUGCAAUGUUAAAAGGGC SEQ ID NO: 157 | [stem-loop structure] SEQ ID NO: 350 |
| miR-131 | UAAAGCUAGAUAACCGAAAGU SEQ ID NO: 158 | [stem-loop structure] SEQ ID NO: 351 |
| miR-132 | UAACAGUCUACAGCCAUGGUCGU SEQ ID NO: 159 | [stem-loop structure] SEQ ID NO: 352 |
| miR-133 | UUGGUCCCCUUCAACCAGCUGU SEQ ID NO: 160 | [stem-loop structure] SEQ ID NO: 353 |
| miR-134 | UGUGACUGGUUGACCAGAGGGA SEQ ID NO: 161 | [stem-loop structure] SEQ ID NO: 354 |
| miR-135 | UAUGGCUUUUUAUUCCUAUGUGAA SEQ ID NO: 162 | [stem-loop structure] SEQ ID NO: 355 |
| miR-136 | ACUCCAUUUGUUUUGAUGAUGGA SEQ ID NO: 163 | [stem-loop structure] SEQ ID NO: 356 |

Fig.7 (cont)

| | | |
|---|---|---|
| miR-137 | UAUUGCUUAAGAAUACGGUAG SEQ ID NO. 164 | (hairpin structure) SEQ ID NO. 357 |
| miR-138 | AGCUGGUGUUGUGAAUC SEQ ID NO. 165 | (hairpin structure) SEQ ID NO. 358 |
| miR-139 | UCUACAGUGCACGUGUCU SEQ ID NO. 166 | (hairpin structure) SEQ ID NO. 359 human |
| miR-140 | AGUGGUUUUACCCUAUGGUAG SEQ ID NO. 167 | (hairpin structure) SEQ ID NO. 360 |
| miR-141 | AACACUGUCUGGUAACGAUGU SEQ ID NO. 168 | (hairpin structure) SEQ ID NO. 361 |
| miR-142s | CAUAAAGUAGAAAGCACUAC SEQ ID NO. 169 | (hairpin structure) SEQ ID NO. 362 |
| miR-142as* | UGUAGUGUUUCCUACUUUAUGG SEQ ID NO. 170 | (hairpin structure) SEQ ID NO. 363 |

Fig.7 (cont)

| | | |
|---|---|---|
| new | AUAAGAGAGCAAAAGCUUGU<br>SEQ ID NO: 418 | UGAC G C GG C AU<br>ACUG GGCGAGCUUU GC CG UUAUAC UG G<br>     UGCUUCGAAAA CG GC AAUAUG AC G<br>     A A AG C UC<br>AL049829.4<br>SEQ ID NO: 364 |
| miR-143 | UGAGAUGAAGCACUGUAGCucu<br>UUCAUCUCCAGUACUGUAG<br>SEQ ID NO: 171 | G U - AG<br>CCUGAG UGCAGUGCU CAUCUC GG UC U<br>GGACUC AUGUCACGA GUAGAG CU AG U<br>A G GG<br>AC008681.7<br>SEQ ID NO: 365 |
| miR-144 | UACAGUAUAGAUGAUGUACUAG<br>SEQ ID NO: 172 | G A- GU<br>GGCUGG AUAUCAUC UAUACUGUA GUUU G<br>CUGAUC UGUAGUAG AUAUGACAU CAGA A<br>G CA GU<br>SEQ ID NO: 366 |
| miR-145 | GUCCAGUUUUCCCAGGAAUCCCUU<br>SEQ ID NO: 173 | C UC C A-<br>CUCA GG CAGU UU CCAGGAAUCCU C<br>GAGU UC GUCA AA GGUCUUAGGGG<br>- UU U A<br>SEQ ID NO: 367 |
| miR-146 | UGAGAACUGAAUUCCAUGGGUU<br>SEQ ID NO: 174 | CU AUAUC<br>AGCU GAGAACUGAAUU C CAUGGGU<br>UCGA CUCUUGACUUAA A GUGUCCA<br>C ACUGGU<br>SEQ ID NO: 368 |
| miR-147 | GUGUGUGGAAAUGCUUCUGCC<br>SEQ ID NO: 175 | A- AGA CAA ACA--- CCA GA<br>AAUCUA CAUUUCUGCAC CA C<br>UUAGAU GUAAGGUGUG GGU AU<br>CG UC- AC CGAA<br>human<br>SEQ ID NO: 369 |
| miR-148 | UCAGUGCACUACAGAACUUUGU<br>SEQ ID NO: 176 | - A- CC AGU A<br>CAGGCAAGUUCUG AG CACU GACU CUG C<br>CUCUGUUCAAGAC UC GUGA CUGA GAU<br>A AC __ A<br>human<br>SEQ ID NO: 370 |

Fig. 7 (cont)

| | | |
|---|---|---|
| miR-149 | UCUCGGCUCCGUGUCUUCACUCC<br>SEQ ID NO: 177 | CGGCUCACGG CCUC GU UCUUC A GUG G UUU U<br>                                CCUGC GAGUG GAC C<br>UCGCUGAC GGAG CA GGAGUG CAGUUG         GAC C<br>                                A C AG- C<br>SEQ ID NO: 371 |
| miR-150 | UCUCCCAACCCUUGUACCAGUGCU<br>SEQ ID NO: 178 |                               AC        UC<br>CCCGUCUCCCA CCU GUACCAG   CUG C<br>GGGUAGGGGU GGA CAUGGUC   GAC C<br>                        CCA        UC<br>SEQ ID NO: 372 |
| miR-151 | CUAGACUGAGGCUCCUUGAGGU<br>SEQ ID NO: 179 |                 CA               UGUCU<br>CCCUG CCUGGAGGAGCU CAGUCCUAGUA   C<br>GGGAC GGACCUUCUUGA GUCAGGAUCAU   C<br>          A-                   CCCUC<br>SEQ ID NO: 373 |
| miR-152 | UCAGUGCAUGACAGAACUUGG<br>SEQ ID NO: 180 | CCGGGCCUAGGUUCU G A CACU CAGU CCU U<br>GGCCCGGGAUUCAAGACA UA GUGA CUGA   G<br>                                      C U     ---   G<br>SEQ ID NO: 374 |
| miR-153 | UUGCAUAGUCACAAAAGUGA<br>SEQ ID NO: 181 |                        GU               CCU        UUU<br>CAGUG UCAUUUCUGAU UGCACCU   UGCC     U<br>GUCAC AGUAAAGACUA ACGUGGA   ACGG     C<br>                       AU                CC    AGU<br>SEQ ID NO: 375 |
| miR-154 | UAGGUUAUCCGUGUUGCCUUCG<br>SEQ ID NO: 182 | GAAGAUAGGUA   CCGGUGU UG   CCU--   UUGGC   U<br>UUUUAUCCAU   GGCACA AC   UAAGC   AGUG    A<br>            V                      U       U<br>SEQ ID NO: 376 |
| miR-155<br>(BIC-RNA) | UUAAUGCUAAUUGUGAUAGGGG<br>SEQ ID NO: 183 | CUGUUAAUGCUAAU   G G UAGGGGU   UUGGCC<br>GACAAUUACGAUUG   U C AUCCUUAG   UCAGCC<br>                 U   U A            -      C<br>SEQ ID NO: 377 |

Fig. 7 (cont)

| name | sequence | structure | |
|---|---|---|---|
| miR-C1 | AACAUUCAACGCUGCCGGUGAGU SEQ ID NO: 184 | (structure diagram) | SEQ ID NO: 378 |
| miR-C2 | UUUUGGCAAUCGUAGAACUCACA SEQ ID NO: 185 | (structure diagram) | SEQ ID NO: 379 |
| miR-C3 | UAUGGCACUGGUAGAAUUCACUG SEQ ID NO: 186 | (structure diagram) | SEQ ID NO: 380 |
| miR-C4 | CUUUUUGCGGUUCUGGGCUUGUU SEQ ID NO: 187 | (structure diagram) | SEQ ID NO: 381 |
| miR-C5 | UGGACGGACAACUGAUAACGGU SEQ ID NO: 188 | (structure diagram) | SEQ ID NO: 382 |
| miR-C6 | UGGCAGAGAAAGGCAGUUC SEQ ID NO: 189 | (structure diagram) | SEQ ID NO: 383 |

Fig.7 (cont)

| name | sequence | structure | |
|---|---|---|---|
| miR-C7 | CAAAGAAUUCUCCUUUUGGGCUU SEQ ID NO: 190 | ACGUUCCAAAGAAUUC  U  UU  CCUU  GGGCUU  UCUUCAU  U<br>UGAAGGUUUCUUAAG  GGAA  CCCGAA  UUUUAU | SEQ ID NO: 384 |
| miR-C8 | UCGUGUCUUGUUGCUGCAGCCGG SEQ ID NO: 191 | A  GGCU  A  CAAACAGGAC  C  CGGG  CGCUGC<br>UC  CCGA  GUUCUGUUCG  GCCC  CCCAGU<br>GG  U  C | SEQ ID NO: 385 |
| miR-C9 | UAACACUGUCUGGUAACCAUGU SEQ ID NO: 192 | GGGCAUC  UUACCCGACAGUG  UGGA  UC  UU  UUG  G<br>CUUGUAG  AAUGGGUUGUUCAC  AUCU  AG  C  UUC<br>C  A  C | SEQ ID NO: 386 |
| miR-C10 | CAUCCCUUGCAUGCUGGAGGU SEQ ID NO: 193 | UCG  CA  UC  CCUUGCAUG  GU  UGAGCUC  U<br>AGG  GU  GGGGACUGUAC  CC  CAAAAGU<br>AC  UU  C | SEQ ID NO: 387 |
| miR-C11 | GUGCCUACCUGACCUGACAUCAGU SEQ ID NO: 194 | CUUCC  G  G  A  GCU  CUGACCUGA  UCAGU  UCUUCAU  U<br>GAGG  CA  A  GGA  GACUGGACU  GGUCA  CACACU<br>A  A  C | SEQ ID NO: 388 |
| miR-C12 | UGAUAUGUUGGAUAUAUUAGGU SEQ ID NO: 195 | CUGUG  UA--  GAUAUGUUGAUUAAU  UU  GGUUG  A<br>GACAU  GUAUACCACUAUAUA  UCAAC  CUAAC<br>CC  UU  U | SEQ ID NO: 389 |

Fig.7 (cont.)

| name | sequence | structure | |
|---|---|---|---|
| miR-c13 | CAACGGAAUCCAAAGCCAGCU<br>SEQ ID NO: 196 | ``` 
      C    C  AA      UU -  C
AGCGGG AACGGAAUCC  GCAGCU GU CU C
UCGUCC UUGCCUUAGG  CGUCGAC GA GA A
      C    -  CA      CU C  G
``` | SEQ ID NO: 380 |
| miR-c14 | CUUGACCUAUGAAUUGACA<br>SEQ ID NO: 197 | ```
   -    A         UCCUCUC
  UGACCUAUG AAUUG CAGCCAG  G
  ACUGGAUAC UUAAC GUCGGUC  U
   -    C         UCCCCUC
``` | SEQ ID NO: 381 |
| miR-c15 | UACCACAGGUAGAACCACGGA<br>SEQ ID NO: 198 | ```
      A          UU UC
UCCCUG CCG UGGUUUUACCCU UGGUAGG ACG A
AGGGAC GGC ACCAAGAUGGGA ACCAUCU UGU U
      -          C A    CG
``` | SEQ ID NO: 382 |
| miR-c16 | AACUGGCCUACAAGUCCCAG<br>SEQ ID NO: 199 | ```
    A  U   C    A A   AGU
CAG GCUGGA CUUG GGCC AG UGAG G
CUC UGACC GAAAC UCCG UC ACUU U
    U  C   A    G A   GAC
``` | SEQ ID NO: 383 |
| miR-c17 | UGUAACAGCAACUCCAUGUGGA<br>SEQ ID NO: 200 | ```
 U   A       G           U
U  GUAACAGCA CAUCCAU UGGA CUG G
U  CAUUGUCGU GUAGGUA ACCU GGC C
 D   -       C           UA U
``` | SEQ ID NO: 384 |
| miR-c18 | UAGCACCACAGAAAUAUUGGCA<br>SEQ ID NO: 201 | ```
 U  A-  AAUAUUGGCA  UG GAA
U  AGCACCACAG       GG G
U  UCGUCGGUGUC      CU U
    GG           -- -- CAG
``` | SEQ ID NO: 385 |

Fig.7 (cont)

| name | sequence | structure | |
|---|---|---|---|
| miR-C19 | UAGCUAGUUCAUCUGUUGG<br>SEQ ID NO: 202 | GUGAAU A GGU GUU AUGUUGUUG GGCCUGGG U<br>CACUUAG CCA CAA UACAACAAC D<br>C C A A ACAAGUCU | SEQ ID NO: 396 |
| miR-C20 | UUCACCACCUUCCUCCACCAGC<br>SEQ ID NO: 203 | C A CA GA A<br>GGCUGUGC GGGU GAGAGGG GUGG GGU AAG G<br>CCGGUACG CCCA CUCUCCC CACU CCA UUC C<br>A C C U C U U | SEQ ID NO: 397 |
| miR-C21 | GGUCCAGGGAGACAUAGG<br>SEQ ID NO: 204 | G- C,G U UUCCUUG U<br>UCAUU G UC A AGGGAGA AGG G<br>AGUAA U XG U UCCUUCU UCC<br>A A A A GUUUUUA | SEQ ID NO: 398 |
| miR-C22 | CCCAGUGUUCAGACUACCUGUU<br>SEQ ID NO: 205 | AAC C U G C G<br>GCC CCAGUGU CAGACUAC UG CA GAG C<br>CGG GGUACA GUCUGAUG ACA GU CUC U<br>CGG CA A AUU GUAA | SEQ ID NO: 399 |
| miR-C23 | UAAUUACUGCCUGGUAAUGAUGAC<br>SEQ ID NO: 206 | GGC C UAGUG U<br>GCCCGU CAUC UUACUGGCCAG AUUGGA C<br>CGGGCA GUAG AAUGGCCGGUC UAACCU U<br>U A CUAGU | SEQ ID NO: 400 |
| miR-C24 | UACUCAGUAAGGCAUGUUCU<br>SEQ ID NO: 207 | UUC A U<br>UACCUUAC CAG AAGGCAUGUUC UAU U C<br>AUGGAUG GUC UUCCGUGACAAG AUA A U<br>U UAA A CUAGU | SEQ ID NO: 401 |

Fig.7 (cont)

| name | sequence | structure |
|---|---|---|
| miR-C25 | AGAGGUAUAGGCAUGGGAAGA SEQ ID NO: 208 | ``` U         A-    UG       C GGUCC UUUCCUAGC  UAUACUUCUU  UGGAU   CCAGG AGAAGGUUAG  AUAUGGAAGA  AUCUG  G       C-        CG      G ``` SEQ ID NO: 402 |
| miR-C26 | UGAAAUGUUUAGGACCACUAG SEQ ID NO: 209 | ``` C         U G   A   C U CGGUC AGUGGUUCU GACA UUCA CAGUU UG  A CCAG UCACCAAGGA UCUG AAGU GUUAA AC  G       A         U -   A   C G ``` SEQ ID NO: 403 |
| miR-C27 | UUUCCCUUGUCAUCCUAGCCCUG SEQ ID NO: 210 | ``` U     U           GAGAAUA UGGAC UCCCUUUGUC UCCU GCCU    U ACUUG AGGGAAACAG AGGU CGGA    GGAAGUA  C     C           - ``` SEQ ID NO: 404 |
| miR-C28 | UCCCUUCAUUCCACGGAGUCUG SEQ ID NO: 211 | ``` UC            U CUCUUG CUUCAUUCCAC GGAGUCUG  UCUUA GAGGAC GAAGUGAGGUG CUUCAGAC CAAC    UC                 - ``` SEQ ID NO: 405 |
| miR-C29 | GUGAAAUGUUUAGGACCACUAGA SEQ ID NO: 212 | ``` U   C         U G  A   UUCA CAGUU  UG    C U GCC GGUC AGUGGUUCU GACA         AC  A CGG CCAG UCACCAAGGA UCUG AAGU GUUAA    U  G C   C         A -  U   G ``` SEQ ID NO: 406 |
| miR-C30 | UGGAAUGUAAGCAAGUUCUGG SEQ ID NO: 213 | ``` -          C U         AUAUC CCAGG CCACAUGCUUCUUUAUAU C CAUAG  U GGUUU GGUGUGUGAAGGAAUGUA  G GUAUC ACGAC            A -         ``` SEQ ID NO: 407 |

Fig.7 (cont)

| name | sequence | structure | |
|---|---|---|---|
| miR-C31 | UACAGUAGUCUGCACAUUGGUU SEQ ID NO:214 | AUC      U        C          UCAG A   G<br>GCC  CCAGUGU  CAGACUAC  UGU      G<br>CGC  GGUACA   GUCUGAUG  ACA      G<br>AUU      C        -         GGUC  G<br>                                 UGUACAG | SEQ ID NO:408 |
| miR-C32 | CCCGUAGAACGGAAUUGUGU a miR-10 variant SEQ ID NO:215 | A    G     C      UG-   AC  C<br>UAUAU  CCCU  UAGAA  CGAAUUGUG  GU C<br>AUAUA  GGGC  AUCUU  GCUUAGCAC  CA C<br>A    -     -      UGA   CA | SEQ ID NO:409 |
| miR-C33 | AACCCGUAGAUCCGAACUUGUGA a miR-99a variant SEQ ID NO:216 | A   C    C     A    AU U<br>CACA  ACC  GUAGAU  CGA  CUUGUG  UG  U<br>GUGU  UGG  UAUCUG  GUU  GAACAC  AC  C<br>A   A    -     U    -  GU | SEQ ID NO:410 |
| miR-C34 | GCUUCUCCCUGGCUCUCCCCUC SEQ ID NO:217 | C    U    UUG          GGAG  C<br>AAGG  AGGGG  GAGGGC  CCGGAGGAGC  CCGGC  G<br>UUCC  UCCCC  CUCCCG  GGCCUCUUCG  GGUCG  C<br>-    -    UCG          GCGU | SEQ ID NO:411 |

Fig.7 (cont.)

| name | human | c.elegans | mouse liver | small intes | colon | cerebellum | cortex | midbrain | heart | spleen | Drosophila | fugu fish | zebrafish |
|---|---|---|---|---|---|---|---|---|---|---|---|---|---|
| let-7a-1 | AC007924 chr9 AC087784 chr 17 identical precursor | | num.hits in trace date, 3 families of similar precursors | | found | | nearly identical precursor | found | | | | | |
| let-7a-2 | AP001359 chr11 | | | | | | nearly identical precursor | | | | | | |
| let-7a-3 | AL049853 chr22 | AF274345 chrX with diff. precursor | | | | | | | | | AE003659 diff. Precursor | | |
| let-7b | AL049853 chr22 | | nearly identical precursor | | | nearly ident precursor trace#48311003 | | found | | EST AI481799.1 spleen = cerebellum (mammary) | | with slightly diff precursor | |
| let-7c | AP001667 chr21 | | identical and diff. precursors | | | num.genomic hits, ident precursor;diff precursor -> EST AI614897 | numerous genomic hits | found | | | | | |
| let-7d | AC007924.3 chr9 AC087784 chr17 identical | | | | found | trace#8358704*2 nearly ident prec | trace#8358704*2 nearly ident prec | found | found | | | | |

| | | | | | | | | |
|---|---|---|---|---|---|---|---|---|
| let-7e | AC018755 chr19 | | | found | FOUND | | | |
| let-7f-1 | AC007924 chr9<br>AC087784 chr17 | | ident precursor<br>genomic DNA | found | found | | | |
| let-7f-2 | AL592046 chrX | | ident. precursor<br>in nmtrace<br>18713911 | | | | | |
| let-7g | precursor<br>ident. to mouse<br>in AC092045.2<br>chr3 | | genomic hits, no<br>EST | found | | | | |
| let-7h | | | found in<br>cortex, no db<br>hit | | | | | |

Fig. 7 (cont.)

Fig.7 (cont.)

| | precursor | | | found, supported by EST BB661268 | found | | | | |
|---|---|---|---|---|---|---|---|---|---|
| let-7i | ident. to mouse [Al17383.19]; also AC048341.22 | | | | | | | | |
| miR-1 | | | | | | | | 2L,AE003667 | |
| miR-1b | AJ49263.5 chr20 ntl-21 | U97405.1 nt 1-21 (22G) | no mouse hit (only ntl-21) | | found | | | | |
| miR-1c | | | | | | | | | |
| miR-1d | AJ49263.5 chr20 ntl-22 (23G) | | | | | found, but no db hit | found | | |
| | | | | | | trace hits(ntl-23) trace#91 523974 | | BF157601.1 with c23 (diff. precursor) | |
| miR-2a-1 | | | | | | | | 2L,AE003663 | |

| | | | | | | | | | | |
|---|---|---|---|---|---|---|---|---|---|---|
| miR-2a-2 | | | 2L,AE003663 | | | | | | | |
| miR-2b-1 | | | 2L,AE003620 | | | | | | | |
| miR-2b-2 | | | 2L,AE003663 | | | | | | | |
| miR-3 | | | 2R,AE003795 | | | | | | | |
| miR-4 | | | 2R,AE003795 | | | | | | | |

Fig.7 (cont.)

Fig.7 (cont.)

| | | | | | | | | | | | |
|---|---|---|---|---|---|---|---|---|---|---|---|
| miR-5 | | | | | | | | | 2R,AE003795 | | |
| miR-6-1 | | | | | | | | | 2R,AE003795 | | |
| miR-6-2 | | | | | | | | | 2R,AE00379 | | |
| miR-6-3 | | | | | | | | | 2R,AE00379 | | |
| miR-7 | AC003791 chr19 diff.precursor; EST BF373391 again different | | | | | not cloned, but mouse EST predicts precursor similar to human | | | 2R,AE003791 | | |
| miR-8 | | | | | | | | | 2R,AE003805 | | |

| | | | | | |
|---|---|---|---|---|---|
| miR-9 | AC005316 chr15 AC026701 chr5 each with diff. precursor | | | found | 3L,AE003516 2diff precurs scaffold 3868 and 2417 |
| miR-10 | AF287967 chr11 (HOX B4/B5) | AF155142.1 chr19 diff prec.sligh.diff pec.s in trace hits | | | AE001574 |
| miR-11 | | not found, but AC011194 chr.11 predicts diff. precursor | | | 3R,AE003735 |
| miR-12 | | | | | X,AE003499 |
| miR-13a | | | | | 3R,AE003708 |

Fig.7 (cont.)

Fig. 7 (cont.)

| | | | | | | | | | | | |
|---|---|---|---|---|---|---|---|---|---|---|---|
| miR-13b-1 | | | | | | | | | | | 3R,AE003708 |
| miR-13b-2 | | | | | | | | | | | X,AE003446 |
| miR-14 | | | | | | | | | | | 2R,AE003833 |
| miR-15a | 13, AC069475 | | | | | | | found | trace#72 137197 prec slig diff | | |
| miR-15b | | | | | | | | | trace#79 105069 | | |

| | | | | | | |
|---|---|---|---|---|---|---|
| miR-16 | 13, AC069475 interesting leukemia locus | | | | found | | AL606727 diff precurs |
| miR-16 | 3, NT_005740.6 | several trace,nearly ident precursor | found | genomic hits with 2 slightly diff precur.trace#502 93836,78368680 | found trace#7910506 9;nearly ident prec. as in human | found | |
| miR-17 | 13, AL138714 | | | | | | |
| miR-18 | 13, AL138714 | | | | | | |
| miR-19a | 13, AL138714 | | | | | | |
| miR-19b-1 | 13, AL138714 | | | | | found | G46757 with a U9C |

Fig.7 (cont.)

Fig.7 (cont.)

| | | | | | | | | | |
|---|---|---|---|---|---|---|---|---|---|
| miR-19b-2 | X, AC002407 | | | | | | | | |
| miR-20 | 13, AL138714 | | found | | | | | | |
| miR-21 | 17, AC004686 | | AL604063 chr11, nearly ident precursor | found | | | | | |
| miR-22 | several highly similar ESTs: AW961681 shown | cDNAa from var. tissues, identical precursor | AK008813 cDNAs, same precursor | | AK008813 (cDNA), prec ident to human | | found | | |
| miR-23a | 19, AC020916 | | | | | | found | | |
| miR-23b | XM 072557.1 chr9, also human ESTs, prec nearly ident to mouse | | | | | EST AW124037 hypothal, EST AI848465 cerebellum | found trace#62 540691 prec sli diff | | three hits in db |

Fig. 7 (cont.)

| | | | | | | | |
|---|---|---|---|---|---|---|---|
| miR-24-1 | 9, AF043896 | | found | | | | |
| miR-24-2 | 19, AC020916 | | | found.EST AI286629 (thymus); nearly ident. to miR-24-1; EST AA111466 (whole embryo) different precursor | found | found | |
| miR-25 | 7, AC073842 second ident.copy found in chr7 | predicted in mouse (EST AI595464), but not cloned | | | | | |
| miR-26a | 3, AP000497 | | | AC055818.9,tr ace#88471973 precursor diff. from human | found | | Scaffold_4097 different precursor | G46757 similar precursor |
| miR-26b | 2, AC021016 | found | | found,trace#6986 6494,slight.diff precursor | | | |

Fig.7 (cont.)

| | | | found | found, but no db hit | found, but no db hit for mouse | found | found | found | | | |
|---|---|---|---|---|---|---|---|---|---|---|---|
| miR-27a | 19, AC020916 | | | | | | | | | | |
| miR-27b | XM_098943.1 chr9 identical precursor | | | | | found, maps to chr 13 MGSC mmtrace 44671617 | | | | | |
| miR-28 | 3, AC063932 | | | | | | | | | | |
| miR-29a | 7, AF017104 second ident.copy found in chr7 CLUSTER, this cluster also consvd in mouse: AC024913.32 | | found, AC024913.3 2 | found, mmtrace#23467334 | nearly ident precursor trace#2346733 4, EST AC024913.32 | | trace, EST, nearly ident prec | | | | |
| miR-29b | AL035209.1 chr1 CLUSTER of miR-29-b and 29-c; miRNA similar to miR-83 | | found | | AC024913.32;d iff precursor in EST BG342396 (retina) | AC024913.32;d found | FOUND | | | Scaffold 117670. (A third copy) | |

| | | | | | | | | |
|---|---|---|---|---|---|---|---|---|
| miR-29c | | | | found | found | found, supportd by ESTs | | |
| miR-30a-s | nearly ident fold in AL035467.23 chr6 | found;ESTs ,trace6802 ,3889 all with 22G | | found | found | | found | Scaffold 17670 has two copies of this RNA |
| miR-30a-as | 6, AL035467 | | found with diff. precursor in trace #85261735 | | | | | |
| miR-30b | human AF159227.6 chr8,different precursor | | trace#7232925l | found | | | found | Scaffold 3483,diff precursor |
| miR-30c | AL136164.8 chr.6 supported by ESTs (BF594736.1) | | found,but no db hit for mouse | | | found | found | |

Fig.7 (cont.)

Fig.7 (cont.)

| | | | | | | | |
|---|---|---|---|---|---|---|---|
| miR-30d | AF159227.5 chr8 | | | | | | Scaffold 3483,diff fold |
| miR-31 | 9, AL353732 | | | | | | |
| miR-32 | 9, AL354797 | | | | | | |
| miR-33 | 22, Z99716 | | | | | | |
| miR-99a | AP000962.2 chr21,ident to mouse;[similar to miR-10 and miR-51] | | | trace#48910714 | | | G44780 with diff.precursor |
| miR-99b | AC018755.3 chr.19; [similar to miR-10 and miR-51] | | mmtrace #92340982 | | found, but no mouse db hit | | |

| | | | | | | |
|---|---|---|---|---|---|---|
| miR-101 | AL158147.17 chr9 diff precursor | | | | | |
| miR-122a | | abundant but no db hit, except woodchuck x13234 | | | AK021368.1 cDNA eyeball | found |
| miR-122b | | | | | | |
| miR-122a,b | | | | | | |
| miR-123 | | genomic hits (trace#6108 147), no EST | | | | U53213.1 T.fluviat ilis | | | Scaffold_ 3295 |

Fig.7 (cont.)

Fig.7 (cont.)

| | | | | | | |
|---|---|---|---|---|---|---|
| miR-124a* | nearly ident. precursor in chr8[AC021518] chr20[AL096828] | found in z72504.1 chrIV intron,diff precursor | found | most abundant in cereb.,genomic hits (trace#21097088, 11737241) | most abundant;several trace hits;precurs= cerebellum | found | slightly diff precursor AC009251 chr2L |
| miR-124b | AC021518 chr8,nearly ident chr20 AL096828.29 | | | found, but no db hit | found | | |
| miR-125a | ident precur in AC018755.3 chr 19 | | | genomic hits trace#33921945, 48262259 and more | found | | |
| miR-125b | AP001359.4 chr11 AP001667.1 chr21(chr21 like mouse) | | | | trace#8398570 and 5 | found with A22U | found in AC006590.1 with diff fold | Scaffold_2358 |
| miR-126 | | | | umtrace#3521597 and more | | found | with diff precursSc affold_32_95 |
| miR-127 | human AL117190.6 chr.14 same precurs as in mouse | | | hit in trace#7951453? | | | |

| | | | | | genomic hit | | | Scaffold 828,diff prec | |
|---|---|---|---|---|---|---|---|---|---|
| miR-128 | ident in AC016742.10 chr 2;diff prec in AC016943.7 chr.3 | | | | trace#51670230 | found | found | | |
| miR-129 | human AC018662.3 chr7 | | | | found, but no db hit | | | | |
| miR-130 | | | | | mmtrace 68479278 | | | with diff fold AC091299.2 | |
| miR-131 | AC005317.2 chr 15 sligh.diff precursor,but AC026701.6 chr 5 ident | | | | several trace hits,mouse AF155142 | found | | | |
| miR-132 | AL137038.5 chr17 prec sligh.diff from mouse | | | | trace hit#86984641 | | | | |

Fig.7 (cont.)

Fig.7 (cont.)

| | | | | | | | | | |
|---|---|---|---|---|---|---|---|---|---|
| miR-133 | AL391221.15 chr6 diff. Precursor(ident to rat L33722.1) | | | | | found, trace# 62407955 | found | AC093440.1 diff. Precursor u nearly like mouse | Scaffold 1049;prec nearly like mouse |
| miR-134 | AL132709.5 chr14 similar precursor | | | | | trace#6462031 1 | | | |
| miR-135 | AC092045.2 chr3 AC018659.35 chr12 (ident or simil to mouse) | | | | | trace#7149523 5,ESTBF780995 .1(kidn.,sple en)(=chr3huma n) | found | | Scaffold 2125 with similar precurs |
| miR-136 | AL117190.6 chr14 ident to mouse | | | | | trace#8607175 3 | | | |
| miR-137 | AC027691.1 chr1 ,ident to mouse,nearly ident fish | | | | | trace#897745 3,EST (hypothal)AI8 52436.1,ident | | | Scaffold 18244 nearly ident to mouse/man |
| miR-138 | AC006058.1 chr3 precursor diff | | | | | mouse EST BB528620.2 | | | |

| | | | | | | | | |
|---|---|---|---|---|---|---|---|---|
| miR-139 | AP003065.2 chr11 | | | | found, but no mouse hit | | | |
| miR-140 | AC026468.8 chr.16, precursor nearly ident. | | several trace hits; trace#1053 0393 | | | | | |
| miR-141 | AC006512.12 chr12, precursor slightli diff | | AC002397 chr6 | | | | | |
| miR-142s | AC004687.1 chr17 BCL3/myc translocation locus, like mouse | | found | | | found | | |
| miR-142as* | | | several EST AI153235 | | | found | | |

Fig.7 (cont.)

Fig.7 (cont.)

| ID | description | | | | | | |
|---|---|---|---|---|---|---|---|
| new | AI049829.4 chr14 | | | | found but no db hit | | |
| miR-143 | AC008681.7 chr5 | | found, but no db hit | | found | found | |
| miR-144 | XM_064366.1 precursor nearly ident | found | | | EST AA290206 .1,trace 2143909 | | |
| miR-145 | AC008681.7 chr5 GG->GA,precur nearly like mouse, see 2 positions above | | | | found EST BF163348 .1 lung | | |
| miR-146 | AC008388.7 chr5 diff precursor | | | | trace#34 639321 | Scaffold 934 similar | |
| miR-147 | AL592549.7 | | | | | found | |

| | | | | | | | | | | |
|---|---|---|---|---|---|---|---|---|---|---|
| miR-148 | AC010719.4 | | | | | | | | | |
| miR-149 | | | | | | | | found, no db hit | | |
| miR-150 | | | trace#8472 1065,10352 801 | | | | | trace#85 955550 | | |
| miR-151 | | | trace#8845 6669 | | | | | | | |
| miR-152 | human chr 17 AC004477.1, nearly identical | | found in colon,supportd by trace#83700445;close match MGSC in chr18 (additional 14C unlikely, not supported by trace and | | | | | | | |

Fig.7 (cont.)

Fig. 7 (cont.)

| | | | | | | | | | | | | |
|---|---|---|---|---|---|---|---|---|---|---|---|---|
| miR-153 | AC006372.2 chr7 ident. precursor | | | | | | | | | | | |
| miR-154 | AL132709.5 chr14 nearly identical precursor | | | | | | found sever. mmtrace 87010874 | | | | | |
| miR-155 [BIC-RNA] | human BIC RNA:AF402776.1 (has U12C) | | | found; chr 16 mouse | | | found sever. mmtrace 86715639 | | | | | |

Fig.7 (cont.)

| name | human | mouse | | | | | | Drosophila | fugu fish | zebrafish |
| --- | --- | --- | --- | --- | --- | --- | --- | --- | --- | --- |
| | | spleen | eye | kidney | testes | lung | thymus | skin | | | |
| miR-C1 | with different precursors in chr9 AL158075.11, chr1 AL136321.5 | | mouse trace #76647842 | | | found | | found | | scaffold_1819 | |
| miR-C2 | chr7 AC084864.2 similar precursor | | mouse trace #88841093 | | | | | | | scaffold_967 | AL590150.2 |
| miR-C3 | chr7 AC084864.2 ident.precursor | | trace #86029980 | | | | | | | scaffold_967 | AL590150.2 |
| miR-C4 | similar precurs.in chr7 AC018662.3 | | trace #13885686 | | found | | | | | | |
| miR-C5 | chr15 AC069082.9 | | trace #87318220 | | | | | | found | scaffold_3671 | |
| miR-C6 | chr22 AC005664.2 ident.precursor | | chr16 AC012526.32 | | | | | | | | |
| miR-C7 | chr1 AL512443.7 similar prec. | | trace #86694995 | | | | | | | | |

| | | | | | | | |
|---|---|---|---|---|---|---|---|
| miR-C8 | | | found, trace #51673384 | | | | |
| miR-C9 | | | found, trace #78964803 | | scaffold 2210, diff. precursor | | |
| miR-C10 | chrX AF222686.1 nearly ident. precursor | | found, trace #61928192 | | | | |
| miR-C11 | chr9 XM_098943.1 has C17U;prec.nearly identical to mouse | | found,cDNA AI286629.1, has C17U | | | | |
| miR-C12 | | found | found,trace#71 760450 | | | | |
| miR-C13 | | | found,trace #88722637 | | scaffold_2294 | | |

Fig.7 (cont.)

Fig.7 (cont.)

| name | human | mouse | | | | | | | Drosophila | fugu fish | zebrafish |
|---|---|---|---|---|---|---|---|---|---|---|---|
| | | spleen | eye | kidney | testes | lung | thymus | skin | | | |
| miR-C14 | chr11 AC000159.6 | | | found, but no db hit | | | | | | | |
| miR-C15 | chr16 AC026468.6 nearly ident.precursor | | | EST BI687377.1, several trace | | | | | | scaffold_2083 | |
| miR-C16 | chr3 AC003101.1, similar precursor | | | found,trace#95 55103 | | | | | | scaffold_246 | |
| miR-C17 | chr11 AC000159.6, chr1 AC103590.2; diff.prec. | | | found, trace #87796602 | | | | | | scaffold_152 | |
| miR-C18 | | | | found, trace #47823768 (close to miR-16) | | found | | found | | | |
| miR-C19 | chr17 AC009789.21 cloned from human cell line only | | | similar precursor in mouse chr11 AC011194.15 | | | | | | scaffold_18334 | |
| miR-C20 | chr1 AL355310.19 cloned from human cell line only | | | | | | | | | | |

| | | | | | | | | | |
|---|---|---|---|---|---|---|---|---|---|
| miR-C21 | chr3 AC063952.15 cloned from human cell line only | | | | | | | | |
| miR-C22 | chr19 AC007229.1; chr1 AL137157.7 similar precursor; cloned from human cell line only | | | | | scaffold_8399 | | | |
| miR-C23 | | | | found | | scaffold_2210 | | | |
| miR-C24 | | | | trace #72257777 | | | | | |
| miR-C25 | | | | trace #69879879 | | | | | |
| miR-C26 | AL136001 ident. precursor | | | trace #49754566 | | | | | |
| | | | | trace #11977216 | | | | | |

Fig.7 (cont.)

Fig.7 (cont.)

| name | human | mouse | | | | | | Drosophila | fugu fish | zebrafish |
|---|---|---|---|---|---|---|---|---|---|---|
| | | spleen | eye | kidney | testes | lung | thymus | skin | | |
| miR-C27 | chr9 AL159990.12 identical precursor | | trace #91503159 | | | | | | | scaffold_725 | |
| miR-C28 | XM_036612.4, precursor very similar | | | | | | | XM_149012.1 | | scaffold_13664 | |
| miR-C29 | chr14 AL136001.6 nearly identical precursor | | | | | | | trace #18453604 | | | |
| miR-C30 | chr6 AL391221.15 similar precursor | | | | | | | trace #84055510 | | | |
| miR-C31 | chr9 AC006312.8 | | | | | | | trace #89079710 | | scaffold_5830 | |
| miR-C32 | | | | | | | | U77364.1, intronic location Hoxd4 gene | | scaffold_82 | |
| miR-C33 | | | | | | | | trace #84780544 | | scaffold_15612 | |
| miR-C34 | | | | | | | trace# 72109322 | | | | |

SEQUENCE LISTING

<160> NUMBER OF SEQ ID NOS: 418

<210> SEQ ID NO 1
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 1
tactatacaa cctactacct caatttgcc                                    29

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
actatgcaac ctactacctc t                                            21

<210> SEQ ID NO 3
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 3
actatacaac ctcctacctc a                                            21

<210> SEQ ID NO 4
<211> LENGTH: 19
<212> TYPE: DNA
<213> ORGANISM: Artificial Sequence
<220> FEATURE:
<223> OTHER INFORMATION: Synthetic Oligonucleotide

```
<400> SEQUENCE: 4
tggtgtttcc gcccgggaa                                                   19

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 5
tggaatgtaa agaagtatgg ag                                               22

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
gctcctcaaa gctggctgtg ata                                              23

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
tgagacacac tttgcccagt ga                                               22

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
tcaatggttg tctagcttta t                                                21

<210> SEQ ID NO 9
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 9
catatcacaa cgatcgttcc ttt                                              23

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 10
aaaaagaaca gccactgtga ta                                               22

<210> SEQ ID NO 11
<211> LENGTH: 23
```

```
<212> TYPE: DNA
<213> ORGANISM: Artificial Sequence
<220> FEATURE:
<223> OTHER INFORMATION: Synthetic oligonucleotide

<400> SEQUENCE: 11
tggaagacta gtgattttgt tgt                                          23

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 12
gacatcttta cctgacagta tta                                          23

<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 13
tcatacagct agataaccaa aga                                          23

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 14
acaaattcgg atctacaggg t                                            21

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
gcaagaactc agactgtgat g                                            21

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 16
accagtacct gatgtaatac tca                                          23

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
actcgtcaaa atggctgtga ta                                           22
```

-continued

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
taggagagag aaaaagactg a                                              21

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
tagcagcaca taatggtttg t                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
gccaatattt acgtgctgct a                                              21

<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 21
tacaagtgcc ttcactgcag ta                                             22

<210> SEQ ID NO 22
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 22
tatctgcact agatgcacct ta                                             22

<210> SEQ ID NO 23
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 23
tcagttttgc atagatttgc aca                                            23

<210> SEQ ID NO 24
<211> LENGTH: 22
<212> TYPE: DNA
<213> ORGANISM: Artificial Sequence
<220> FEATURE:
<223> OTHER INFORMATION: Synthetic oligonucleotide

```
<400> SEQUENCE: 24
tacctgcact ataagcactt ta                                              22

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 25
tcaacatcag tctgataagc ta                                              22

<210> SEQ ID NO 26
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 26
acagttcttc aactggcagc tt                                              22

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 27
ggaaatccct ggcaatgtga t                                               21

<210> SEQ ID NO 28
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 28
ctgttcctgc tgaactgagc ca                                              22

<210> SEQ ID NO 29
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 29
tcagaccgag acaagtgcaa tg                                              22

<210> SEQ ID NO 30
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 30
agcctatcct ggattacttg aa                                              22

<210> SEQ ID NO 31
<211> LENGTH: 22
```

```
<212> TYPE: DNA
<213> ORGANISM: Artificial Sequence
<220> FEATURE:
<223> OTHER INFORMATION: Synthetic oligonucleotide

<400> SEQUENCE: 31
agcggaactt agccactgtg aa                                             22

<210> SEQ ID NO 32
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 32
ctcaatagac tgtgagctcc tt                                             22

<210> SEQ ID NO 33
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 33
aaccgatttc agatggtgct ag                                             22

<210> SEQ ID NO 34
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 34
gctgcaaaca tccgactgaa ag                                             22

<210> SEQ ID NO 35
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 35
cagctatgcc agcatcttgc ct                                             22

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 36
gcaacttagt aatgtgcaat a                                              21

<210> SEQ ID NO 37
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 37
tgcaatgcaa ctacaatgca cc                                             22
```

<210> SEQ ID NO 38
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 38
ctccatactt ctttacattc ca                                            22

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 39
gctgagtgta ggatgtttac a                                             21

<210> SEQ ID NO 40
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 40
gcttccagtc gaggatgttt aca                                           23

<210> SEQ ID NO 41
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 41
cgcaaggtcg gttctacggg tg                                            22

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
tcagttatca cagtactgta                                               20

<210> SEQ ID NO 43
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 43
acaaacacca ttgtcacact cca                                           23

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide

```
<400> SEQUENCE: 44
tggcattcac cgcgtgcctt a                                              21

<210> SEQ ID NO 45
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 45
cacaggttaa agggtctcag gga                                            23

<210> SEQ ID NO 46
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 46
tcacaagtta gggtctcagg ga                                             22

<210> SEQ ID NO 47
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 47
agccaagctc agacggatcc ga                                             22

<210> SEQ ID NO 48
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 48
aaaagagacc ggttcactct ga                                             22

<210> SEQ ID NO 49
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 49
gcaagcccag accgaaaaaa g                                              21

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
gcccttttaa cattgcactc                                                20

<210> SEQ ID NO 51
<211> LENGTH: 21
```

```
<212> TYPE: DNA
<213> ORGANISM: Artificial Sequence
<220> FEATURE:
<223> OTHER INFORMATION: Synthetic oligonucleotide

<400> SEQUENCE: 51
actttcggtt atctagcttt a                                              21

<210> SEQ ID NO 52
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 52
acgaccatgg ctgtagactg tta                                            23

<210> SEQ ID NO 53
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 53
tgagctacag tgcttcatct ca                                             22

<210> SEQ ID NO 54
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' - phosphate
<220> FEATURE:
<221> NAME/KEY: misc_feature
<222> LOCATION: (1)..(3)
<223> OTHER INFORMATION: Bases 1 - 3 are RNA
<220> FEATURE:
<221> NAME/KEY: misc_feature
<222> LOCATION: (18)..(18)
<223> OTHER INFORMATION: 3' - Amino-Modifier C-7

<400> SEQUENCE: 54
uuuaaccgcg aattccag                                                  18

<210> SEQ ID NO 55
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (16)..(18)
<223> OTHER INFORMATION: Bases 16 - 18 are RNA

<400> SEQUENCE: 55
acggaattcc tcactaaa                                                  18

<210> SEQ ID NO 56
<211> LENGTH: 24
<212> TYPE: DNA
<213> ORGANISM: Artificial Sequence
<220> FEATURE:
<223> OTHER INFORMATION: Synthetic oligonucleotide
```

-continued

```
<400> SEQUENCE: 56
gactagctgg aattcgcggt taaa                                          24

<210> SEQ ID NO 57
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 57
cagccaacgg aattcctcac taaa                                          24

<210> SEQ ID NO 58
<211> LENGTH: 22
<212> TYPE: RNA
<213> ORGANISM: Drosophila melanogaster

<400> SEQUENCE: 58
uggaauguaa agaaguaugg ag                                            22

<210> SEQ ID NO 59
<211> LENGTH: 23
<212> TYPE: RNA
<213> ORGANISM: Drosophila melanogaster

<400> SEQUENCE: 59
uaucacagcc agcuuugaug agc                                           23

<210> SEQ ID NO 60
<211> LENGTH: 23
<212> TYPE: RNA
<213> ORGANISM: Drosophila melanogaster

<400> SEQUENCE: 60
uaucacagcc agcuuugagg agc                                           23

<210> SEQ ID NO 61
<211> LENGTH: 22
<212> TYPE: RNA
<213> ORGANISM: Drosophila melanogaster

<400> SEQUENCE: 61
ucacugggca aagugugucu ca                                            22

<210> SEQ ID NO 62
<211> LENGTH: 21
<212> TYPE: RNA
<213> ORGANISM: Drosophila melanogaster

<400> SEQUENCE: 62
auaaagcuag acaaccauug a                                             21

<210> SEQ ID NO 63
<211> LENGTH: 23
<212> TYPE: RNA
<213> ORGANISM: Drosophila melanogaster

<400> SEQUENCE: 63
aaaggaacga ucguugugau aug                                           23

<210> SEQ ID NO 64
<211> LENGTH: 22
```

```
<212> TYPE: RNA
<213> ORGANISM: Drosophila melanogaster

<400> SEQUENCE: 64
uaucacagug gcuguucuuu uu                                              22

<210> SEQ ID NO 65
<211> LENGTH: 23
<212> TYPE: RNA
<213> ORGANISM: Drosophila melanogaster

<400> SEQUENCE: 65
uggaagacua gugauuuugu ugu                                             23

<210> SEQ ID NO 66
<211> LENGTH: 23
<212> TYPE: RNA
<213> ORGANISM: Drosophila melanogaster

<400> SEQUENCE: 66
uaauacuguc agguaaagau guc                                             23

<210> SEQ ID NO 67
<211> LENGTH: 23
<212> TYPE: RNA
<213> ORGANISM: Drosophila melanogaster

<400> SEQUENCE: 67
ucuuugguua ucuagcugua uga                                             23

<210> SEQ ID NO 68
<211> LENGTH: 21
<212> TYPE: RNA
<213> ORGANISM: Drosophila melanogaster

<400> SEQUENCE: 68
acccuguaga uccgaauuug u                                               21

<210> SEQ ID NO 69
<211> LENGTH: 21
<212> TYPE: RNA
<213> ORGANISM: Drosophila melanogaster

<400> SEQUENCE: 69
caucacaguc ugaguucuug c                                               21

<210> SEQ ID NO 70
<211> LENGTH: 23
<212> TYPE: RNA
<213> ORGANISM: Drosophila melanogaster

<400> SEQUENCE: 70
ugaguauuac aucagguacu ggu                                             23

<210> SEQ ID NO 71
<211> LENGTH: 22
<212> TYPE: RNA
<213> ORGANISM: Drosophila melanogaster

<400> SEQUENCE: 71
uaucacagcc auuuugacga gu                                              22

<210> SEQ ID NO 72
<211> LENGTH: 22
```

```
<212> TYPE: RNA
<213> ORGANISM: Drosophila melanogaster

<400> SEQUENCE: 72
uaucacagcc auuuugauga gu                                      22

<210> SEQ ID NO 73
<211> LENGTH: 21
<212> TYPE: RNA
<213> ORGANISM: Drosophila melanogaster

<400> SEQUENCE: 73 ucagcuuuu ucucucuccu a                                        21

<210> SEQ ID NO 74
<211> LENGTH: 22
<212> TYPE: RNA
<213> ORGANISM: Drosophila melanogaster

<400> SEQUENCE: 74
ugagguagua gguuguauag uu                                      22

<210> SEQ ID NO 75
<211> LENGTH: 22
<212> TYPE: RNA
<213> ORGANISM: Homo sapiens

<400> SEQUENCE: 75
ugagguagua gguuguauag uu                                      22

<210> SEQ ID NO 76
<211> LENGTH: 22
<212> TYPE: RNA
<213> ORGANISM: Homo sapiens

<400> SEQUENCE: 76
ugagguagua gguugugugg uu                                      22

<210> SEQ ID NO 77
<211> LENGTH: 22
<212> TYPE: RNA
<213> ORGANISM: Homo sapiens

<400> SEQUENCE: 77
ugagguagua gguuguaugg uu                                      22

<210> SEQ ID NO 78
<211> LENGTH: 21
<212> TYPE: RNA
<213> ORGANISM: Homo sapiens

<400> SEQUENCE: 78
agagguagua gguugcauag u                                       21

<210> SEQ ID NO 79
<211> LENGTH: 21
<212> TYPE: RNA
<213> ORGANISM: Homo sapiens

<400> SEQUENCE: 79
ugagguagga gguuguauag u                                       21

<210> SEQ ID NO 80
<211> LENGTH: 22
```

```
<212> TYPE: RNA
<213> ORGANISM: Homo sapiens

<400> SEQUENCE: 80
ugagguagua gauuguauag uu                                          22

<210> SEQ ID NO 81
<211> LENGTH: 22
<212> TYPE: RNA
<213> ORGANISM: Homo sapiens

<400> SEQUENCE: 81
uagcagcaca uaaugguuug ug                                          22

<210> SEQ ID NO 82
<211> LENGTH: 22
<212> TYPE: RNA
<213> ORGANISM: Homo sapiens

<400> SEQUENCE: 82
uagcagcacg uaaauauugg cg                                          22

<210> SEQ ID NO 83
<211> LENGTH: 20
<212> TYPE: RNA
<213> ORGANISM: Homo sapiens

<400> SEQUENCE: 83
acugcaguga aggcacuugu                                             20

<210> SEQ ID NO 84
<211> LENGTH: 22
<212> TYPE: RNA
<213> ORGANISM: Homo sapiens

<400> SEQUENCE: 84
uaaggugcau cuagugcaga ua                                          22

<210> SEQ ID NO 85
<211> LENGTH: 23
<212> TYPE: RNA
<213> ORGANISM: Homo sapiens

<400> SEQUENCE: 85
ugugcaaauc uaugcaaaac uga                                         23

<210> SEQ ID NO 86
<211> LENGTH: 23
<212> TYPE: RNA
<213> ORGANISM: Homo sapiens

<400> SEQUENCE: 86
ugugcaaauc caugcaaaac uga                                         23

<210> SEQ ID NO 87
<211> LENGTH: 22
<212> TYPE: RNA
<213> ORGANISM: Homo sapiens

<400> SEQUENCE: 87
uaaagugcuu auagugcagg ua                                          22

<210> SEQ ID NO 88
<211> LENGTH: 22
```

```
<212> TYPE: RNA
<213> ORGANISM: Homo sapiens

<400> SEQUENCE: 88
uagcuuauca gacugauguu ga                                              22

<210> SEQ ID NO 89
<211> LENGTH: 22
<212> TYPE: RNA
<213> ORGANISM: Homo sapiens

<400> SEQUENCE: 89
aagcugccag uugaagaacu gu                                              22

<210> SEQ ID NO 90
<211> LENGTH: 21
<212> TYPE: RNA
<213> ORGANISM: Homo sapiens

<400> SEQUENCE: 90
aucacauugc cagggauuuc c                                               21

<210> SEQ ID NO 91
<211> LENGTH: 22
<212> TYPE: RNA
<213> ORGANISM: Homo sapiens

<400> SEQUENCE: 91
uggcucaguu cagcaggaac ag                                              22

<210> SEQ ID NO 92
<211> LENGTH: 22
<212> TYPE: RNA
<213> ORGANISM: Homo sapiens

<400> SEQUENCE: 92
cauugcacuu gucucggucu ga                                              22

<210> SEQ ID NO 93
<211> LENGTH: 22
<212> TYPE: RNA
<213> ORGANISM: Homo sapiens

<400> SEQUENCE: 93
uucaaguaau ccaggauagg cu                                              22

<210> SEQ ID NO 94
<211> LENGTH: 22
<212> TYPE: RNA
<213> ORGANISM: Homo sapiens

<400> SEQUENCE: 94
uucaaguaau ucaggauagg uu                                              22

<210> SEQ ID NO 95
<211> LENGTH: 22
<212> TYPE: RNA
<213> ORGANISM: Homo sapiens

<400> SEQUENCE: 95
uucacagugg cuaaguuccg cu                                              22

<210> SEQ ID NO 96
<211> LENGTH: 22
```

-continued

<212> TYPE: RNA
<213> ORGANISM: Homo sapiens

<400> SEQUENCE: 96
aaggagcuca cagucuauug ag                                              22

<210> SEQ ID NO 97
<211> LENGTH: 22
<212> TYPE: RNA
<213> ORGANISM: Homo sapiens

<400> SEQUENCE: 97
cuagcaccau cugaaaucgg uu                                              22

<210> SEQ ID NO 98
<211> LENGTH: 22
<212> TYPE: RNA
<213> ORGANISM: Homo sapiens

<400> SEQUENCE: 98
cuuucagucg gauguuugca gc                                              22

<210> SEQ ID NO 99
<211> LENGTH: 21
<212> TYPE: RNA
<213> ORGANISM: Homo sapiens

<400> SEQUENCE: 99
ggcaagaugc uggcauagcu g                                               21

<210> SEQ ID NO 100
<211> LENGTH: 21
<212> TYPE: RNA
<213> ORGANISM: Homo sapiens

<400> SEQUENCE: 100
uauugcacau uacuaaguug c                                               21

<210> SEQ ID NO 101
<211> LENGTH: 19
<212> TYPE: RNA
<213> ORGANISM: Homo sapiens

<400> SEQUENCE: 101
gugcauugua guugcauug                                                  19

<210> SEQ ID NO 102
<211> LENGTH: 22
<212> TYPE: RNA
<213> ORGANISM: Homo sapiens

<400> SEQUENCE: 102
uggaauguaa agaaguaugg ag                                              22

<210> SEQ ID NO 103
<211> LENGTH: 23
<212> TYPE: RNA
<213> ORGANISM: Homo sapiens

<400> SEQUENCE: 103
uggaagacua gugauuuugu ugu                                             23

<210> SEQ ID NO 104
<211> LENGTH: 23

```
<212> TYPE: RNA
<213> ORGANISM: Homo sapiens

<400> SEQUENCE: 104
ucuuugguua ucuagcugua uga                                        23

<210> SEQ ID NO 105
<211> LENGTH: 21
<212> TYPE: RNA
<213> ORGANISM: Homo sapiens

<400> SEQUENCE: 105
acccuguaga uccgaauuug u                                          21

<210> SEQ ID NO 106
<211> LENGTH: 22
<212> TYPE: RNA
<213> ORGANISM: Mus musculus

<400> SEQUENCE: 106
ugagguagua gguuguauag uu                                         22

<210> SEQ ID NO 107
<211> LENGTH: 22
<212> TYPE: RNA
<213> ORGANISM: Mus musculus

<400> SEQUENCE: 107
ugagguagua gguugugugg uu                                         22

<210> SEQ ID NO 108
<211> LENGTH: 22
<212> TYPE: RNA
<213> ORGANISM: Mus musculus

<400> SEQUENCE: 108
ugagguagua gguuguaugg uu                                         22

<210> SEQ ID NO 109
<211> LENGTH: 21
<212> TYPE: RNA
<213> ORGANISM: Mus musculus

<400> SEQUENCE: 109
agagguagua gguugcauag u                                          21

<210> SEQ ID NO 110
<211> LENGTH: 21
<212> TYPE: RNA
<213> ORGANISM: Mus musculus

<400> SEQUENCE: 110
ugagguagga gguuguauag u                                          21

<210> SEQ ID NO 111
<211> LENGTH: 22
<212> TYPE: RNA
<213> ORGANISM: Mus musculus

<400> SEQUENCE: 111
ugagguagua gauuguauag uu                                         22

<210> SEQ ID NO 112
<211> LENGTH: 22
```

```
<212> TYPE: RNA
<213> ORGANISM: Mus musculus

<400> SEQUENCE: 112
ugagguagua guuuguacag ua                                          22

<210> SEQ ID NO 113
<211> LENGTH: 22
<212> TYPE: RNA
<213> ORGANISM: Mus musculus

<400> SEQUENCE: 113
ugagguagua guguguacag uu                                          22

<210> SEQ ID NO 114
<211> LENGTH: 19
<212> TYPE: RNA
<213> ORGANISM: Mus musculus

<400> SEQUENCE: 114
ugagguagua guuugugcu                                              19

<210> SEQ ID NO 115
<211> LENGTH: 22
<212> TYPE: RNA
<213> ORGANISM: Mus musculus

<400> SEQUENCE: 115
uggaauguaa agaaguaugu aa                                          22

<210> SEQ ID NO 116
<211> LENGTH: 22
<212> TYPE: RNA
<213> ORGANISM: Mus musculus

<400> SEQUENCE: 116
uggaauguaa agaaguaugu ac                                          22

<210> SEQ ID NO 117
<211> LENGTH: 23
<212> TYPE: RNA
<213> ORGANISM: Mus musculus

<400> SEQUENCE: 117
uggaauguaa agaaguaugu auu                                         23

<210> SEQ ID NO 118
<211> LENGTH: 23
<212> TYPE: RNA
<213> ORGANISM: Mus musculus

<400> SEQUENCE: 118
ucuuugguua ucuagcugua uga                                         23

<210> SEQ ID NO 119
<211> LENGTH: 22
<212> TYPE: RNA
<213> ORGANISM: Mus musculus

<400> SEQUENCE: 119
uagcagcaca uaaugguuug ug                                          22

<210> SEQ ID NO 120
<211> LENGTH: 22
```

```
<212> TYPE: RNA
<213> ORGANISM: Mus musculus

<400> SEQUENCE: 120
uagcagcaca ucaugguuua ca                                              22

<210> SEQ ID NO 121
<211> LENGTH: 22
<212> TYPE: RNA
<213> ORGANISM: Mus musculus

<400> SEQUENCE: 121
uagcagcacg uaaauauugg cg                                              22

<210> SEQ ID NO 122
<211> LENGTH: 22
<212> TYPE: RNA
<213> ORGANISM: Mus musculus

<400> SEQUENCE: 122
uaaggugcau cuagugcaga ua                                              22

<210> SEQ ID NO 123
<211> LENGTH: 23
<212> TYPE: RNA
<213> ORGANISM: Mus musculus

<400> SEQUENCE: 123
ugugcaaauc caugcaaaac uga                                             23

<210> SEQ ID NO 124
<211> LENGTH: 23
<212> TYPE: RNA
<213> ORGANISM: Mus musculus

<400> SEQUENCE: 124
uaaagugcuu auagugcagg uag                                             23

<210> SEQ ID NO 125
<211> LENGTH: 22
<212> TYPE: RNA
<213> ORGANISM: Mus musculus

<400> SEQUENCE: 125
uagcuuauca gacugauguu ga                                              22

<210> SEQ ID NO 126
<211> LENGTH: 22
<212> TYPE: RNA
<213> ORGANISM: Mus musculus

<400> SEQUENCE: 126
aagcugccag uugaagaacu gu                                              22

<210> SEQ ID NO 127
<211> LENGTH: 21
<212> TYPE: RNA
<213> ORGANISM: Mus musculus

<400> SEQUENCE: 127
aucacauugc cagggauuuc c                                               21

<210> SEQ ID NO 128
<211> LENGTH: 23
```

```
<212> TYPE: RNA
<213> ORGANISM: Mus musculus

<400> SEQUENCE: 128
aucacauugc cagggauuac cac                                          23

<210> SEQ ID NO 129
<211> LENGTH: 22
<212> TYPE: RNA
<213> ORGANISM: Mus musculus

<400> SEQUENCE: 129
uggcucaguu cagcaggaac ag                                           22

<210> SEQ ID NO 130
<211> LENGTH: 22
<212> TYPE: RNA
<213> ORGANISM: Mus musculus

<400> SEQUENCE: 130
uucaaguaau ccaggauagg cu                                           22

<210> SEQ ID NO 131
<211> LENGTH: 22
<212> TYPE: RNA
<213> ORGANISM: Mus musculus

<400> SEQUENCE: 131
uucaaguaau ucaggauagg uu                                           22

<210> SEQ ID NO 132
<211> LENGTH: 22
<212> TYPE: RNA
<213> ORGANISM: Mus musculus

<400> SEQUENCE: 132
uucacagugg cuaaguuccg cu                                           22

<210> SEQ ID NO 133
<211> LENGTH: 20
<212> TYPE: RNA
<213> ORGANISM: Mus musculus

<400> SEQUENCE: 133
uucacagugg cuaaguucug                                              20

<210> SEQ ID NO 134
<211> LENGTH: 22
<212> TYPE: RNA
<213> ORGANISM: Mus musculus

<400> SEQUENCE: 134
cuagcaccau cugaaaucgg uu                                           22

<210> SEQ ID NO 135
<211> LENGTH: 23
<212> TYPE: RNA
<213> ORGANISM: Mus musculus

<400> SEQUENCE: 135
uagcaccauu ugaaaucagu guu                                          23

<210> SEQ ID NO 136
<211> LENGTH: 22
```

-continued

<212> TYPE: RNA
<213> ORGANISM: Mus musculus

<400> SEQUENCE: 136
uagcaccauu ugaaacggu ua                                        22

<210> SEQ ID NO 137
<211> LENGTH: 23
<212> TYPE: RNA
<213> ORGANISM: Mus musculus

<400> SEQUENCE: 137
uguaaacauc cucgacugga agc                                      23

<210> SEQ ID NO 138
<211> LENGTH: 22
<212> TYPE: RNA
<213> ORGANISM: Mus musculus

<400> SEQUENCE: 138
cuuucagucg gauguuugca gc                                       22

<210> SEQ ID NO 139
<211> LENGTH: 21
<212> TYPE: RNA
<213> ORGANISM: Mus musculus

<400> SEQUENCE: 139
uguaaacauc cuacacucag c                                        21

<210> SEQ ID NO 140
<211> LENGTH: 23
<212> TYPE: RNA
<213> ORGANISM: Mus musculus

<400> SEQUENCE: 140
uguaaacauc cuacacucuc agc                                      23

<210> SEQ ID NO 141
<211> LENGTH: 22
<212> TYPE: RNA
<213> ORGANISM: Mus musculus

<400> SEQUENCE: 141
uguaaacauc cccgacugga ag                                       22

<210> SEQ ID NO 142
<211> LENGTH: 20
<212> TYPE: RNA
<213> ORGANISM: Mus musculus

<400> SEQUENCE: 142
acccguagau ccgaucuugu                                          20

<210> SEQ ID NO 143
<211> LENGTH: 22
<212> TYPE: RNA
<213> ORGANISM: Mus musculus

<400> SEQUENCE: 143
cacccguaga accgaccuug cg                                       22

<210> SEQ ID NO 144
<211> LENGTH: 20

```
<212> TYPE: RNA
<213> ORGANISM: Mus musculus

<400> SEQUENCE: 144
uacaguacug ugauaacuga                                                    20

<210> SEQ ID NO 145
<211> LENGTH: 23
<212> TYPE: RNA
<213> ORGANISM: Mus musculus

<400> SEQUENCE: 145
uggaguguga caauguguu ugu                                                 23

<210> SEQ ID NO 146
<211> LENGTH: 23
<212> TYPE: RNA
<213> ORGANISM: Mus musculus

<400> SEQUENCE: 146
uggaguguga caauguguu uga                                                 23

<210> SEQ ID NO 147
<211> LENGTH: 22
<212> TYPE: RNA
<213> ORGANISM: Mus musculus

<400> SEQUENCE: 147
uggaguguga caauguguu ug                                                  22

<210> SEQ ID NO 148
<211> LENGTH: 21
<212> TYPE: RNA
<213> ORGANISM: Mus musculus

<400> SEQUENCE: 148
cauuauuacu uuugguacgc g                                                  21

<210> SEQ ID NO 149
<211> LENGTH: 22
<212> TYPE: RNA
<213> ORGANISM: Mus musculus

<400> SEQUENCE: 149
uuaaggcacg cggugaaugc ca                                                 22

<210> SEQ ID NO 150
<211> LENGTH: 21
<212> TYPE: RNA
<213> ORGANISM: Mus musculus

<400> SEQUENCE: 150
uuaaggcacg cgggugaaug c                                                  21

<210> SEQ ID NO 151
<211> LENGTH: 23
<212> TYPE: RNA
<213> ORGANISM: Mus musculus

<400> SEQUENCE: 151
ucccugagac ccuuuaaccu gug                                                23

<210> SEQ ID NO 152
<211> LENGTH: 22
```

```
<212> TYPE: RNA
<213> ORGANISM: Mus musculus

<400> SEQUENCE: 152
ucccugagac ccuaacuugu ga                                        22

<210> SEQ ID NO 153
<211> LENGTH: 21
<212> TYPE: RNA
<213> ORGANISM: Mus musculus

<400> SEQUENCE: 153
ucguaccgug aguaauaaug c                                         21

<210> SEQ ID NO 154
<211> LENGTH: 22
<212> TYPE: RNA
<213> ORGANISM: Mus musculus

<400> SEQUENCE: 154
ucggauccgu cugagcuugg cu                                        22

<210> SEQ ID NO 155
<211> LENGTH: 22
<212> TYPE: RNA
<213> ORGANISM: Mus musculus

<400> SEQUENCE: 155
ucacagugaa ccggucucuu uu                                        22

<210> SEQ ID NO 156
<211> LENGTH: 21
<212> TYPE: RNA
<213> ORGANISM: Mus musculus

<400> SEQUENCE: 156 cuuuuucgg ucugggcuug c                                          21

<210> SEQ ID NO 157
<211> LENGTH: 20
<212> TYPE: RNA
<213> ORGANISM: Mus musculus

<400> SEQUENCE: 157
cagugcaaug uuaaaagggc                                           20

<210> SEQ ID NO 158
<211> LENGTH: 21
<212> TYPE: RNA
<213> ORGANISM: Mus musculus

<400> SEQUENCE: 158
uaaagcuaga uaaccgaaag u                                         21

<210> SEQ ID NO 159
<211> LENGTH: 23
<212> TYPE: RNA
<213> ORGANISM: Mus musculus

<400> SEQUENCE: 159
uaacagucua cagccauggu cgu                                       23

<210> SEQ ID NO 160
<211> LENGTH: 22
```

<212> TYPE: RNA
<213> ORGANISM: Mus musculus

<400> SEQUENCE: 160 uuggucccu ucaaccagcu gu                                          22

<210> SEQ ID NO 161
<211> LENGTH: 22
<212> TYPE: RNA
<213> ORGANISM: Mus musculus

<400> SEQUENCE: 161
ugugacuggu ugaccagagg ga                                         22

<210> SEQ ID NO 162
<211> LENGTH: 24
<212> TYPE: RNA
<213> ORGANISM: Mus musculus

<400> SEQUENCE: 162
uauggcuuuu uauuccuaug ugaa                                       24

<210> SEQ ID NO 163
<211> LENGTH: 23
<212> TYPE: RNA
<213> ORGANISM: Mus musculus

<400> SEQUENCE: 163
acuccauuug uuuugaugau gga                                        23

<210> SEQ ID NO 164
<211> LENGTH: 22
<212> TYPE: RNA
<213> ORGANISM: Mus musculus

<400> SEQUENCE: 164
uauugcuuaa gaauacgcgu ag                                         22

<210> SEQ ID NO 165
<211> LENGTH: 17
<212> TYPE: RNA
<213> ORGANISM: Mus musculus

<400> SEQUENCE: 165
agcugguguu gugaauc                                               17

<210> SEQ ID NO 166
<211> LENGTH: 18
<212> TYPE: RNA
<213> ORGANISM: Mus musculus

<400> SEQUENCE: 166
ucuacagugc acgugucu                                              18

<210> SEQ ID NO 167
<211> LENGTH: 21
<212> TYPE: RNA
<213> ORGANISM: Mus musculus

<400> SEQUENCE: 167
agugguuuua cccuauggua g                                          21

<210> SEQ ID NO 168
<211> LENGTH: 21

```
<212> TYPE: RNA
<213> ORGANISM: Mus musculus

<400> SEQUENCE: 168
aacacugucu gguaaagaug g                                              21

<210> SEQ ID NO 169
<211> LENGTH: 20
<212> TYPE: RNA
<213> ORGANISM: Mus musculus

<400> SEQUENCE: 169
cauaaaguag aaagcacuac                                                20

<210> SEQ ID NO 170
<211> LENGTH: 22
<212> TYPE: RNA
<213> ORGANISM: Mus musculus

<400> SEQUENCE: 170
uguaguguuu ccuacuuuau gg                                             22

<210> SEQ ID NO 171
<211> LENGTH: 22
<212> TYPE: RNA
<213> ORGANISM: Mus musculus

<400> SEQUENCE: 171
ugagaugaag cacguagcu ca                                              22

<210> SEQ ID NO 172
<211> LENGTH: 22
<212> TYPE: RNA
<213> ORGANISM: Mus musculus

<400> SEQUENCE: 172
uacaguauag augauguacu ag                                             22

<210> SEQ ID NO 173
<211> LENGTH: 24
<212> TYPE: RNA
<213> ORGANISM: Mus musculus

<400> SEQUENCE: 173
guccaguuuu cccaggaauc ccuu                                           24

<210> SEQ ID NO 174
<211> LENGTH: 23
<212> TYPE: RNA
<213> ORGANISM: Mus musculus

<400> SEQUENCE: 174
ugagaacuga auuccauggg uuu                                            23

<210> SEQ ID NO 175
<211> LENGTH: 21
<212> TYPE: RNA
<213> ORGANISM: Mus musculus

<400> SEQUENCE: 175
guguguggaa augcuucugc c                                              21

<210> SEQ ID NO 176
<211> LENGTH: 22
```

```
<212> TYPE: RNA
<213> ORGANISM: Mus musculus

<400> SEQUENCE: 176
ucagugcacu acagaacuuu gu                                              22

<210> SEQ ID NO 177
<211> LENGTH: 22
<212> TYPE: RNA
<213> ORGANISM: Mus musculus

<400> SEQUENCE: 177
ucuggcuccg ugucuucacu cc                                              22

<210> SEQ ID NO 178
<211> LENGTH: 23
<212> TYPE: RNA
<213> ORGANISM: Mus musculus

<400> SEQUENCE: 178
ucucccaacc cuuguaccag ugu                                             23

<210> SEQ ID NO 179
<211> LENGTH: 22
<212> TYPE: RNA
<213> ORGANISM: Mus musculus

<400> SEQUENCE: 179
cuagacugag gcuccuugag gu                                              22

<210> SEQ ID NO 180
<211> LENGTH: 21
<212> TYPE: RNA
<213> ORGANISM: Mus musculus

<400> SEQUENCE: 180
ucagugcaug acagaacuug g                                               21

<210> SEQ ID NO 181
<211> LENGTH: 20
<212> TYPE: RNA
<213> ORGANISM: Mus musculus

<400> SEQUENCE: 181
uugcauaguc acaaaaguga                                                 20

<210> SEQ ID NO 182
<211> LENGTH: 22
<212> TYPE: RNA
<213> ORGANISM: Mus musculus

<400> SEQUENCE: 182
uagguuaucc guguugccuu cg                                              22

<210> SEQ ID NO 183
<211> LENGTH: 22
<212> TYPE: RNA
<213> ORGANISM: Mus musculus

<400> SEQUENCE: 183
uuaaugcuaa uugugauagg gg                                              22

<210> SEQ ID NO 184
<211> LENGTH: 23
```

```
<212> TYPE: RNA
<213> ORGANISM: Mus musculus

<400> SEQUENCE: 184
aacauucaac gcugucggug agu                                           23

<210> SEQ ID NO 185
<211> LENGTH: 22
<212> TYPE: RNA
<213> ORGANISM: Mus musculus

<400> SEQUENCE: 185
uuuggcaaug guagaacuca ca                                            22

<210> SEQ ID NO 186
<211> LENGTH: 23
<212> TYPE: RNA
<213> ORGANISM: Mus musculus

<400> SEQUENCE: 186
uauggcacug guagaauuca cug                                           23

<210> SEQ ID NO 187
<211> LENGTH: 22
<212> TYPE: RNA
<213> ORGANISM: Unknown
<220> FEATURE:
<223> OTHER INFORMATION: Sequence isolated from both Homo sapiens
      (Human osteocaroma cells) and Mus musculus

<400> SEQUENCE: 187
cuuuuugcgg ucugggcuug uu                                            22

<210> SEQ ID NO 188
<211> LENGTH: 22
<212> TYPE: RNA
<213> ORGANISM: Mus musculus

<400> SEQUENCE: 188
uggacggaga acugauaagg gu                                            22

<210> SEQ ID NO 189
<211> LENGTH: 18
<212> TYPE: RNA
<213> ORGANISM: Mus musculus

<400> SEQUENCE: 189
uggagagaaa ggcaguuc                                                 18

<210> SEQ ID NO 190
<211> LENGTH: 23
<212> TYPE: RNA
<213> ORGANISM: Unknown
<220> FEATURE:
<223> OTHER INFORMATION: Sequence isolated from both Homo sapiens
      (Human osteocaroma cells) and Mus musculus

<400> SEQUENCE: 190
caaagaauuc uccuuuuggg cuu                                           23

<210> SEQ ID NO 191
<211> LENGTH: 22
<212> TYPE: RNA
<213> ORGANISM: Mus musculus

<400> SEQUENCE: 191
```
ucgugucuug uguugcagcc gg 22

<210> SEQ ID NO 192
<211> LENGTH: 21
<212> TYPE: RNA
<213> ORGANISM: Mus musculus

<400> SEQUENCE: 192
uaacacuguc ugguaacgau g 21

<210> SEQ ID NO 193
<211> LENGTH: 22
<212> TYPE: RNA
<213> ORGANISM: Mus musculus

<400> SEQUENCE: 193
caucccuugc augguggagg gu 22

<210> SEQ ID NO 194
<211> LENGTH: 23
<212> TYPE: RNA
<213> ORGANISM: Mus musculus

<400> SEQUENCE: 194
gugccuacug agcugacauc agu 23

<210> SEQ ID NO 195
<211> LENGTH: 22
<212> TYPE: RNA
<213> ORGANISM: Mus musculus

<400> SEQUENCE: 195
ugauauguuu gauauauuag gu 22

<210> SEQ ID NO 196
<211> LENGTH: 22
<212> TYPE: RNA
<213> ORGANISM: Mus musculus

<400> SEQUENCE: 196
caacggaauc ccaaaagcag cu 22

<210> SEQ ID NO 197
<211> LENGTH: 18
<212> TYPE: RNA
<213> ORGANISM: Mus musculus

<400> SEQUENCE: 197
cugaccuaug aauugaca 18

<210> SEQ ID NO 198
<211> LENGTH: 22
<212> TYPE: RNA
<213> ORGANISM: Mus musculus

<400> SEQUENCE: 198
uaccacaggg uagaaccacg ga 22

<210> SEQ ID NO 199
<211> LENGTH: 21
<212> TYPE: RNA
<213> ORGANISM: Mus musculus

<400> SEQUENCE: 199
aacuggccua caaagucccca g					21

<210> SEQ ID NO 200
<211> LENGTH: 22
<212> TYPE: RNA
<213> ORGANISM: Mus musculus

<400> SEQUENCE: 200
uguaacagca acuccaugug ga					22

<210> SEQ ID NO 201
<211> LENGTH: 21
<212> TYPE: RNA
<213> ORGANISM: Mus musculus

<400> SEQUENCE: 201
uagcagcaca gaaauauugg c					21

<210> SEQ ID NO 202
<211> LENGTH: 21
<212> TYPE: RNA
<213> ORGANISM: Homo sapiens

<400> SEQUENCE: 202
uagguaguuu cauguuguug g					21

<210> SEQ ID NO 203
<211> LENGTH: 22
<212> TYPE: RNA
<213> ORGANISM: Homo sapiens

<400> SEQUENCE: 203
uucaccaccu ucuccaccca gc					22

<210> SEQ ID NO 204
<211> LENGTH: 19
<212> TYPE: RNA
<213> ORGANISM: Homo sapiens

<400> SEQUENCE: 204
gguccagagg ggagauagg					19

<210> SEQ ID NO 205
<211> LENGTH: 22
<212> TYPE: RNA
<213> ORGANISM: Homo sapiens

<400> SEQUENCE: 205
cccaguguuc agacuaccug uu					22

<210> SEQ ID NO 206
<211> LENGTH: 23
<212> TYPE: RNA
<213> ORGANISM: Mus musculus

<400> SEQUENCE: 206
uaauacugcc ugguaaugau gac				23

<210> SEQ ID NO 207
<211> LENGTH: 21
<212> TYPE: RNA
<213> ORGANISM: Mus musculus

<400> SEQUENCE: 207
uacucaguaa ggcauuguuc u                                          21

<210> SEQ ID NO 208
<211> LENGTH: 22
<212> TYPE: RNA
<213> ORGANISM: Mus musculus

<400> SEQUENCE: 208
agagguauag cgcaugggaa ga                                         22

<210> SEQ ID NO 209
<211> LENGTH: 21
<212> TYPE: RNA
<213> ORGANISM: Mus musculus

<400> SEQUENCE: 209
ugaaauguuu aggaccacua g                                          21

<210> SEQ ID NO 210
<211> LENGTH: 23
<212> TYPE: RNA
<213> ORGANISM: Mus musculus

<400> SEQUENCE: 210
uucccuuugu cauccuaugc cug                                        23

<210> SEQ ID NO 211
<211> LENGTH: 22
<212> TYPE: RNA
<213> ORGANISM: Mus musculus

<400> SEQUENCE: 211
uccuucauuc caccggaguc ug                                         22

<210> SEQ ID NO 212
<211> LENGTH: 23
<212> TYPE: RNA
<213> ORGANISM: Mus musculus

<400> SEQUENCE: 212
gugaaauguu uaggaccacu aga                                        23

<210> SEQ ID NO 213
<211> LENGTH: 22
<212> TYPE: RNA
<213> ORGANISM: Mus musculus

<400> SEQUENCE: 213
uggaauguaa ggaagugugu gg                                         22

<210> SEQ ID NO 214
<211> LENGTH: 22
<212> TYPE: RNA
<213> ORGANISM: Mus musculus

<400> SEQUENCE: 214
uacaguaguc ugcacauugg uu                                         22

<210> SEQ ID NO 215
<211> LENGTH: 22
<212> TYPE: RNA
<213> ORGANISM: Mus musculus

<400> SEQUENCE: 215

```
cccuguagaa ccgaauuugu gu                                              22

<210> SEQ ID NO 216
<211> LENGTH: 24
<212> TYPE: RNA
<213> ORGANISM: Mus musculus

<400> SEQUENCE: 216
aacccguaga uccgaacuug ugaa                                            24

<210> SEQ ID NO 217
<211> LENGTH: 23
<212> TYPE: RNA
<213> ORGANISM: Mus musculus

<400> SEQUENCE: 217
gcuucuccug gcucuccucc cuc                                             23

<210> SEQ ID NO 218
<211> LENGTH: 91
<212> TYPE: RNA
<213> ORGANISM: Drosophila melanogaster
<220> FEATURE:
<221> NAME/KEY: misc_RNA
<222> LOCATION: (1)..(91)
<223> OTHER INFORMATION: predicted precursor structure: mir-1, 5' to 3'
      sequence

<400> SEQUENCE: 218
uucagccuuu gagaguucca ugcuuccuug cauucaauag uuauauucaa gcauauggaa     60
uguaaagaag uauggagcga aaucuggcga g                                    91

<210> SEQ ID NO 219
<211> LENGTH: 76
<212> TYPE: RNA
<213> ORGANISM: Drosophila melanogaster
<220> FEATURE:
<221> NAME/KEY: misc_RNA
<222> LOCATION: (1)..(76)
<223> OTHER INFORMATION: predicted precursor structure: mir-2a-1, 5' to
      3' sequence

<400> SEQUENCE: 219
gcugggcucu caaagugguu gugaaaugca uuccgcuuu gcgcggcaua ucacagccag      60
cuuugaugag cuuagc                                                     76

<210> SEQ ID NO 220
<211> LENGTH: 72
<212> TYPE: RNA
<213> ORGANISM: Drosophila melanogaster
<220> FEATURE:
<221> NAME/KEY: misc_RNA
<222> LOCATION: (1)..(72)
<223> OTHER INFORMATION: predicted precursor structure: mir-2a-2, 5' to
      3' sequence

<400> SEQUENCE: 220
aucuaagccu caucaagugg uugugauaug gauacccaac gcauaucaca gccagcuuug     60
augagcuagg au                                                         72

<210> SEQ ID NO 221
<211> LENGTH: 77
<212> TYPE: RNA
<213> ORGANISM: Drosophila melanogaster
<220> FEATURE:
```

```
<221> NAME/KEY: misc_RNA
<222> LOCATION: (1)..(77)
<223> OTHER INFORMATION: predicted precursor structure: mir-2b-1, 5' to
      3' sequence

<400> SEQUENCE: 221
cuucaacugu cuucaaagug gcagugacau guugucaaca auauucauau cacagccagc      60
uuugaggagc guugcgg                                                    77

<210> SEQ ID NO 222
<211> LENGTH: 83
<212> TYPE: RNA
<213> ORGANISM: Drosophila melanogaster
<220> FEATURE:
<221> NAME/KEY: misc_RNA
<222> LOCATION: (1)..(83)
<223> OTHER INFORMATION: predicted precursor structure: mir-2b-2, 5' to
      3' sequence

<400> SEQUENCE: 222
uugugucauu cuucaaagug guugugaaau guuugccuuu uuaugccuau ucauaucaca      60
gccagcuuug aggagcgacg cga                                             83

<210> SEQ ID NO 223
<211> LENGTH: 69
<212> TYPE: RNA
<213> ORGANISM: Drosophila melanogaster
<220> FEATURE:
<221> NAME/KEY: misc_RNA
<222> LOCATION: (1)..(69)
<223> OTHER INFORMATION: predicted precursor structure: mir-3, 5' to 3'
      sequence

<400> SEQUENCE: 223
gauccuggga ugcaucuugu gcaguuaugu uucaaucuca caucacuggg caaagugugu      60
cucaagauc                                                             69

<210> SEQ ID NO 224
<211> LENGTH: 82
<212> TYPE: RNA
<213> ORGANISM: Drosophila melanogaster
<220> FEATURE:
<221> NAME/KEY: misc_RNA
<222> LOCATION: (1)..(82)
<223> OTHER INFORMATION: predicted precursor structure: mir-4, 5' to 3'
      sequence

<400> SEQUENCE: 224
uugcaauuag uuucuuuggu cguccagccu uagggugauu uuccgguca uaaagcuaga      60 caaccauuga aguucguugu gg                                              82

<210> SEQ ID NO 225
<211> LENGTH: 69
<212> TYPE: RNA
<213> ORGANISM: Drosophila melanogaster
<220> FEATURE:
<221> NAME/KEY: misc_RNA
<222> LOCATION: (1)..(69)
<223> OTHER INFORMATION: predicted precursor structure: mir-5, 5' to 3'
      sequence

<400> SEQUENCE: 225
gcuaaaagga acgaucguug ugauaugagu uguuccuaa cauaucacag ugauuuuccu       60
uuauaacgc                                                             69
```

```
<210> SEQ ID NO 226
<211> LENGTH: 81
<212> TYPE: RNA
<213> ORGANISM: Drosophila melanogaster
<220> FEATURE:
<221> NAME/KEY: misc_RNA
<222> LOCATION: (1)..(81)
<223> OTHER INFORMATION: predicted precursor structure: mir-6-1, 5' to
      3' sequence

<400> SEQUENCE: 226
uuuaauguag agggaauagu ugcugugcug uaaguuaaua uaccauaucu auaucacagg      60
gcuguucuuu uuguaccuaa a                                                81

<210> SEQ ID NO 227
<211> LENGTH: 74
<212> TYPE: RNA
<213> ORGANISM: Drosophila melanogaster
<220> FEATURE:
<221> NAME/KEY: misc_RNA
<222> LOCATION: (1)..(74)
<223> OTHER INFORMATION: predicted precursor structure: mir-6-2, 5' to
      3' sequence

<400> SEQUENCE: 227
uaacccaagg gaacuucugc ugcugauaua uuauugaaaa acuacuauau cacaguggcu      60
guucuuuuug guug                                                        74

<210> SEQ ID NO 228
<211> LENGTH: 79
<212> TYPE: RNA
<213> ORGANISM: Drosophila melanogaster
<220> FEATURE:
<221> NAME/KEY: misc_RNA
<222> LOCATION: (1)..(79)
<223> OTHER INFORMATION: predicted precursor structure: mir-6-3, 5' to
      3' sequence

<400> SEQUENCE: 228
caaaaagaag ggaacgguug cugaugaugu aguuugaaac ucucacaauu uauaucacag      60
uggcuguucu uuuuguuug                                                   79

<210> SEQ ID NO 229
<211> LENGTH: 88
<212> TYPE: RNA
<213> ORGANISM: Drosophila melanogaster
<220> FEATURE:
<221> NAME/KEY: misc_RNA
<222> LOCATION: (1)..(88)
<223> OTHER INFORMATION: predicted precursor structure: mir-7, 5' to 3'
      sequence

<400> SEQUENCE: 229
gagugcauuc cguauggaag acuagugauu uuguuguuug gucuuuggua auaacaauaa      60
aucccuuguc uucuuacggc gugcauuu                                         88

<210> SEQ ID NO 230
<211> LENGTH: 87
<212> TYPE: RNA
<213> ORGANISM: Drosophila melanogaster
<220> FEATURE:
<221> NAME/KEY: misc_RNA
<222> LOCATION: (1)..(87)
<223> OTHER INFORMATION: predicted precursor structure: mir-8, 5' to 3'
      sequence

<400> SEQUENCE: 230
```

```
aaggacaucu guucacaucu uaccgggcag cauuagaucc uuuuuauaac ucuaauacug    60
ucagguaaag augucguccg uguccuu                                       87
```

<210> SEQ ID NO 231
<211> LENGTH: 78
<212> TYPE: RNA
<213> ORGANISM: Drosophila melanogaster
<220> FEATURE:
<221> NAME/KEY: misc_RNA
<222> LOCATION: (1)..(78)
<223> OTHER INFORMATION: predicted precursor structure: mir-9, 5' to 3'
      sequence

<400> SEQUENCE: 231

```
gcuauguugu cuuugguuau cuagcuguau gagugauaaa uaacgucaua aagcuagcuu    60
accgaaguua auauuagc                                                 78
```

<210> SEQ ID NO 232
<211> LENGTH: 77
<212> TYPE: RNA
<213> ORGANISM: Drosophila melanogaster
<220> FEATURE:
<221> NAME/KEY: misc_RNA
<222> LOCATION: (1)..(77)
<223> OTHER INFORMATION: predicted precursor structure: mir-10, 5' to 3'
      sequence

<400> SEQUENCE: 232

```
ccacgucuac ccuguagauc cgaauuuguu uuauacuagc uuuaaggaca aauucgguuc    60
uagagagguu ugugugg                                                  77
```

<210> SEQ ID NO 233
<211> LENGTH: 75
<212> TYPE: RNA
<213> ORGANISM: Drosophila melanogaster
<220> FEATURE:
<221> NAME/KEY: misc_RNA
<222> LOCATION: (1)..(75)
<223> OTHER INFORMATION: predicted precursor structure: mir-11, 5' to 3'
      sequence

<400> SEQUENCE: 233

```
gcacuuguca agaacuuucu cugugacccg cguguacuua aaagccgcau cacagucuga    60
guucuugcug agugc                                                    75
```

<210> SEQ ID NO 234
<211> LENGTH: 74
<212> TYPE: RNA
<213> ORGANISM: Drosophila melanogaster
<220> FEATURE:
<221> NAME/KEY: misc_RNA
<222> LOCATION: (1)..(74)
<223> OTHER INFORMATION: predicted precursor structure: mir-12, 5' to 3'
      sequence

<400> SEQUENCE: 234

```
uacgguugag uauuacauca gguacuggug ugccuuaaau ccaacaacca guacuuaugu    60
cauacuacgc cgug                                                     74
```

<210> SEQ ID NO 235
<211> LENGTH: 75
<212> TYPE: RNA
<213> ORGANISM: Drosophila melanogaster
<220> FEATURE:
<221> NAME/KEY: misc_RNA
<222> LOCATION: (1)..(75)

```
<223> OTHER INFORMATION: predicted precursor structure: mir-13a, 5' to
      3' sequence

<400> SEQUENCE: 235
uacguaacuc cucaaagggu ugugaaaugu cgacuauuau cuacucauau cacagccauu    60
uugaugaguu ucgug                                                    75

<210> SEQ ID NO 236
<211> LENGTH: 68
<212> TYPE: RNA
<213> ORGANISM: Drosophila melanogaster
<220> FEATURE:
<221> NAME/KEY: misc_RNA
<222> LOCATION: (1)..(68)
<223> OTHER INFORMATION: predicted precursor structure: mir-13b-1, 5'
      to 3' sequence

<400> SEQUENCE: 236
ccaugucguu aaaauguuug ugaacuuaug uauucacaau cauaucacag ccauuuugac    60
gaguuugg                                                            68

<210> SEQ ID NO 237
<211> LENGTH: 70
<212> TYPE: RNA
<213> ORGANISM: Drosophila melanogaster
<220> FEATURE:
<221> NAME/KEY: misc_RNA
<222> LOCATION: (1)..(70)
<223> OTHER INFORMATION: predicted precursor structure: mir-13b-2, 5'
      to 3' sequence

<400> SEQUENCE: 237
uauuaacgcg ucaaaaugac ugugagcuau guggauuuga cuucauauca cagccauuuu    60
gacgaguuug                                                          70

<210> SEQ ID NO 238
<211> LENGTH: 65
<212> TYPE: RNA
<213> ORGANISM: Drosophila melanogaster
<220> FEATURE:
<221> NAME/KEY: misc_RNA
<222> LOCATION: (1)..(65)
<223> OTHER INFORMATION: predicted precursor structure: mir-14, 5' to
      3' sequence

<400> SEQUENCE: 238
ugugggagcg agacguggga cucacugugc uuauuaaaua gucagcuuug uuucucucuc    60
cuaua                                                               65

<210> SEQ ID NO 239
<211> LENGTH: 80
<212> TYPE: RNA
<213> ORGANISM: Homo sapiens
<220> FEATURE:
<221> NAME/KEY: misc_RNA
<222> LOCATION: (1)..(80)
<223> OTHER INFORMATION: predicted precursor structure: let-7a-1, 5' to
      3' sequence

<400> SEQUENCE: 239
ugggaugagg uaguagguug uauaguuuua gggucacacc caccacuggg agauaacuau    60
acaaucuacu gucuuuccua                                               80

<210> SEQ ID NO 240
<211> LENGTH: 72
```

```
-continued

<212> TYPE: RNA
<213> ORGANISM: Homo sapiens
<220> FEATURE:
<221> NAME/KEY: misc_RNA
<222> LOCATION: (1)..(72)
<223> OTHER INFORMATION: predicted precursor structure: let-7a-2, 5' to
      3' sequence

<400> SEQUENCE: 240
agguugaggu aguagguugu auaguuuaga auuacaucaa gggagauaac uguacagccu    60
ccuagcuuuc cu                                                       72

<210> SEQ ID NO 241
<211> LENGTH: 74
<212> TYPE: RNA
<213> ORGANISM: Homo sapiens
<220> FEATURE:
<221> NAME/KEY: misc_RNA
<222> LOCATION: (1)..(74)
<223> OTHER INFORMATION: predicted precursor structure: let-7a-3, 5' to
      3' sequence

<400> SEQUENCE: 241
gggugaggua guagguugua uaguuuggggg cucugcccug cuaugggaua acauacaau   60 cuacugucuu uccu                                                    74

<210> SEQ ID NO 242
<211> LENGTH: 83
<212> TYPE: RNA
<213> ORGANISM: Homo sapiens
<220> FEATURE:
<221> NAME/KEY: misc_RNA
<222> LOCATION: (1)..(83)
<223> OTHER INFORMATION: predicted precursor structure: let-7b, 5' to
      3' sequence

<400> SEQUENCE: 242
cggggugagg uaguagguug ugugguuuca gggcagugau guugcccuc ggaagauaac    60 uauacaaccu acugccuucc cug                                           83

<210> SEQ ID NO 243
<211> LENGTH: 85
<212> TYPE: RNA
<213> ORGANISM: Homo sapiens
<220> FEATURE:
<221> NAME/KEY: misc_RNA
<222> LOCATION: (1)..(85)
<223> OTHER INFORMATION: predicted precursor structure: let-7c, 5' to
      3' sequence

<400> SEQUENCE: 243
gcauccgggu ugagguagua gguuguaugg uuuagaguua cacccugggg aguuaacugu    60
acaaccuucu agcuuuccuu ggagc                                         85

<210> SEQ ID NO 244
<211> LENGTH: 87
<212> TYPE: RNA
<213> ORGANISM: Homo sapiens
<220> FEATURE:
<221> NAME/KEY: misc_RNA
<222> LOCATION: (1)..(87)
<223> OTHER INFORMATION: predicted precursor structure: let-7d, 5' to
      3' sequence

<400> SEQUENCE: 244
ccuaggaaga gguaguaggu ugcauaguuu uagggcaggg auuuugccca caaggaggua    60
```

```
acuauacgac cugcugccuu ucuuagg                                          87
```

<210> SEQ ID NO 245
<211> LENGTH: 79
<212> TYPE: RNA
<213> ORGANISM: Homo sapiens
<220> FEATURE:
<221> NAME/KEY: misc_RNA
<222> LOCATION: (1)..(79)
<223> OTHER INFORMATION: predicted precursor structure: let-7e, 5' to
      3' sequence

<400> SEQUENCE: 245

```
cccgggcuga gguaggaggu uguauaguug aggaggacac ccaaggagau cacuauacgg      60
ccuccuagcu uuccccagg                                                   79
```

<210> SEQ ID NO 246
<211> LENGTH: 87
<212> TYPE: RNA
<213> ORGANISM: Homo sapiens
<220> FEATURE:
<221> NAME/KEY: misc_RNA
<222> LOCATION: (1)..(87)
<223> OTHER INFORMATION: predicted precursor structure: let-7f-1, 5' to
      3' sequence

<400> SEQUENCE: 246

```
ucagagugag guaguagauu guauaguugu ggguaguga uuuuacccug uucaggagau        60
aacuauacaa ucuauugccu ucccuga                                          87
```

<210> SEQ ID NO 247
<211> LENGTH: 85
<212> TYPE: RNA
<213> ORGANISM: Homo sapiens
<220> FEATURE:
<221> NAME/KEY: misc_RNA
<222> LOCATION: (1)..(85)
<223> OTHER INFORMATION: predicted precursor structure: let-7f-2, 5' to
      3' sequence

<400> SEQUENCE: 247

```
cugugggaug agguaguaga uuguauaguu uuagggucau accccaucuu ggagauaacu      60
auacagucua cugucuuucc cacgg                                            85
```

<210> SEQ ID NO 248
<211> LENGTH: 83
<212> TYPE: RNA
<213> ORGANISM: Homo sapiens
<220> FEATURE:
<221> NAME/KEY: misc_RNA
<222> LOCATION: (1)..(83)
<223> OTHER INFORMATION: predicted precursor structure: mir-15, 5' to
      3' sequence

<400> SEQUENCE: 248

```
ccuuggagua aaguagcagc acauaauggu uuguggauuu ugaaaaggug caggccauau      60
ugugcugccu caaaaauaca agg                                              83
```

<210> SEQ ID NO 249
<211> LENGTH: 89
<212> TYPE: RNA
<213> ORGANISM: Homo sapiens
<220> FEATURE:
<221> NAME/KEY: misc_RNA
<222> LOCATION: (1)..(89)
<223> OTHER INFORMATION: predicted precursor structure: mir-16, 5' to
      3' sequence

```
<400> SEQUENCE: 249
gucagcagug ccuuagcagc acguaaauau uggcguuaag auucuaaaau uaucuccagu      60
auuaacugug cugcugaagu aagguugac                                       89

<210> SEQ ID NO 250
<211> LENGTH: 84
<212> TYPE: RNA
<213> ORGANISM: Homo sapiens
<220> FEATURE:
<221> NAME/KEY: misc_RNA
<222> LOCATION: (1)..(84)
<223> OTHER INFORMATION: predicted precursor structure: mir-17, 5' to
      3' sequence

<400> SEQUENCE: 250
gucagaauaa ugucaaagug cuuacagugc agguagugau augugcaucu acugcaguga     60
aggcacuugu agcauuaugg ugac                                            84

<210> SEQ ID NO 251
<211> LENGTH: 71
<212> TYPE: RNA
<213> ORGANISM: Homo sapiens
<220> FEATURE:
<221> NAME/KEY: misc_RNA
<222> LOCATION: (1)..(71)
<223> OTHER INFORMATION: predicted precursor structure: mir-18, 5' to
      3' sequence

<400> SEQUENCE: 251
uguucuaagg ugcaucuagu gcagauagug aaguagauua gcaucuacug cccuaagugc     60
uccuucuggc a                                                          71

<210> SEQ ID NO 252
<211> LENGTH: 82
<212> TYPE: RNA
<213> ORGANISM: Homo sapiens
<220> FEATURE:
<221> NAME/KEY: misc_RNA
<222> LOCATION: (1)..(82)
<223> OTHER INFORMATION: predicted precursor structure: mir-19a, 5' to
      3' sequence

<400> SEQUENCE: 252
gcaguccucu guuaguuuug cauaguugca cuacaagaag aauguaguug ugcaaaucua     60
ugcaaaacug augguggccu gc                                              82

<210> SEQ ID NO 253
<211> LENGTH: 87
<212> TYPE: RNA
<213> ORGANISM: Homo sapiens
<220> FEATURE:
<221> NAME/KEY: misc_RNA
<222> LOCATION: (1)..(87)
<223> OTHER INFORMATION: predicted precursor structure: mir-19b-1, 5'
      to 3' sequence

<400> SEQUENCE: 253
cacuguucua ugguuaguuu ugcagguuug cauccagcug ugugauauuc ugcugugcaa     60
auccaugcaa aacugacugu gguagug                                         87

<210> SEQ ID NO 254
<211> LENGTH: 96
<212> TYPE: RNA
<213> ORGANISM: Homo sapiens
```

```
<220> FEATURE:
<221> NAME/KEY: misc_RNA
<222> LOCATION: (1)..(96)
<223> OTHER INFORMATION: predicted precursor structure: 19b-2, 5' to 3'
       sequence

<400> SEQUENCE: 254
acauugcuac uuacaauuag uuuugcaggu uugcauuuca gcguauauau guauaugugg      60
cugugcaaau ccaugcaaaa cugauuguga uaaugu                                96

<210> SEQ ID NO 255
<211> LENGTH: 71
<212> TYPE: RNA
<213> ORGANISM: Homo sapiens
<220> FEATURE:
<221> NAME/KEY: misc_RNA
<222> LOCATION: (1)..(71)
<223> OTHER INFORMATION: predicted precursor structure: mir-20, 5' to
       3' sequence

<400> SEQUENCE: 255
guagcacuaa agugcuuaua gugcagguag uguuuaguua ucuacugcau uaugagcacu      60
uaaaguacug c                                                          71

<210> SEQ ID NO 256
<211> LENGTH: 72
<212> TYPE: RNA
<213> ORGANISM: Homo sapiens
<220> FEATURE:
<221> NAME/KEY: misc_RNA
<222> LOCATION: (1)..(72)
<223> OTHER INFORMATION: predicted precursor structure: mir-21, 5' to
       3' sequence

<400> SEQUENCE: 256
ugucggguag cuuaucagac ugauguugac uguugaaucu cauggcaaca ccagucgaug      60
ggcugucuga ca                                                         72

<210> SEQ ID NO 257
<211> LENGTH: 84
<212> TYPE: RNA
<213> ORGANISM: Homo sapiens
<220> FEATURE:
<221> NAME/KEY: misc_RNA
<222> LOCATION: (1)..(84)
<223> OTHER INFORMATION: predicted precursor structure: mir-22, 5' to
       3' sequence

<400> SEQUENCE: 257
ggcugagccg caguaguucu ucaguggcaa gcuuuauguc cugacccagc uaaagcugcc      60
aguugaagaa cuguugcccu cugc                                            84

<210> SEQ ID NO 258
<211> LENGTH: 73
<212> TYPE: RNA
<213> ORGANISM: Homo sapiens
<220> FEATURE:
<221> NAME/KEY: misc_RNA
<222> LOCATION: (1)..(73)
<223> OTHER INFORMATION: predicted precursor structure: mir-23, 5' to
       3' sequence

<400> SEQUENCE: 258
ggccggcugg gguuccuggg gaugggauuu gcuuccuguc acaaaucaca uugccaggga      60
uuuccaaccg acc                                                        73
```

-continued

```
<210> SEQ ID NO 259
<211> LENGTH: 68
<212> TYPE: RNA
<213> ORGANISM: Homo sapiens
<220> FEATURE:
<221> NAME/KEY: misc_RNA
<222> LOCATION: (1)..(68)
<223> OTHER INFORMATION: predicted precursor structure: mir-24-1, 5' to
      3' sequence

<400> SEQUENCE: 259
cuccggugcc uacugagcug auaucaguuc ucauuuuaca cacuggcuca guucagcagg    60
aacaggag                                                              68

<210> SEQ ID NO 260
<211> LENGTH: 73
<212> TYPE: RNA
<213> ORGANISM: Homo sapiens
<220> FEATURE:
<221> NAME/KEY: misc_RNA
<222> LOCATION: (1)..(73)
<223> OTHER INFORMATION: predicted precursor structure: mir-24-2, 5' to
      3' sequence

<400> SEQUENCE: 260
cucugccucc cgugccuacu gagcugaaac acaguugguu uguguacacu ggcucaguuc    60
agcaggaaca ggg                                                        73

<210> SEQ ID NO 261
<211> LENGTH: 84
<212> TYPE: RNA
<213> ORGANISM: Homo sapiens
<220> FEATURE:
<221> NAME/KEY: misc_RNA
<222> LOCATION: (1)..(84)
<223> OTHER INFORMATION: predicted precursor structure: mir-25, 5' to
      3' sequence

<400> SEQUENCE: 261
ggccaguguu gagaggcgga gacuugggca auugcuggac gcugcccugg gcauugcacu    60
ugucucgguc ugacagugcc ggcc                                            84

<210> SEQ ID NO 262
<211> LENGTH: 89
<212> TYPE: RNA
<213> ORGANISM: Homo sapiens
<220> FEATURE:
<221> NAME/KEY: misc_RNA
<222> LOCATION: (1)..(89)
<223> OTHER INFORMATION: predicted precursor structure: mir-26a, 5' to
      3' sequence

<400> SEQUENCE: 262
aggccguggc cucguucaag uaauccagga uaggcugugc aggucccaau gggccuauuc    60
uugguuacuu gcacggggac gcgggccuu                                       89

<210> SEQ ID NO 263
<211> LENGTH: 77
<212> TYPE: RNA
<213> ORGANISM: Homo sapiens
<220> FEATURE:
<221> NAME/KEY: misc_RNA
<222> LOCATION: (1)..(77)
<223> OTHER INFORMATION: predicted precursor structure: mir-26b, 5' to
      3' sequence

<400> SEQUENCE: 263
```

```
ccgggaccca guucaaguaa uucaggauag guugugugcu guccagccug uucuccauua    60
cuuggcucgg ggaccgg                                                  77

<210> SEQ ID NO 264
<211> LENGTH: 78
<212> TYPE: RNA
<213> ORGANISM: Homo sapiens
<220> FEATURE:
<221> NAME/KEY: misc_RNA
<222> LOCATION: (1)..(78)
<223> OTHER INFORMATION: predicted precursor structure: mir-27, 5' to
      3' sequence

<400> SEQUENCE: 264
cugaggagca gggcuuagcu gcuugugagc agguccaca ccaagucgug uucacagugg    60
cuaaguuccg cccccccag                                                78

<210> SEQ ID NO 265
<211> LENGTH: 86
<212> TYPE: RNA
<213> ORGANISM: Homo sapiens
<220> FEATURE:
<221> NAME/KEY: misc_RNA
<222> LOCATION: (1)..(86)
<223> OTHER INFORMATION: predicted precursor structure: mir-28, 5' to
      3' sequence

<400> SEQUENCE: 265
gguccuugcc cucaaggagc ucacagucua uugaguuacc uuucugacuu ucccacuaga    60
uugugagcuc cuggagggca ggcacu                                        86

<210> SEQ ID NO 266
<211> LENGTH: 64
<212> TYPE: RNA
<213> ORGANISM: Homo sapiens
<220> FEATURE:
<221> NAME/KEY: misc_RNA
<222> LOCATION: (1)..(64)
<223> OTHER INFORMATION: predicted precursor structure: mir-29, 5' to
      3' sequence

<400> SEQUENCE: 266
augacugauu ucuuuuggug uucagaguca auauaauuuu cuagcaccau cugaaaucgg    60
uuau                                                                64

<210> SEQ ID NO 267
<211> LENGTH: 71
<212> TYPE: RNA
<213> ORGANISM: Homo sapiens
<220> FEATURE:
<221> NAME/KEY: misc_RNA
<222> LOCATION: (1)..(71)
<223> OTHER INFORMATION: predicted precursor structure: mir-30, 5' to
      3' sequence

<400> SEQUENCE: 267
gcgacuguaa acauccucga cuggaagcug ugaagccaca gaugggcuuu cagucggaug    60
uuugcagcug c                                                        71

<210> SEQ ID NO 268
<211> LENGTH: 71
<212> TYPE: RNA
<213> ORGANISM: Homo sapiens
<220> FEATURE:
<221> NAME/KEY: misc_RNA
```

-continued

```
<222> LOCATION: (1)..(71)
<223> OTHER INFORMATION: predicted precursor structure: mir-31, 5' to
      3' sequence

<400> SEQUENCE: 268
ggagaggagg caagaugcug gcauagcugu ugaacuggga accugcuaug ccaacauauu    60
gccaucuuuc c                                                         71

<210> SEQ ID NO 269
<211> LENGTH: 70
<212> TYPE: RNA
<213> ORGANISM: Homo sapiens
<220> FEATURE:
<221> NAME/KEY: misc_RNA
<222> LOCATION: (1)..(70)
<223> OTHER INFORMATION: predicted precursor structure: mir-32, 5' to
      3' sequence

<400> SEQUENCE: 269
ggagauauug cacauuacua aguugcaugu ugucacggcc ucaaugcaau uuagugugug    60
ugauauuuuc                                                           70

<210> SEQ ID NO 270
<211> LENGTH: 69
<212> TYPE: RNA
<213> ORGANISM: Homo sapiens
<220> FEATURE:
<221> NAME/KEY: misc_RNA
<222> LOCATION: (1)..(69)
<223> OTHER INFORMATION: predicted precurso structure: mir-33, 5' to
      3' sequence

<400> SEQUENCE: 270
cuguggugca uguaguugc auugcauguu cugguggguac ccaugcaaug uuccacagu    60 gcaucacag                                                            69

<210> SEQ ID NO 271
<211> LENGTH: 90
<212> TYPE: RNA
<213> ORGANISM: Mus musculus
<220> FEATURE:
<221> NAME/KEY: misc_RNA
<222> LOCATION: (1)..(90)
<223> OTHER INFORMATION: predicted precursor structure: let-7a-1, 5' to
      3' sequence

<400> SEQUENCE: 271
cacuguggga ugagguagua gguuguauag uuuuagggguc acacccacca cugggagaua    60
acuauacaau cuacugucuu uccuaacgug                                     90

<210> SEQ ID NO 272
<211> LENGTH: 72
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: let-7a-2, 5' to
      3' sequence

<400> SEQUENCE: 272
agguugaggu aguagguugu auaguuuaga auuacaucaa gggagauaac uguacagccu    60
ccuagcuuuc cu                                                        72

<210> SEQ ID NO 273
```

```
<211> LENGTH: 74
<212> TYPE: RNA
<213> ORGANISM: Mus musculus
<220> FEATURE:
<221> NAME/KEY: misc_RNA
<222> LOCATION: (1)..(74)
<223> OTHER INFORMATION: predicted precursor structure: let-7a-3, 5' to
      3' sequence

<400> SEQUENCE: 273
gggugaggua guagguugua aguuugggg cucugcccug cuaugggaua acuauacaau      60
cuacugucuu uccu                                                       74

<210> SEQ ID NO 274
<211> LENGTH: 83
<212> TYPE: RNA
<213> ORGANISM: Mus musculus
<220> FEATURE:
<221> NAME/KEY: misc_RNA
<222> LOCATION: (1)..(83)
<223> OTHER INFORMATION: predicted precursor structure: let-7b, 5' to
      3' sequence

<400> SEQUENCE: 274
cggggugagg uaguagguug uggguuuca gggcagugau guugcccuc ggaagauaac       60 uauacaaccu acugccuucc cug                                             83

<210> SEQ ID NO 275
<211> LENGTH: 85
<212> TYPE: RNA
<213> ORGANISM: Mus musculus
<220> FEATURE:
<221> NAME/KEY: misc_RNA
<222> LOCATION: (1)..(85)
<223> OTHER INFORMATION: predicted precursor structure: let-7c, 5' to
      3' sequence

<400> SEQUENCE: 275
gcauccgggu ugagguagua gguuguaugg uuuagaguua cacccugggg auuaacugua     60
caaccuucua gcuuuccuug gagcg                                           85

<210> SEQ ID NO 276
<211> LENGTH: 87
<212> TYPE: RNA
<213> ORGANISM: Mus musculus
<220> FEATURE:
<221> NAME/KEY: misc_RNA
<222> LOCATION: (1)..(87)
<223> OTHER INFORMATION: predicted precursor structure: let-7d, 5' to
      3' sequence

<400> SEQUENCE: 276
ccuaggaaga gguaguaggu ugcauaguuu uaggcaggg auuuugccca caaggaggua      60
acuauacgac cugcugccuu ucuuagg                                         87

<210> SEQ ID NO 277
<211> LENGTH: 79
<212> TYPE: RNA
<213> ORGANISM: Mus musculus
<220> FEATURE:
<221> NAME/KEY: misc_RNA
<222> LOCATION: (1)..(79)
<223> OTHER INFORMATION: predicted precursor structure: let-7e, 5' to
      3' sequence

<400> SEQUENCE: 277
cccgggcuga gguaggaggu uguauaguug aggaggacac ccaaggagau cacuauacgg     60
```

```
ccuccuagcu uucccccagg                                              79

<210> SEQ ID NO 278
<211> LENGTH: 87
<212> TYPE: RNA
<213> ORGANISM: Mus musculus
<220> FEATURE:
<221> NAME/KEY: misc_RNA
<222> LOCATION: (1)..(87)
<223> OTHER INFORMATION: predicted precursor structure: let-7f-1, 5' to
      3' sequence

<400> SEQUENCE: 278
ucagagugag guaguagauu guauaguugu ggguaguga uuuuacccug uucaggagau    60
aacuauacaa ucuauugccu ucccuga                                      87

<210> SEQ ID NO 279
<211> LENGTH: 85
<212> TYPE: RNA
<213> ORGANISM: Mus musculus
<220> FEATURE:
<221> NAME/KEY: misc_RNA
<222> LOCATION: (1)..(85)
<223> OTHER INFORMATION: predicted precursor structure: let-7f-2, 5' to
      3' sequence

<400> SEQUENCE: 279 cuguggaug agguaguaga uuguauaguu uuagggucau accccaucuu ggagauaacu    60
auacagucua cugucuuucc cacgg                                        85

<210> SEQ ID NO 280
<211> LENGTH: 88
<212> TYPE: RNA
<213> ORGANISM: Mus musculus
<220> FEATURE:
<221> NAME/KEY: misc_RNA
<222> LOCATION: (1)..(88)
<223> OTHER INFORMATION: predicted precursor structure: let-7g, 5' to
      3' sequence

<400> SEQUENCE: 280
ccaggcugag guaguaguuu guacaguuug agggucuaug auaccacccg guacaggaga   60
uaacuguaca ggccacugcc uugccagg                                     88

<210> SEQ ID NO 281
<211> LENGTH: 85
<212> TYPE: RNA
<213> ORGANISM: Mus musculus
<220> FEATURE:
<221> NAME/KEY: misc_RNA
<222> LOCATION: (1)..(85)
<223> OTHER INFORMATION: predicted precursor structure: let-7i, 5' to
      3' sequence

<400> SEQUENCE: 281
cuggcugagg uaguaguuug ugcuguuggu cgguuguga cauugcccgc uguggagaua    60
acugcgcaag cuacugccuu gcuag                                        85

<210> SEQ ID NO 282
<211> LENGTH: 91
<212> TYPE: RNA
<213> ORGANISM: Mus musculus
<220> FEATURE:
<221> NAME/KEY: misc_RNA
<222> LOCATION: (1)..(91)
<223> OTHER INFORMATION: predicted precursor structure: mir-1, 5' to
```

```
                                        3' sequence

<400> SEQUENCE: 282
uucagccuuu gagaguucca ugcuuccuug cauucaauag uuauauucaa gcauauggaa      60
uguaaagaag uauggagcga aaucuggcga g                                    91

<210> SEQ ID NO 283
<211> LENGTH: 79
<212> TYPE: RNA
<213> ORGANISM: Mus musculus
<220> FEATURE:
<221> NAME/KEY: misc_RNA
<222> LOCATION: (1)..(79)
<223> OTHER INFORMATION: predicted precursor structure: mir-1b, 5' to
      3' sequence

<400> SEQUENCE: 283
uacucagagc acauacuucu uuauguaccc auaugaacau ucagugcuau ggaauguaaa      60
gaaguaugua uuuugggua                                                  79

<210> SEQ ID NO 284
<211> LENGTH: 77
<212> TYPE: RNA
<213> ORGANISM: Mus musculus
<220> FEATURE:
<221> NAME/KEY: misc_RNA
<222> LOCATION: (1)..(77)
<223> OTHER INFORMATION: predicted precursor structure: mir-1d, 5' to
      3' sequence

<400> SEQUENCE: 284
gcuugggaca cauacuucuu uauaugccca uaugaaccug cuaagcuaug gaauguaaag      60
aaguauguau uucaggc                                                    77

<210> SEQ ID NO 285
<211> LENGTH: 76
<212> TYPE: RNA
<213> ORGANISM: Mus musculus
<220> FEATURE:
<221> NAME/KEY: misc_RNA
<222> LOCATION: (1)..(76)
<223> OTHER INFORMATION: predicted precursor structure: mir-2a-1, 5' to
      3' sequence

<400> SEQUENCE: 285
gcugggcucu caaagugguu gugaaaugca uuccgcuuu gcgcggcaua ucacagccag       60
cuuugaugag cuuagc                                                     76

<210> SEQ ID NO 286
<211> LENGTH: 72
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: mir-2a-2, 5' to
      3' sequence

<400> SEQUENCE: 286
aucuaagccu caucaagugg uugugauaug gauacccaac gcauaucaca gccagcuuug      60
augagcuagg au                                                         72

<210> SEQ ID NO 287
<211> LENGTH: 77
<212> TYPE: RNA
```

```
-continued

<213> ORGANISM: Mus musculus
<220> FEATURE:
<221> NAME/KEY: misc_RNA
<222> LOCATION: (1)..(77)
<223> OTHER INFORMATION: predicted precursor structure: mir-2b-1, 5' to
      3' sequence

<400> SEQUENCE: 287
cuucaacugu cuucaaagug gcagugacau guugucaaca auauucauau cacagccagc    60
uuugaggagc guugcgg                                                  77

<210> SEQ ID NO 288
<211> LENGTH: 83
<212> TYPE: RNA
<213> ORGANISM: Mus musculus
<220> FEATURE:
<221> NAME/KEY: misc_RNA
<222> LOCATION: (1)..(83)
<223> OTHER INFORMATION: predicted precursor structure: mir-2b-2, 5' to
      3' sequence

<400> SEQUENCE: 288
uugugucauu cuucaaagug guugugaaau guuugccuuu uuaugccuau ucauaucaca    60
gccagcuuug aggagcgacg cga                                           83

<210> SEQ ID NO 289
<211> LENGTH: 69
<212> TYPE: RNA
<213> ORGANISM: Mus musculus
<220> FEATURE:
<221> NAME/KEY: misc_RNA
<222> LOCATION: (1)..(69)
<223> OTHER INFORMATION: predicted precursor structure: mir-3, 5' to 3'
      sequence

<400> SEQUENCE: 289
gauccuggga ugcaucuugu gcaguuaugu uucaaucuca caucacuggg caaagugugu    60
cucaagauc                                                           69

<210> SEQ ID NO 290
<211> LENGTH: 82
<212> TYPE: RNA
<213> ORGANISM: Mus musculus
<220> FEATURE:
<221> NAME/KEY: misc_RNA
<222> LOCATION: (1)..(82)
<223> OTHER INFORMATION: predicted precursor structure: mir-4, 5' to 3'
      sequence

<400> SEQUENCE: 290
uugcaauuag uuucuuuggu cguccagccu uagggugauu uuuccgguca uaaagcuaga    60
caaccauuga aguucguugu gg                                            82

<210> SEQ ID NO 291
<211> LENGTH: 69
<212> TYPE: RNA
<213> ORGANISM: Mus musculus
<220> FEATURE:
<221> NAME/KEY: misc_RNA
<222> LOCATION: (1)..(69)
<223> OTHER INFORMATION: predicted precursor structure: mir-5, 5' to 3'
      sequence

<400> SEQUENCE: 291
gcuaaaagga acgaucguug ugauaugagu uguuccuaa cauaucacag ugauuuuccu     60
uuauaacgc                                                           69
```

```
<210> SEQ ID NO 292
<211> LENGTH: 81
<212> TYPE: RNA
<213> ORGANISM: Mus musculus
<220> FEATURE:
<221> NAME/KEY: misc_RNA
<222> LOCATION: (1)..(81)
<223> OTHER INFORMATION: predicted precursor structure: mir-6-1, 5' to
      3' sequence

<400> SEQUENCE: 292
uuuaauguag agggaauagu ugcugugcug uaaguuaaua uaccauaucu auaucacagg      60
gcuguucuuu uuguaccuaa a                                               81

<210> SEQ ID NO 293
<211> LENGTH: 74
<212> TYPE: RNA
<213> ORGANISM: Mus musculus
<220> FEATURE:
<221> NAME/KEY: misc_RNA
<222> LOCATION: (1)..(74)
<223> OTHER INFORMATION: predicted precursor structure: mir-6-2, 5' to
      3' sequence

<400> SEQUENCE: 293
uaacccaagg gaacuucugc ugcugauaua uuauugaaaa acuacuauau cacaguggcu      60 guucuuuug guug                                                        74

<210> SEQ ID NO 294
<211> LENGTH: 79
<212> TYPE: RNA
<213> ORGANISM: Mus musculus
<220> FEATURE:
<221> NAME/KEY: misc_RNA
<222> LOCATION: (1)..(79)
<223> OTHER INFORMATION: predicted precursor structure: mir-6-3, 5' to
      3' sequence

<400> SEQUENCE: 294
caaaaagaag ggaacgguug cugaugaugu aguuugaaac ucucacaauu uauaucacag      60
uggcuguucu uuuuguuug                                                  79

<210> SEQ ID NO 295
<211> LENGTH: 88
<212> TYPE: RNA
<213> ORGANISM: Mus musculus
<220> FEATURE:
<221> NAME/KEY: misc_RNA
<222> LOCATION: (1)..(88)
<223> OTHER INFORMATION: predicted precursor structure: mir-7, 5' to 3'
      sequence

<400> SEQUENCE: 295
gagugcauuc cguauggaag acuagugauu uuguuguuug gucuuuggua auaacaauaa      60
aucccuuguc uucuuacggc gugcauuu                                        88

<210> SEQ ID NO 296
<211> LENGTH: 87
<212> TYPE: RNA
<213> ORGANISM: Mus musculus
<220> FEATURE:
<221> NAME/KEY: misc_RNA
<222> LOCATION: (1)..(87)
<223> OTHER INFORMATION: predicted precursor structure: mir-8, 5' to 3'
      sequence
```

-continued

```
<400> SEQUENCE: 296
aaggacaucu guucacaucu uaccgggcag cauuagaucc uuuuuauaac ucuaauacug    60
ucagguaaag augucguccg uguccuu                                       87

<210> SEQ ID NO 297
<211> LENGTH: 78
<212> TYPE: RNA
<213> ORGANISM: Mus musculus
<220> FEATURE:
<221> NAME/KEY: misc_RNA
<222> LOCATION: (1)..(78)
<223> OTHER INFORMATION: predicted precursor structure: mir-9, 5' to 3'
      sequence

<400> SEQUENCE: 297
gcuauguugu cuuugguuau cuagcuguau gagugauaaa uaacgucaua aagcuagcuu    60
accgaaguua auauuagc                                                 78

<210> SEQ ID NO 298
<211> LENGTH: 77
<212> TYPE: RNA
<213> ORGANISM: Mus musculus
<220> FEATURE:
<221> NAME/KEY: misc_RNA
<222> LOCATION: (1)..(77)
<223> OTHER INFORMATION: predicted precursor structure: mir-10, 5' to
      3' sequence

<400> SEQUENCE: 298
ccacgucuac ccuguagauc cgaauuuguu uuauacuagc uuuaaggaca aauucgguuc    60
uagagagguu ugugugg                                                  77

<210> SEQ ID NO 299
<211> LENGTH: 75
<212> TYPE: RNA
<213> ORGANISM: Mus musculus
<220> FEATURE:
<221> NAME/KEY: misc_RNA
<222> LOCATION: (1)..(75)
<223> OTHER INFORMATION: predicted precursor structure: mir-11, 5' to
      3' sequence

<400> SEQUENCE: 299
gcacuuguca agaacuuucu cugugacccg cguguacuua aaagccgcau cacagucuga    60
guucuugcug agugc                                                    75

<210> SEQ ID NO 300
<211> LENGTH: 74
<212> TYPE: RNA
<213> ORGANISM: Mus musculus
<220> FEATURE:
<221> NAME/KEY: misc_RNA
<222> LOCATION: (1)..(74)
<223> OTHER INFORMATION: predicted precursor structure: mir-12, 5' to
      3' sequence

<400> SEQUENCE: 300
uacgguugag uauuacauca gguacuggug ugccuuaaau ccaacaacca guacuuaugu    60
cauacuacgc cgug                                                     74

<210> SEQ ID NO 301
<211> LENGTH: 75
<212> TYPE: RNA
<213> ORGANISM: Mus musculus
<220> FEATURE:
```

```
<221> NAME/KEY: misc_RNA
<222> LOCATION: (1)..(75)
<223> OTHER INFORMATION: predicted precursor structure: mir-13a, 5' to
      3' sequence

<400> SEQUENCE: 301
uacguaacuc ucaaagggu ugugaaaugu cgacuauuau cuacucauau cacagccauu     60
uugaugaguu ucgug                                                    75

<210> SEQ ID NO 302
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precursor structure: mir-13b-1, 5'
      to 3' sequence

<400> SEQUENCE: 302
ccaugucguu aaaauguuug ugaacuuaug uauucacaau cauaucacag ccauuuugac    60
gaguuugg                                                            68

<210> SEQ ID NO 303
<211> LENGTH: 70
<212> TYPE: RNA
<213> ORGANISM: Mus musculus
<220> FEATURE:
<221> NAME/KEY: misc_RNA
<222> LOCATION: (1)..(70)
<223> OTHER INFORMATION: predicted precursor structure: mir-13b-2, 5'
      to 3' sequence

<400> SEQUENCE: 303
uauuaacgcg ucaaaaugac ugugagcuau guggauuuga cuucauauca cagccauuuu    60
gacgaguuug                                                          70

<210> SEQ ID NO 304
<211> LENGTH: 65
<212> TYPE: RNA
<213> ORGANISM: Mus musculus
<220> FEATURE:
<221> NAME/KEY: misc_RNA
<222> LOCATION: (1)..(65)
<223> OTHER INFORMATION: predicted precursor structure: mir-14, 5' to
      3' sequence

<400> SEQUENCE: 304
ugugggagcg agacguggga cucacugugc uuauuaaaua gucagucuug uuucucucuc    60
cuaua                                                               65

<210> SEQ ID NO 305
<211> LENGTH: 83
<212> TYPE: RNA
<213> ORGANISM: Mus musculus
<220> FEATURE:
<221> NAME/KEY: misc_RNA
<222> LOCATION: (1)..(83)
<223> OTHER INFORMATION: predicted precursor structure: mir-15a, 5' to
      3' sequence

<400> SEQUENCE: 305
ccuuggagua aaguagcagc acauaauggu uugugauuu ugaaaaggug caggccauau     60
ugugcugccu caaaaauaca agg                                           83
```

```
<210> SEQ ID NO 306
<211> LENGTH: 64
<212> TYPE: RNA
<213> ORGANISM: Mus musculus
<220> FEATURE:
<221> NAME/KEY: misc_RNA
<222> LOCATION: (1)..(64)
<223> OTHER INFORMATION: predicted precursor structure: mir-15b, 5' to
      3' sequence

<400> SEQUENCE: 306
cuguagcagc acaucauggu uuacauacua cagucaagau gcgaaucauu auuugcugcu      60
cuag                                                                  64

<210> SEQ ID NO 307
<211> LENGTH: 89
<212> TYPE: RNA
<213> ORGANISM: Mus musculus
<220> FEATURE:
<221> NAME/KEY: misc_RNA
<222> LOCATION: (1)..(89)
<223> OTHER INFORMATION: predicted precursor structure: mir-16, 5' to
      3' sequence

<400> SEQUENCE: 307
gucagcagug ccuuagcagc acguaaauau uggcguuaag auucuaaaau uaucuccagu      60
auuaacugug cugcugaagu aagguugac                                       89

<210> SEQ ID NO 308
<211> LENGTH: 81
<212> TYPE: RNA
<213> ORGANISM: Mus musculus
<220> FEATURE:
<221> NAME/KEY: misc_RNA
<222> LOCATION: (1)..(81)
<223> OTHER INFORMATION: predicted precursor structure: mir-16, 5' to
      3' sequence

<400> SEQUENCE: 308
guuccacucu agcagcacgu aaauauuggc guagugaaau auauauuaaa caccaauauu      60
acugugcugc uuuaguguga c                                               81

<210> SEQ ID NO 309
<211> LENGTH: 84
<212> TYPE: RNA
<213> ORGANISM: Mus musculus
<220> FEATURE:
<221> NAME/KEY: misc_RNA
<222> LOCATION: (1)..(84)
<223> OTHER INFORMATION: predicted precursor structure: mir-17, 5' to
      3' sequence

<400> SEQUENCE: 309
gucagaauaa ugucaaagug cuuacagugc agguagugau augugcaucu acugcaguga      60
aggcacuugu agcauuaugg ugac                                            84

<210> SEQ ID NO 310
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-18, 5' to
      3' sequence

<400> SEQUENCE: 310
```

```
uguucuaagg ugcaucuagu gcagauagug aaguagauua gcaucuacug cccuaagugc    60
uccuucuggc a                                                         71
```

<210> SEQ ID NO 311
<211> LENGTH: 82
<212> TYPE: RNA
<213> ORGANISM: Mus musculus
<220> FEATURE:
<221> NAME/KEY: misc_RNA
<222> LOCATION: (1)..(82)
<223> OTHER INFORMATION: predicted precursor structure: mir-19a, 5' to
      3' sequence

<400> SEQUENCE: 311

```
gcaguccucu guuaguuuug cauaguugca cuacaagaag aauguaguug ugcaaaucua    60
ugcaaaacug augguggccu gc                                             82
```

<210> SEQ ID NO 312
<211> LENGTH: 87
<212> TYPE: RNA
<213> ORGANISM: Mus musculus
<220> FEATURE:
<221> NAME/KEY: misc_RNA
<222> LOCATION: (1)..(87)
<223> OTHER INFORMATION: predicted precursor structure: mir-19b-1, 5'
      to 3' sequence

<400> SEQUENCE: 312

```
cacuguucua ugguuaguuu ugcagguuug cauccagcug ugugauauuc ugcugugcaa    60
auccaugcaa aacugacugu gguagug                                        87
```

<210> SEQ ID NO 313
<211> LENGTH: 96
<212> TYPE: RNA
<213> ORGANISM: Mus musculus
<220> FEATURE:
<221> NAME/KEY: misc_RNA
<222> LOCATION: (1)..(96)
<223> OTHER INFORMATION: predicted precursor structure: mir-19b-2, 5'
      to 3' sequence

<400> SEQUENCE: 313

```
acauugcuac uuacaauuag uuuugcaggu uugcauuuca gcguauauau guauaugugg    60
cugugcaaau ccaugcaaaa cugauuguga uaaugu                              96
```

<210> SEQ ID NO 314
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-20, 5' to
      3' sequence

<400> SEQUENCE: 314

```
guagcacuaa agugcuuaua gugcagguag uguuuaguua ucuacugcau uaugagcacu    60
uaaaguacug c                                                         71
```

<210> SEQ ID NO 315
<211> LENGTH: 72
<212> TYPE: RNA
<213> ORGANISM: Mus musculus
<220> FEATURE:
<221> NAME/KEY: misc_RNA
<222> LOCATION: (1)..(72)

-continued

<223> OTHER INFORMATION: predicted precursor structure: mir-21, 5' to
     3' sequence

<400> SEQUENCE: 315
ugucggguag cuuaucagac ugauguugac uguugaaucu cauggcaaca ccagucgaug      60
ggcugucuga ca                                                         72

<210> SEQ ID NO 316
<211> LENGTH: 85
<212> TYPE: RNA
<213> ORGANISM: Mus musculus
<220> FEATURE:
<221> NAME/KEY: misc_RNA
<222> LOCATION: (1)..(85)
<223> OTHER INFORMATION: predicted precursor structure: mir-22, 5' to
     3' sequence

<400> SEQUENCE: 316
ggcugagccg caguaguucu ucagugggcaa gcuuuauguc cugacccagc uaaagcugcc     60
aguugaagaa cguugcccu cugcc                                            85

<210> SEQ ID NO 317
<211> LENGTH: 73
<212> TYPE: RNA
<213> ORGANISM: Mus musculus
<220> FEATURE:
<221> NAME/KEY: misc_RNA
<222> LOCATION: (1)..(73)
<223> OTHER INFORMATION: predicted precursor structure: mir-23a, 5' to
     3' sequence

<400> SEQUENCE: 317
ggccggcugg gguuccuggg gaugggauuu gcuuccuguc acaaaucaca uugccaggga     60
uuuccaaccg acc                                                        73

<210> SEQ ID NO 318
<211> LENGTH: 74
<212> TYPE: RNA
<213> ORGANISM: Mus musculus
<220> FEATURE:
<221> NAME/KEY: misc_RNA
<222> LOCATION: (1)..(74)
<223> OTHER INFORMATION: predicted precursor structure: mir-23b, 5' to
     3' sequence

<400> SEQUENCE: 318
ggcugcuugg guuccuggca ugcugauuug ugacuugaga uuaaaaucac auugccaggg     60
auuaccacgc aacc                                                       74

<210> SEQ ID NO 319
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precursor structure: mir-24-1, 5' to
     3' sequence

<400> SEQUENCE: 319
cuccggugcc uacgagcug auaucaguuc ucauuuuaca cacuggcuca guucagcagg     60
aacaggag                                                              68

<210> SEQ ID NO 320
<211> LENGTH: 73

```
<212> TYPE: RNA
<213> ORGANISM: Mus musculus
<220> FEATURE:
<221> NAME/KEY: misc_RNA
<222> LOCATION: (1)..(73)
<223> OTHER INFORMATION: predicted precursor structure: mir-24-2, 5' to
      3' sequence

<400> SEQUENCE: 320
cucugccucc cgugccuacu gagcugaaac acaguugguu uguguacacu ggcucaguuc    60
agcaggaaca ggg                                                      73

<210> SEQ ID NO 321
<211> LENGTH: 84
<212> TYPE: RNA
<213> ORGANISM: Mus musculus
<220> FEATURE:
<221> NAME/KEY: misc_RNA
<222> LOCATION: (1)..(84)
<223> OTHER INFORMATION: predicted precursor structure: mir-25, 5' to
      3' sequence

<400> SEQUENCE: 321
ggccagucuu gagaggcgga gacuugggca auugcuggac gcugcccugg gcauugcacu    60
ugucucgguc ugacagugcc ggcc                                          84

<210> SEQ ID NO 322
<211> LENGTH: 86
<212> TYPE: RNA
<213> ORGANISM: Mus musculus
<220> FEATURE:
<221> NAME/KEY: misc_RNA
<222> LOCATION: (1)..(86)
<223> OTHER INFORMATION: predicted precursor structure: mir-26a, 5' to
      3' sequence

<400> SEQUENCE: 322
aggccguggc cucguucaag uaauccagga uaggcugugc aggucccaau ggccuaucuu    60
gguuacuugc acggggacgc gggccu                                        86

<210> SEQ ID NO 323
<211> LENGTH: 77
<212> TYPE: RNA
<213> ORGANISM: Mus musculus
<220> FEATURE:
<221> NAME/KEY: misc_RNA
<222> LOCATION: (1)..(77)
<223> OTHER INFORMATION: predicted precursor structure: mir-26b, 5' to
      3' sequence

<400> SEQUENCE: 323
ccgggaccca guucaaguaa uucaggauag guugugugcu guccagccug uucuccauua    60
cuuggcucgg ggaccgg                                                  77

<210> SEQ ID NO 324
<211> LENGTH: 78
<212> TYPE: RNA
<213> ORGANISM: Mus musculus
<220> FEATURE:
<221> NAME/KEY: misc_RNA
<222> LOCATION: (1)..(78)
<223> OTHER INFORMATION: predicted precursor structure: mir-27a, 5' to
      3' sequence

<400> SEQUENCE: 324
cugaggagca gggcuuagcu gcuugugagc agguccaca ccaagucgug uucacagugg    60
```

```
cuaaguuccg cccccccag                                              78

<210> SEQ ID NO 325
<211> LENGTH: 73
<212> TYPE: RNA
<213> ORGANISM: Mus musculus
<220> FEATURE:
<221> NAME/KEY: misc_RNA
<222> LOCATION: (1)..(73)
<223> OTHER INFORMATION: predicted precursor structure: mir-27b, 5' to
      3' sequence

<400> SEQUENCE: 325
aggugcagag cuuagcugau uggugaacag ugauugguuu ccgcuuuguu cacaguggcu   60
aaguucugca ccu                                                     73

<210> SEQ ID NO 326
<211> LENGTH: 86
<212> TYPE: RNA
<213> ORGANISM: Mus musculus
<220> FEATURE:
<221> NAME/KEY: misc_RNA
<222> LOCATION: (1)..(86)
<223> OTHER INFORMATION: predicted precursor structure: mir-28, 5' to
      3' sequence

<400> SEQUENCE: 326
gguccuugcc cucaaggagc ucacagucua uugaguuacc uuucugacuu ucccacuaga   60
uugugagcuc cuggagggca ggcacu                                       86

<210> SEQ ID NO 327
<211> LENGTH: 64
<212> TYPE: RNA
<213> ORGANISM: Mus musculus
<220> FEATURE:
<221> NAME/KEY: misc_RNA
<222> LOCATION: (1)..(64)
<223> OTHER INFORMATION: predicted precursor structure: mir-29a, 5' to
      3' sequence

<400> SEQUENCE: 327
augacugauu ucuuuuggug uucagaguca auauaauuuu cuagcaccau cugaaaucgg   60
uuau                                                               64

<210> SEQ ID NO 328
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-29b, 5' to
      3' sequence

<400> SEQUENCE: 328
aggaagcugg uuucauaugg ugguuuagau uuaaauagug auugcuagc accauuugaa    60 aucaguguuc u                                                       71

<210> SEQ ID NO 329
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-30a-s, 5'
      to 3' sequence
```

<400> SEQUENCE: 329
gcgacuguaa acauccucga cuggaagcug ugaagccaca aaugggcuuu cagucggaug    60
uuugcagcug c    71

<210> SEQ ID NO 330
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-30a-as, 5'
      to 3' sequence

<400> SEQUENCE: 330
gcgacuguaa acauccucga cuggaagcug ugaagccaca aaugggcuuu cagucggaug    60
uuugcagcug c    71

<210> SEQ ID NO 331
<211> LENGTH: 60
<212> TYPE: RNA
<213> ORGANISM: Mus musculus
<220> FEATURE:
<221> NAME/KEY: misc_RNA
<222> LOCATION: (1)..(60)
<223> OTHER INFORMATION: predicted precursor structure: mir-30b, 5' to
      3' sequence

<400> SEQUENCE: 331
auguaaacau ccuacacuca gcugucauac augcguuggc ugggaugugg auguuuacgu    60

<210> SEQ ID NO 332
<211> LENGTH: 72
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: mir-30c, 5' to
      3' sequence

<400> SEQUENCE: 332
agauacugua aacauccuac acucucagcu guggaaagua agaaagcugg gagaaggcug    60
uuuacucuuu cu    72

<210> SEQ ID NO 333
<211> LENGTH: 70
<212> TYPE: RNA
<213> ORGANISM: Mus musculus
<220> FEATURE:
<221> NAME/KEY: misc_RNA
<222> LOCATION: (1)..(70)
<223> OTHER INFORMATION: predicted precursor structure: mir-30d, 5' to
      3' sequence

<400> SEQUENCE: 333
guuguuguaa acaucccga cuggaagcug uaagacacag cuaagcuuuc agucagaugu    60
uugcugcuac    70

<210> SEQ ID NO 334
<211> LENGTH: 71
<212> TYPE: RNA
<213> ORGANISM: Mus musculus
<220> FEATURE:
<221> NAME/KEY: misc_RNA

```
<222> LOCATION: (1)..(71)
<223> OTHER INFORMATION: predicted precursor structure: mir-31, 5' to
      3' sequence

<400> SEQUENCE: 334
ggagaggagg caagaugcug gcauagcugu ugaacuggga accugcuaug ccaacauauu    60
gccaucuuuc c                                                         71

<210> SEQ ID NO 335
<211> LENGTH: 70
<212> TYPE: RNA
<213> ORGANISM: Mus musculus
<220> FEATURE:
<221> NAME/KEY: misc_RNA
<222> LOCATION: (1)..(70)
<223> OTHER INFORMATION: predicted precursor structure: mir-32, 5' to
      3' sequence

<400> SEQUENCE: 335
ggagauauug cacauuacua aguugcaugu ugucacggcc ucaaugcaau uuagugugug    60
ugauauuuuc                                                           70

<210> SEQ ID NO 336
<211> LENGTH: 69
<212> TYPE: RNA
<213> ORGANISM: Mus musculus
<220> FEATURE:
<221> NAME/KEY: misc_RNA
<222> LOCATION: (1)..(69)
<223> OTHER INFORMATION: predicted precursor structure: mir-33, 5' to
      3' sequence

<400> SEQUENCE: 336
cuguggugca uguaguugc auugcauguu cuggugguac ccaugcaaug uuccacagu     60 gcaucacag                                                            69

<210> SEQ ID NO 337
<211> LENGTH: 65
<212> TYPE: RNA
<213> ORGANISM: Mus musculus
<220> FEATURE:
<221> NAME/KEY: misc_RNA
<222> LOCATION: (1)..(65)
<223> OTHER INFORMATION: predicted precursor structure: mir-99a, 5' to
      3' sequence

<400> SEQUENCE: 337
cauaaacccg uagauccgau cuuguggyga aguggaccgc gcaagcucgu uucuaugggu    60
cugug                                                                65

<210> SEQ ID NO 338
<211> LENGTH: 70
<212> TYPE: RNA
<213> ORGANISM: Mus musculus
<220> FEATURE:
<221> NAME/KEY: misc_RNA
<222> LOCATION: (1)..(70)
<223> OTHER INFORMATION: predicted precursor structure: mir-99b, 5' to
      3' sequence

<400> SEQUENCE: 338
ggcacccacc cguagaaccg accuugcggg gccuucgccg cacacaagcu cgugucugug    60
gguccguguc                                                           70

<210> SEQ ID NO 339
```

```
<211> LENGTH: 57
<212> TYPE: RNA
<213> ORGANISM: Mus musculus
<220> FEATURE:
<221> NAME/KEY: misc_RNA
<222> LOCATION: (1)..(57)
<223> OTHER INFORMATION: predicted precursor structure: mir-101, 5' to
      3' sequence

<400> SEQUENCE: 339
ucaguuauca cagugcugau gcuguccauu cuaaagguac aguacuguga uaacuga       57

<210> SEQ ID NO 340
<211> LENGTH: 66
<212> TYPE: RNA
<213> ORGANISM: Mus musculus
<220> FEATURE:
<221> NAME/KEY: misc_RNA
<222> LOCATION: (1)..(66)
<223> OTHER INFORMATION: predicted precursor structure: mir-122a, 5' to
      3' sequence

<400> SEQUENCE: 340
agcuguggag ugugacaaug guguuugugu ccaaaccauc aaacgccauu aucacacuaa    60
auagcu                                                              66

<210> SEQ ID NO 341
<211> LENGTH: 73
<212> TYPE: RNA
<213> ORGANISM: Mus musculus
<220> FEATURE:
<221> NAME/KEY: misc_RNA
<222> LOCATION: (1)..(73)
<223> OTHER INFORMATION: predicted precursor structure: mir-123, 5' to
      3' sequence

<400> SEQUENCE: 341
ugacagcaca uuauuacuuu ugguacgcgc ugugacacuu caaacucgua ccgugaguaa    60
uaaugcgcgg uca                                                      73

<210> SEQ ID NO 342
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precursor structure: mir-124a, 5'
      to 3' sequence
<220> FEATURE:
<221> NAME/KEY: misc_RNA
<222> LOCATION: (1)..(68)
<223> OTHER INFORMATION: predicted precursor structure: mir-124a*, 5'
      to 3' sequence

<400> SEQUENCE: 342
cucugcgugu ucacagcgga ccuugauuua augucuauac aauuaaggca cgcggugaau    60
gccaagag                                                            68

<210> SEQ ID NO 343
<211> LENGTH: 67
<212> TYPE: RNA
<213> ORGANISM: Mus musculus
<220> FEATURE:
<221> NAME/KEY: misc_RNA
<222> LOCATION: (1)..(67)
<223> OTHER INFORMATION: predicted precursor structure: mir-124b, 5' to
      3' sequence
```

-continued

<400> SEQUENCE: 343
cucuccgugu ucacagcgga ccuugauuua augucauaca auuaaggcac gcggugaaug    60
ccaagag    67

<210> SEQ ID NO 344
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precursor structure: mir-125a, 5' to
      3' sequence

<400> SEQUENCE: 344
cugggucccu gagacccuuu aaccugugag gacguccagg gucacaggug agguucuugg    60
gagccugg    68

<210> SEQ ID NO 345
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-125b, 5' to
      3' sequence

<400> SEQUENCE: 345
gccuaguccc ugagacccua acugugagg uauuuuagua acaucacaag ucagguucuu    60
gggaccuagg c    71

<210> SEQ ID NO 346
<211> LENGTH: 73
<212> TYPE: RNA
<213> ORGANISM: Mus musculus
<220> FEATURE:
<221> NAME/KEY: misc_RNA
<222> LOCATION: (1)..(73)
<223> OTHER INFORMATION: predicted precursor structure: mir-126, 5' to
      3' sequence

<400> SEQUENCE: 346
ugacagcaca uuauuacuuu ugguacgcgc ugugacacuu caaacucgua ccgugaguaa    60
uaaugcgcgg uca    73

<210> SEQ ID NO 347
<211> LENGTH: 70
<212> TYPE: RNA
<213> ORGANISM: Mus musculus
<220> FEATURE:
<221> NAME/KEY: misc_RNA
<222> LOCATION: (1)..(70)
<223> OTHER INFORMATION: predicted precursor structure: mir-127, 5' to
      3' sequence

<400> SEQUENCE: 347
ccagccugcu gaagcucaga gggcucugau ucagaaagau caucggaucc gucugagcuu    60
ggcuggucgg    70

<210> SEQ ID NO 348
<211> LENGTH: 70
<212> TYPE: RNA
<213> ORGANISM: Mus musculus
<220> FEATURE:

<210> SEQ ID NO 348
<211> LENGTH: 70
<212> TYPE: RNA
<213> ORGANISM: Mus musculus
<220> FEATURE:
<221> NAME/KEY: misc_RNA
<222> LOCATION: (1)..(70)
<223> OTHER INFORMATION: predicted precursor structure: mir-128, 5' to
      3' sequence

<400> SEQUENCE: 348
guuggauucg gggccguagc acugucugag agguuuacau uucucacagu gaaccggucu    60
cuuuuucagc                                                          70

<210> SEQ ID NO 349
<211> LENGTH: 72
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: mir-129, 5' to
      3' sequence

<400> SEQUENCE: 349
ggaucuuuuu gcggucuggg cuugcuguuc cucucaacag uagucaggaa gcccuuaccc    60
caaaaaguau cu                                                       72

<210> SEQ ID NO 350
<211> LENGTH: 64
<212> TYPE: RNA
<213> ORGANISM: Mus musculus
<220> FEATURE:
<221> NAME/KEY: misc_RNA
<222> LOCATION: (1)..(64)
<223> OTHER INFORMATION: predicted precursor structure: mir-130, 5' to
      3' sequence

<400> SEQUENCE: 350
gagcucuuuu cacauugugc uacugucuaa cguguaccga gcagugcaau guuaaaaggg    60
cauc                                                                64

<210> SEQ ID NO 351
<211> LENGTH: 72
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: mir-131, 5' to
      3' sequence

<400> SEQUENCE: 351
guuguuaucu uugguuaucu agcuguauga guguauuggu cuucauaaag cuagauaacc    60
gaaaguaaaa ac                                                       72

<210> SEQ ID NO 352
<211> LENGTH: 66
<212> TYPE: RNA
<213> ORGANISM: Mus musculus
<220> FEATURE:
<221> NAME/KEY: misc_RNA
<222> LOCATION: (1)..(66)
<223> OTHER INFORMATION: predicted precursor structure: mir-132, 5' to
      3' sequence

<400> SEQUENCE: 352
gggcaaccgu ggcuuucgau uguuacugug ggaaccggag guaacagucu acagccaugg    60
ucgccc                                                              66

```
<210> SEQ ID NO 353
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precursor structure: mir-133, 5' to
      3' sequence

<400> SEQUENCE: 353
gcuaaagcug guaaaaugga accaaaucgc cucuucaaug gauuuggucc ccuucaacca      60
gcuguagc                                                              68

<210> SEQ ID NO 354
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-134, 5' to
      3' sequence

<400> SEQUENCE: 354
agggugugug acugguugac cagaggggcg ugcacucugu ucacccugug ggccaccuag      60
ucaccaaccc u                                                          71

<210> SEQ ID NO 355
<211> LENGTH: 60
<212> TYPE: RNA
<213> ORGANISM: Mus musculus
<220> FEATURE:
<221> NAME/KEY: misc_RNA
<222> LOCATION: (1)..(60)
<223> OTHER INFORMATION: predicted precursor structure: mir-135, 5' to
      3' sequence

<400> SEQUENCE: 355
cuauggcuuu uuauuccuau gugauucuau ugcucgcuca uauagggauu ggagccgugg      60

<210> SEQ ID NO 356
<211> LENGTH: 62
<212> TYPE: RNA
<213> ORGANISM: Mus musculus
<220> FEATURE:
<221> NAME/KEY: misc_RNA
<222> LOCATION: (1)..(62)
<223> OTHER INFORMATION: predicted precursor structure: mir-136, 5' to
      3' sequence

<400> SEQUENCE: 356
gaggacucca uuuguuuuga ugauggauuc uuaagcucca ucaucgucuc aaaugagucu      60
uc                                                                    62

<210> SEQ ID NO 357
<211> LENGTH: 73
<212> TYPE: RNA
<213> ORGANISM: Mus musculus
<220> FEATURE:
<221> NAME/KEY: misc_RNA
<222> LOCATION: (1)..(73)
<223> OTHER INFORMATION: predicted precursor structure: mir-137, 5' to
      3' sequence

<400> SEQUENCE: 357
cuucggugac ggguauucuu ggguggauaa uacggauuac guuguuauug cuuaagaaua      60
```

-continued

```
cgcguagucg agg                                                          73

<210> SEQ ID NO 358
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-138, 5' to
      3' sequence

<400> SEQUENCE: 358
cagcuggugu ugugaaucag gccgacgagc agcgcauccu cuuacccggc uauuucacga        60
caccaggguu g                                                            71

<210> SEQ ID NO 359
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precursor structure: mir-139, 5' to
      3' sequence

<400> SEQUENCE: 359
guguauucua cagugcacgu gucuccagug uggcucggag gcuggagacg cggcccuguu        60
ggaguaac                                                                68

<210> SEQ ID NO 360
<211> LENGTH: 70
<212> TYPE: RNA
<213> ORGANISM: Mus musculus
<220> FEATURE:
<221> NAME/KEY: misc_RNA
<222> LOCATION: (1)..(70)
<223> OTHER INFORMATION: predicted precursor structure: mir-140, 5' to
      3' sequence

<400> SEQUENCE: 360
ccugccagug guuuuacccu augguagguu acgucaugcu guucuaccac aggguagaac        60
cacggacagg                                                              70

<210> SEQ ID NO 361
<211> LENGTH: 72
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: mir-141, 5' to
      3' sequence

<400> SEQUENCE: 361
ggguccaucu uccagugcag uguuggaugg uugaaguaug aagcuccuaa cacugucugg        60
uaaagauggc cc                                                           72

<210> SEQ ID NO 362
<211> LENGTH: 64
<212> TYPE: RNA
<213> ORGANISM: Mus musculus
<220> FEATURE:
<221> NAME/KEY: misc_RNA
<222> LOCATION: (1)..(64)
<223> OTHER INFORMATION: predicted precursor structure: mir-142s, 5'
      to 3' sequence
```

<400> SEQUENCE: 362
acccauaaag uagaaagcac uacuaacagc acuggagggu guaguguuuc cuacuuuaug     60
gaug                                                                 64

<210> SEQ ID NO 363
<211> LENGTH: 64
<212> TYPE: RNA
<213> ORGANISM: Mus musculus
<220> FEATURE:
<221> NAME/KEY: misc_RNA
<222> LOCATION: (1)..(64)
<223> OTHER INFORMATION: predicted precursor structure: mir-142as*, 5'
      to 3' sequence

<400> SEQUENCE: 363
acccauaaag uagaaagcac uacuaacagc acuggagggu guaguguuuc cuacuuuaug     60
gaug                                                                 64

<210> SEQ ID NO 364
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: new, 5' to 3'
      sequence

<400> SEQUENCE: 364
ugacgggcga gcuuuuggcc cggguuauac cugaugcuca cguauaagac gagcaaaaag     60
cuuguugguc a                                                         71

<210> SEQ ID NO 365
<211> LENGTH: 63
<212> TYPE: RNA
<213> ORGANISM: Mus musculus
<220> FEATURE:
<221> NAME/KEY: misc_RNA
<222> LOCATION: (1)..(63)
<223> OTHER INFORMATION: predicted precursor structure: mir-143, 5' to
      3' sequence

<400> SEQUENCE: 365
ccugaggugc agugcugcau cucuggucag uugggagucu gagaugaagc acguagcuc     60 agg                                                                  63

<210> SEQ ID NO 366
<211> LENGTH: 66
<212> TYPE: RNA
<213> ORGANISM: Mus musculus
<220> FEATURE:
<221> NAME/KEY: misc_RNA
<222> LOCATION: (1)..(66)
<223> OTHER INFORMATION: predicted precursor structure: mir-144, 5' to
      3' sequence

<400> SEQUENCE: 366
ggcugggaua ucaucauaua cguuaaguuu gugaugagac acuacaguau agaugaugua     60
cuaguc                                                               66

<210> SEQ ID NO 367
<211> LENGTH: 70
<212> TYPE: RNA
<213> ORGANISM: Mus musculus

```
<220> FEATURE:
<221> NAME/KEY: misc_RNA
<222> LOCATION: (1)..(70)
<223> OTHER INFORMATION: predicted precursor structure: mir-145, 5' to
      3' sequence

<400> SEQUENCE: 367
cucacggucc aguuucccca ggaaucccuu ggaugcuaag augggauuc cuggaaauac      60 uguucuugag                                                           70

<210> SEQ ID NO 368
<211> LENGTH: 65
<212> TYPE: RNA
<213> ORGANISM: Mus musculus
<220> FEATURE:
<221> NAME/KEY: misc_RNA
<222> LOCATION: (1)..(65)
<223> OTHER INFORMATION: predicted precursor structure: mir-146, 5' to
      3' sequence

<400> SEQUENCE: 368
agcucugaga acugaauucc auggguuaua ucaaugucag accugugaaa uucaguucuu      60
cagcu                                                                 65

<210> SEQ ID NO 369
<211> LENGTH: 72
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: mir-147, 5' to
      3' sequence

<400> SEQUENCE: 369
aaucuaaaga caacauuucu gcacacacac cagacuaugg aagccagugu guggaaaugc      60
uucugcuaga uu                                                         72

<210> SEQ ID NO 370
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precusor structure: mir-148, 5' to
      3' sequence

<400> SEQUENCE: 370
gaggcaaagu ucugagacac uccgacucug aguaugauag aagucagugc acuacagaac      60
uuugucuc                                                              68

<210> SEQ ID NO 371
<211> LENGTH: 66
<212> TYPE: RNA
<213> ORGANISM: Mus musculus
<220> FEATURE:
<221> NAME/KEY: misc_RNA
<222> LOCATION: (1)..(66)
<223> OTHER INFORMATION: predicted precursor structure: mir-149, 5' to
      3' sequence

<400> SEQUENCE: 371
ggcucuggcu ccgugucuuc acucccgugu uugucgagg agggagggag ggacagaggc      60
ggggcu                                                                66
```

```
<210> SEQ ID NO 372
<211> LENGTH: 65
<212> TYPE: RNA
<213> ORGANISM: Mus musculus
<220> FEATURE:
<221> NAME/KEY: misc_RNA
<222> LOCATION: (1)..(65)
<223> OTHER INFORMATION: predicted precursor structure: mir-150, 5' to
      3' sequence

<400> SEQUENCE: 372
cccugucucc caacccuugu accagugcug ugccucagac ccugguacag gccuggggga    60
uaggg                                                                65

<210> SEQ ID NO 373
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precursor structure: mir-151, 5' to
      3' sequence

<400> SEQUENCE: 373
ccugcccucg aggagcucac agucuaguau gucuccuccc uacuagacug aggcuccuug    60
aggacagg                                                             68

<210> SEQ ID NO 374
<211> LENGTH: 73
<212> TYPE: RNA
<213> ORGANISM: Mus musculus
<220> FEATURE:
<221> NAME/KEY: misc_RNA
<222> LOCATION: (1)..(73)
<223> OTHER INFORMATION: predicted precursor structure: mir-152, 5' to
      3' sequence

<400> SEQUENCE: 374
ccgggccuag guucugugau acacuccgac ucgggcucug gagcagucag ugcaugacag    60
aacuugggcc cgg                                                       73

<210> SEQ ID NO 375
<211> LENGTH: 69
<212> TYPE: RNA
<213> ORGANISM: Mus musculus
<220> FEATURE:
<221> NAME/KEY: misc_RNA
<222> LOCATION: (1)..(69)
<223> OTHER INFORMATION: predicted precursor structure: mir-153, 5' to
      3' sequence

<400> SEQUENCE: 375
cagugucauu uuugugaugu ugcagcuagu aauaugagcc caguugcaua gucacaaaag    60
ugaucauug                                                            69

<210> SEQ ID NO 376
<211> LENGTH: 66
<212> TYPE: RNA
<213> ORGANISM: Mus musculus
<220> FEATURE:
<221> NAME/KEY: misc_RNA
<222> LOCATION: (1)..(66)
<223> OTHER INFORMATION: predicted precursor structure: mir-154, 5' to
      3' sequence

<400> SEQUENCE: 376
```
gaagauaggu uauccguguu gccuucgcuu uauuugugac gaaucauaca cgguugaccu    60
auuuuu    66

<210> SEQ ID NO 377
<211> LENGTH: 65
<212> TYPE: RNA
<213> ORGANISM: Mus musculus
<220> FEATURE:
<221> NAME/KEY: mice_RNA
<222> LOCATION: (1)..(65)
<223> OTHER INFORMATION: predicted precursor structure: mir-155 (BIC-
      RNA), 5' to 3' sequence

<400> SEQUENCE: 377
cuguuaaugc uaauugugau aggguuuug gccucugacu gacuccuacc uguuagcauu    60
aacag    65

<210> SEQ ID NO 378
<211> LENGTH: 76
<212> TYPE: RNA
<213> ORGANISM: Homo sapiens and Mus musculus
<220> FEATURE:
<221> NAME/KEY: misc_RNA
<222> LOCATION: (1)..(76)
<223> OTHER INFORMATION: predicted precursor structure: mir-C1, 5' to
      3' sequence

<400> SEQUENCE: 378
ccauggaaca uucaacgcug ucggugaguu ugggauucaa aaacaaaaaa accaccgacc    60
guugacugua ccuugg    76

<210> SEQ ID NO 379
<211> LENGTH: 75
<212> TYPE: RNA
<213> ORGANISM: Homo sapiens and Mus musculus
<220> FEATURE:
<221> NAME/KEY: misc_RNA
<222> LOCATION: (1)..(75)
<223> OTHER INFORMATION: predicted precursor structure: mir-C2, 5' to
      3' sequence

<400> SEQUENCE: 379
accauuuuug gcaaggguag aacucacacc gguaagguaa ugggacccgg ugguucuaga    60
cuugccaacu auggu    75

<210> SEQ ID NO 380
<211> LENGTH: 70
<212> TYPE: RNA
<213> ORGANISM: Homo sapiens and Mus musculus
<220> FEATURE:
<221> NAME/KEY: misc_RNA
<222> LOCATION: (1)..(70)
<223> OTHER INFORMATION: predicted precursor structure: mir-C3, 5' to
      3' sequence

<400> SEQUENCE: 380
cuguguaugg cacgguaga auucacugug aacagucuca gucagugaau uaccgaaggg    60
ccauaaacag    70

<210> SEQ ID NO 381
<211> LENGTH: 73
<212> TYPE: RNA
<213> ORGANISM: Homo sapiens and Mus musculus
<220> FEATURE:
<221> NAME/KEY: misc_RNA -continued

```
<222> LOCATION: (1)..(73)
<223> OTHER INFORMATION: predicted precursor structure: mir-C4, 5' to
      3' sequence

<400> SEQUENCE: 381
uggaucuuuu ugcggucugg gcuugcuguu uucucgacag uagucaggaa gcccuuaccc    60
caaaaaguau cua                                                      73

<210> SEQ ID NO 382
<211> LENGTH: 69
<212> TYPE: RNA
<213> ORGANISM: Homo sapiens and Mus musculus
<220> FEATURE:
<221> NAME/KEY: misc_RNA
<222> LOCATION: (1)..(69)
<223> OTHER INFORMATION: predicted precursor structure: mir-C5, 5' to
      3' sequence

<400> SEQUENCE: 382 ccuuccuua ucacuuuucc agccagcuuu gugacucuaa guguuggacg gagaacugau     60
aaggguagg                                                           69

<210> SEQ ID NO 383
<211> LENGTH: 65
<212> TYPE: RNA
<213> ORGANISM: Homo sapiens and Mus musculus
<220> FEATURE:
<221> NAME/KEY: misc_RNA
<222> LOCATION: (1)..(65)
<223> OTHER INFORMATION: predicted precursor structure: mir-C6, 5' to
      3' sequence

<400> SEQUENCE: 383
agggauugga gagaaaggca guuccugaug gucccuccc aggggcuggc uuuccucugg     60
uccuu                                                               65

<210> SEQ ID NO 384
<211> LENGTH: 71
<212> TYPE: RNA
<213> ORGANISM: Homo sapiens and Mus musculus
<220> FEATURE:
<221> NAME/KEY: misc_RNA
<222> LOCATION: (1)..(71)
<223> OTHER INFORMATION: predicted precursor structure: mir-C7, 5' to
      3' sequence

<400> SEQUENCE: 384 acuuccaaa gaauucuccu uuugggcuuu cucauuuuau uuuaagcccu aaggugaauu     60
uuuugggaag u                                                        71

<210> SEQ ID NO 385
<211> LENGTH: 61
<212> TYPE: RNA
<213> ORGANISM: Homo sapiens and Mus musculus
<220> FEATURE:
<221> NAME/KEY: misc_RNA
<222> LOCATION: (1)..(61)
<223> OTHER INFORMATION: predicted precursor structure: mir-C8, 5' to
      3' sequence

<400> SEQUENCE: 385
ucaggcuaca acacaggacc cgggcgcugc ucugaccccu cgugucuugu guugcagccg    60
g                                                                   61

<210> SEQ ID NO 386
```

```
<211> LENGTH: 70
<212> TYPE: RNA
<213> ORGANISM: Homo sapiens and Mus musculus
<220> FEATURE:
<221> NAME/KEY: misc_RNA
<222> LOCATION: (1)..(70)
<223> OTHER INFORMATION: predicted precursor structure: mir-C9, 5' to
      3' sequence

<400> SEQUENCE: 386
gccguggcca ucuuacuggg cagcauugga uagugucuga ucucuaauac ugccugguaa      60
ugaugacggc                                                            70

<210> SEQ ID NO 387
<211> LENGTH: 68
<212> TYPE: RNA
<213> ORGANISM: Homo sapiens and Mus musculus
<220> FEATURE:
<221> NAME/KEY: misc_RNA
<222> LOCATION: (1)..(68)
<223> OTHER INFORMATION: predicted precursor structure: mir-C10, 5' to
      3' sequence

<400> SEQUENCE: 387
ucucacaucc cuugcauggu ggagggugag cucucugaaa accccuccca caugcagggu      60
uugcagga                                                              68

<210> SEQ ID NO 388
<211> LENGTH: 68
<212> TYPE: RNA
<213> ORGANISM: Homo sapiens and Mus musculus
<220> FEATURE:
<221> NAME/KEY: misc_RNA
<222> LOCATION: (1)..(68)
<223> OTHER INFORMATION: predicted precursor structure: mir-C11, 5' to
      3' sequence

<400> SEQUENCE: 388
cuccggugcc uacugagcug auaucaguuc ucauuucaca cacuggcuca guucagcagg      60
aacaggag                                                              68

<210> SEQ ID NO 389
<211> LENGTH: 67
<212> TYPE: RNA
<213> ORGANISM: Homo sapiens and Mus musculus
<220> FEATURE:
<221> NAME/KEY: misc_RNA
<222> LOCATION: (1)..(67)
<223> OTHER INFORMATION: predicted precursor structure: mir-C12, 5' to
      3' sequence

<400> SEQUENCE: 389
cugugugaua uguuugauau auuagguugu uauuuaaucc aacauauauau caagcauauu     60 ccuacag                                                               67

<210> SEQ ID NO 390
<211> LENGTH: 74
<212> TYPE: RNA
<213> ORGANISM: Homo sapiens and Mus musculus
<220> FEATURE:
<221> NAME/KEY: misc_RNA
<222> LOCATION: (1)..(74)
<223> OTHER INFORMATION: predicted precursor structure: mir-C13, 5' to
      3' sequence

<400> SEQUENCE: 390
agcgggcaac ggaaucccaa aagcagcugu ugucuccaga gcauuccagc ugcacuugga      60
```

-continued uuucguuccc ugcu                                                       74

<210> SEQ ID NO 391
<211> LENGTH: 62
<212> TYPE: RNA
<213> ORGANISM: Homo sapiens and Mus musculus
<220> FEATURE:
<221> NAME/KEY: misc_RNA
<222> LOCATION: (1)..(62)
<223> OTHER INFORMATION: predicted precursor structure: mir-c14, 5' to
      3' sequence

<400> SEQUENCE: 391
cugaccuaug aauugacagc cagugcucuc gucucccuc uggcugccaa uuccauaggu       60
ca                                                                    62

<210> SEQ ID NO 392
<211> LENGTH: 72
<212> TYPE: RNA
<213> ORGANISM: Homo sapiens and Mus musculus
<220> FEATURE:
<221> NAME/KEY: misc_RNA
<222> LOCATION: (1)..(72)
<223> OTHER INFORMATION: predicted precursor structure: mir-c15, 5' to
      3' sequence

<400> SEQUENCE: 392
uccugccggu gguuuuaccc uaugguaggu uacgucaugc uguucuacca caggguagaa     60
ccacggacag ga                                                         72

<210> SEQ ID NO 393
<211> LENGTH: 66
<212> TYPE: RNA
<213> ORGANISM: Homo sapiens and Mus musculus
<220> FEATURE:
<221> NAME/KEY: misc_RNA
<222> LOCATION: (1)..(66)
<223> OTHER INFORMATION: predicted precursor structure: mir-c16, 5' to
      3' sequence

<400> SEQUENCE: 393
gagagcuggg ucuuugcggg caagaugaga gugucaguuc aacuggccua caaaguccca     60
guccuc                                                                66

<210> SEQ ID NO 394
<211> LENGTH: 67
<212> TYPE: RNA
<213> ORGANISM: Homo sapiens and Mus musculus
<220> FEATURE:
<221> NAME/KEY: misc_RNA
<222> LOCATION: (1)..(67)
<223> OTHER INFORMATION: predicted precursor structure: mir-c17, 5' to
      3' sequence

<400> SEQUENCE: 394
aucgggugua acagcaacuc cauguggacu gugcucggau uccaguggag cugcuguuac     60
uucugau                                                               67

<210> SEQ ID NO 395
<211> LENGTH: 58
<212> TYPE: RNA
<213> ORGANISM: Homo sapiens and Mus musculus
<220> FEATURE:
<221> NAME/KEY: misc_RNA
<222> LOCATION: (1)..(58)
<223> OTHER INFORMATION: predicted precursor structure: mir-c18, 5' to -continued 3' sequence

<400> SEQUENCE: 395
uagcagcaca gaaauauugg caugggggaag ugagucugcc aauauuggcu gugcugcu    58

<210> SEQ ID NO 396
<211> LENGTH: 70
<212> TYPE: RNA
<213> ORGANISM: Homo sapiens and Mus musculus
<220> FEATURE:
<221> NAME/KEY: misc_RNA
<222> LOCATION: (1)..(70)
<223> OTHER INFORMATION: predicted precursor structure: mic-c19, 5' to
      3' sequence

<400> SEQUENCE: 396
gugaauuagg uaguuucaug uuguugggcc uggguuucug aacacaacaa cauuaaacca    60
cccgauucac                                                          70

<210> SEQ ID NO 397
<211> LENGTH: 75
<212> TYPE: RNA
<213> ORGANISM: Homo sapiens and Mus musculus
<220> FEATURE:
<221> NAME/KEY: misc_RNA
<222> LOCATION: (1)..(75)
<223> OTHER INFORMATION: predicted precursor structure: mir-c20, 5' to
      3' sequence

<400> SEQUENCE: 397
ggcugugccg gguagagagg gcagugggag guaagagcuc uucacccuuc accaccuucu    60
ccacccagca uggcc                                                    75

<210> SEQ ID NO 398
<211> LENGTH: 62
<212> TYPE: RNA
<213> ORGANISM: Homo sapiens and Mus musculus
<220> FEATURE:
<221> NAME/KEY: misc_RNA
<222> LOCATION: (1)..(62)
<223> OTHER INFORMATION: predicted precursor structure: mir-c21, 5' to
      3' sequence

<400> SEQUENCE: 398
ucauuggucc agaggggaga uagguuccug ugauuuuucc uucuucucua uagaauaaau    60
ga                                                                  62

<210> SEQ ID NO 399
<211> LENGTH: 70
<212> TYPE: RNA
<213> ORGANISM: Homo sapiens and Mus musculus
<220> FEATURE:
<221> NAME/KEY: misc_RNA
<222> LOCATION: (1)..(70)
<223> OTHER INFORMATION: predicted precursor structure: mir-c22, 5' to
      3' sequence

<400> SEQUENCE: 399
gccaucccag uguucagacu accuguucag gaggcuggga cauguacagu agucugcaca    60
uugguuaggc                                                          70

<210> SEQ ID NO 400
<211> LENGTH: 70
<212> TYPE: RNA
<213> ORGANISM: Homo sapiens and Mus musculus
<220> FEATURE:

```
<221> NAME/KEY: misc_RNA
<222> LOCATION: (1)..(70)
<223> OTHER INFORMATION: predicted precursor structure: mir-c23, 5' to
      3' sequence

<400> SEQUENCE: 400
gccguggcca ucuuacuggg cagcauugga uagugucuga ucucuaauac ugccugguaa    60
ugaugacggc                                                          70

<210> SEQ ID NO 401
<211> LENGTH: 66
<212> TYPE: RNA
<213> ORGANISM: Homo sapiens and Mus musculus
<220> FEATURE:
<221> NAME/KEY: misc_RNA
<222> LOCATION: (1)..(66)
<223> OTHER INFORMATION: predicted precursor structure: mir-c24, 5' to
      3' sequence

<400> SEQUENCE: 401
uaccuuacuc aguaaggcau uguucuucua uauuaauaaa ugaacagugc cuuucugugu    60
agggua                                                              66

<210> SEQ ID NO 402
<211> LENGTH: 72
<212> TYPE: RNA
<213> ORGANISM: Homo sapiens and Mus musculus
<220> FEATURE:
<221> NAME/KEY: misc_RNA
<222> LOCATION: (1)..(72)
<223> OTHER INFORMATION: predicted precursor structure: mir-c25, 5' to
      3' sequence

<400> SEQUENCE: 402
guuccuuuuu ccuaugcaua uacuucuuug uggaucuggu cuaaagaggu auagcgcaug    60
ggaagaugga gc                                                       72

<210> SEQ ID NO 403
<211> LENGTH: 68
<212> TYPE: RNA
<213> ORGANISM: Homo sapiens and Mus musculus
<220> FEATURE:
<221> NAME/KEY: misc_RNA
<222> LOCATION: (1)..(68)
<223> OTHER INFORMATION: predicted precursor structure: mir-c26, 5' to
      3' sequence

<400> SEQUENCE: 403
cggucagugg uuucuggaca auucaccagu uuugacagaa uucgugaaug uuaagguacc    60
acugacca                                                            68

<210> SEQ ID NO 404
<211> LENGTH: 68
<212> TYPE: RNA
<213> ORGANISM: Homo sapiens and Mus musculus
<220> FEATURE:
<221> NAME/KEY: misc_RNA
<222> LOCATION: (1)..(68)
<223> OTHER INFORMATION: predicted precursor structure: mir-c27, 5' to
      3' sequence

<400> SEQUENCE: 404
uggacuuccc uuugucaucc uaugccugag aauauaugaa ggaggcuggg aaggcaaagg    60
gacguuca                                                            68
```

```
<210> SEQ ID NO 405
<211> LENGTH: 68
<212> TYPE: RNA
<213> ORGANISM: Homo sapiens and Mus musculus
<220> FEATURE:
<221> NAME/KEY: misc_RNA
<222> LOCATION: (1)..(68)
<223> OTHER INFORMATION: predicted precursor structure: mir-c28, 5' to
      3' sequence

<400> SEQUENCE: 405
cucuuguccu ucauuccacc ggagucuguc uuaugccaac cagauuucag uggagugaag     60
cucaggag                                                             68

<210> SEQ ID NO 406
<211> LENGTH: 76
<212> TYPE: RNA
<213> ORGANISM: Homo sapiens and Mus musculus
<220> FEATURE:
<221> NAME/KEY: misc_RNA
<222> LOCATION: (1)..(76)
<223> OTHER INFORMATION: predicted precursor structure: mir-c29, 5' to
      3' sequence

<400> SEQUENCE: 406
gccuggucca gugguucuug acaguucaac aguucuguag cacaauugug aaauguuuag     60
gaccacuaga cccggc                                                    76

<210> SEQ ID NO 407
<211> LENGTH: 73
<212> TYPE: RNA
<213> ORGANISM: Homo sapiens and Mus musculus
<220> FEATURE:
<221> NAME/KEY: misc_RNA
<222> LOCATION: (1)..(73)
<223> OTHER INFORMATION: predicted precursor structure: mir-c30, 5' to
      3' sequence

<400> SEQUENCE: 407
ccaggccaca ugcuucuuua uauccucaua gauaucucag cacuauggaa uguaaggaag     60
ugugugguuu ugg                                                       73

<210> SEQ ID NO 408
<211> LENGTH: 70
<212> TYPE: RNA
<213> ORGANISM: Homo sapiens and Mus musculus
<220> FEATURE:
<221> NAME/KEY: misc_RNA
<222> LOCATION: (1)..(70)
<223> OTHER INFORMATION: predicted precursor structure: mir-C31, 5' to
      3' sequence

<400> SEQUENCE: 408
gccaucccag uguucagacu accuguucag gaggcuggga cauguacagu agucugcaca     60
uugguuaggc                                                           70

<210> SEQ ID NO 409
<211> LENGTH: 68
<212> TYPE: RNA
<213> ORGANISM: Homo sapiens and Mus musculus
<220> FEATURE:
<221> NAME/KEY: misc_RNA
<222> LOCATION: (1)..(68)
<223> OTHER INFORMATION: predicted precursor structure: mir-c32, 5' to
      3' sequence

<400> SEQUENCE: 409
```
uauauacccu guagaaccga auuugugugg uacccacaua gucacagauu cgauucuagg    60
ggaauaua                                                              68

<210> SEQ ID NO 410
<211> LENGTH: 80
<212> TYPE: RNA
<213> ORGANISM: Homo sapiens and Mus musculus
<220> FEATURE:
<221> NAME/KEY: misc_RNA
<222> LOCATION: (1)..(80)
<223> OTHER INFORMATION: predicted precursor structure: mir-c33, 5' to
      3' sequence

<400> SEQUENCE: 410
ccuguugcca caaacccgua gauccgaacu ugugguauua guccgcacaa gcuuguaucu    60
auagguaugu gucuguuagg                                                 80

<210> SEQ ID NO 411
<211> LENGTH: 79
<212> TYPE: RNA
<213> ORGANISM: Homo sapiens and Mus musculus
<220> FEATURE:
<221> NAME/KEY: misc_RNA
<222> LOCATION: (1)..(79)
<223> OTHER INFORMATION: predicted precursor structure: mir-c34, 5' to
      3' sequence

<400> SEQUENCE: 411
aaggcagggg ugagggguug cgggaggagc cgggcggagg cugcggcuug cgcuucuccu    60
ggcucuccuc ccucuccuu                                                  79

<210> SEQ ID NO 412
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 412
cagccacacg gcaccgaatt cctcactaaa                                      30

<210> SEQ ID NO 413
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 413
gactagcttg gtgccgaatt cgcggttaaa                                      30

<210> SEQ ID NO 414
<211> LENGTH: 21
<212> TYPE: RNA
<213> ORGANISM: Caenorhabditis elegans

<400> SEQUENCE: 414
ucccugagac cucaagugug a                                               21

<210> SEQ ID NO 415
<211> LENGTH: 22
<212> TYPE: RNA
<213> ORGANISM: Drosophila melanogaster

<400> SEQUENCE: 415

```
ucccugagac ccuaacuugu ga                                              22

<210> SEQ ID NO 416
<211> LENGTH: 22
<212> TYPE: RNA
<213> ORGANISM: Homo sapiens and Mus musculus

<400> SEQUENCE: 416
ucccugagac ccuaacuugu ga                                              22

<210> SEQ ID NO 417
<211> LENGTH: 24
<212> TYPE: RNA
<213> ORGANISM: Homo sapiens and Mus musculus

<400> SEQUENCE: 417
ucccugagac ccuuuaaccu guga                                            24

<210> SEQ ID NO 418
<211> LENGTH: 22
<212> TYPE: RNA
<213> ORGANISM: Mus musculus

<400> SEQUENCE: 418
auaagacgag caaaaagcuu gu                                              22
```

IDENTIFICATION OF NOVEL GENES CODING FOR SMALL TEMPORAL RNAS

This Application is a divisional of U.S. Ser. No. 11/747,409 filed May 11, 2007, which is a divisional of U.S. Pat. No. 7,232,806 issued Jun. 19, 2007, which is a 371 of International Application PCT/EP2002/10881 filed Sep. 27, 2002, the disclosure of which is incorporated herein in its entirety by reference.

The present invention relates to novel small expressed (micro)RNA molecules associated with physiological regulatory mechanisms, particularly in developmental control.

In *Caenorhabditis elegans*, lin-4 and let-7 encode 22- and 21-nucleotide RNAs, respectively (1, 2), that function as key regulators of developmental timing (3-5). Because the appearance of these short RNAs is regulated during development, they are also referred to as "microRNAs" (miRNAs) or small temporal RNAs (stRNAs) (6). lin-4 and let-21 are the only known miRNAs to date.

Two distinct pathways exist in animals and plants in which 21- to 23-nucleotide RNAs function as post-transcriptional regulators of gene expression. Small interfering RNAs (siRNAs) act as mediators of sequence-specific mRNA degradation in RNA interference (RNAi) (7-11) whereas miRNAs regulate developmental timing by mediating sequence-specific repression of mRNA translation (3-5). siRNAs and miRNAs are excised from double-stranded RNA (dsRNA) precursors by Dicer (12, 13, 29), a multidomain RNase ill protein, thus producing RNA species of similar size. However, siRNAs are believed to be double-stranded (8, 11, 12), while miRNAs are single-stranded (6).

We show that many more short, particularly 21- and 22-nt expressed RNAs, termed microRNAs (miRNAs), exist in invertebrates and vertebrates, and that some of these novel RNAs, similar to let-7 RNA (6), are also highly conserved. This suggests that sequence-specific post-transcriptional regulatory mechanisms mediated by small RNAs are more general than previously appreciated.

The present invention relates to an isolated nucleic acid molecule comprising:
(a) a nucleotide sequence as shown in Table 1, Table 2, Table 3 or Table 4
(b) a nucleotide sequence which is the complement of (a),
(c) a nucleotide sequence which has an identity of at least 80%, preferably of at least 90% and more preferably of at least 99%, to a sequence of (a) or (b) and/or
(d) a nucleotide sequence which hybridizes under stringent conditions to a sequence of (a), (b) and/or (c).

In a preferred embodiment the invention relates to miRNA molecules and analogs thereof, to miRNA precursor molecules and to DNA molecules encoding miRNA or miRNA precursor molecules.

Preferably the identity of sequence (c) to a sequence of (a) or (b) is at least 90%, more preferably at least 95%. The determination of identity (percent) may be carried out as follows:

$$I = n : L$$

wherein I is the identity in percent, n is the number of identical nucleotides between a given sequence and a comparative sequence as shown in Table 1, Table 2, Table 3 or Table 4 and L is the length of the comparative sequence. It should be noted that the nucleotides A, C, G and U as depicted in Tables 1, 2, 3 and 4 may denote ribonucleotides, deoxyribonucleotides and/or other nucleotide analogs, e.g. synthetic non-naturally occurring nucleotide analogs. Further nucleobases may be substituted by corresponding nucleobases capable of forming analogous H-bonds to a complementary nucleic acid sequence, e.g. U may be s substituted by T.

Further, the invention encompasses nucleotide sequences which hybridize under stringent conditions with the nucleotide sequence as shown in Table 1, Table 2, Table 3 or Table 4, a complementary sequence thereof or a highly identical sequence. Stringent hybridization conditions comprise washing for 1 h in 1×SSC and 0.1% SOS at 45° C., preferably at 48° C. and more preferably at 50° C., particularly for 1 h in 0.2×SSC and 0.1% SDS.

The isolated nucleic acid molecules of the invention preferably have a length of from 18 to 100 nucleotides, and more preferably from 18 to 80 nucleotides. It should be noted that mature miRNAs usually have a length of 19-24 nucleotides, particularly 21, 22 or 23 nucleotides. The miRNAs, however, may be also provided as a precursor which usually has a length of 50-90 nucleotides, particularly 60-80 nucleotides. It should be noted that the precursor may be produced by processing of a primary transcript which may have a length of >100 nucleotides.

The nucleic acid molecules may be present in single-stranded or double-stranded form. The miRNA as such is usually a single-stranded molecule, while the mi-precursor is usually an at least partially self-complementary molecule capable of forming double-stranded portions, e.g. stem- and loop-structures. DNA molecules encoding the miRNA and miRNA precursor molecules. The nucleic acids may be selected from RNA, DNA or nucleic acid analog molecules, such as sugar- or backbone-modified ribonucleotides or deoxyribonucleotides. It should be noted, however, that other nucleic analogs, such as peptide nucleic acids (PNA) or locked nucleic acids (LNA), are also suitable.

In an embodiment of the invention the nucleic acid molecule is an RNA- or DNA molecule, which contains at least one modified nucleotide analog, i.e. a naturally occurring ribonucleotide or deoxyribonucleotide is substituted by a non-naturally occurring nucleotide. The modified nucleotide analog may be located for example at the 5'-end and/or the 3'-end of the nucleic acid molecule.

Preferred nucleotide analogs are selected from sugar- or backbone-modified ribonucleotides. It should be noted, however, that also nucleobase-ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O— and N-alkylated nucleotides, e.g. N6-methyl adenosine are suitable. In preferred sugar-modified ribonucleotides the 2'-OH-group is replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. In preferred backbone-modified ribonucleotides the phosphoester group connecting to adjacent ribonucleotides is replaced by a modified group, e.g. of phosphothioate group. It should be noted that the above modifications may be combined.

The nucleic acid molecules of the invention may be obtained by chemical synthesis methods or by recombinant methods, e.g. by enzymatic transcription from synthetic DNA-templates or from DNA-plasmids isolated from recombinant organisms. Typically phage RNA-polymerases are used for transcription, such as T7, T3 or SP6 RNA-polymerases.

The invention also relates to a recombinant expression vector comprising a recombinant nucleic acid operatively linked to an expression control sequence, wherein expression, i.e. transcription and optionally further processing results in a miRNA-molecule or miRNA precursor molecule as described above. The vector is preferably a DNA-vector, e.g. a viral vector or a plasmid, particularly an expression vector suitable for nucleic acid expression in eukaryotic, more particularly mammalian cells. The recombinant nucleic acid contained in said vector may be a sequence which results in the transcription of the miRNA-molecule as such, a precursor or a primary transcript thereof, which may be further processed to give the miRNA-molecule.

Further, the invention relates to diagnostic or therapeutic applications of the claimed nucleic acid molecules. For example, miRNAs may be detected in biological samples, e.g. in tissue sections, in order to determine and classify certain cell types or tissue types or miRNA-associated pathogenic disorders which are characterized by differential expression of miRNA-molecules or miRNA-molecule patterns. Further, the developmental stage of cells may be classified by determining temporarily expressed miRNA-molecules.

Further, the claimed nucleic acid molecules are suitable for therapeutic applications. For example, the nucleic acid molecules may be used as modulators or targets of developmental processes or disorders associated with developmental dysfunctions, such as cancer. For example, miR-15 and miR-16 probably function as tumor-suppressors and thus expression or delivery of these RNAs or analogs or precursors thereof to tumor cells may provide therapeutic efficacy, particularly against leukemias, such as B-cell chronic lymphocytic leukemia (B-CLL). Further, miR-10 is a possible regulator of the translation of Hox Genes, particularly Hox 3 and Hox 4 (or Scr and Dfd in Drosophila).

In general, the claimed nucleic acid molecules may be used as a modulator of the expression of genes which are at least partially complementary to said nucleic acid. Further, miRNA molecules may act as target for therapeutic screening procedures, e.g. inhibition or activation of miRNA molecules might modulate a cellular differentiation process, e.g. apoptosis.

Furthermore, existing miRNA molecules may be used as starting materials for the manufacture of sequence-modified miRNA molecules, in order to modify the target-specificity thereof, e.g. an oncogene, a multidrug-resistance gene or another therapeutic target gene. The novel engineered miRNA molecules preferably have an identity of at least 80% to the starting miRNA, e.g. as depicted in Tables 1, 2, 3 and 4. Further, miRNA molecules can be modified, in order that they are symetrically processed and then generated as double-stranded siRNAs which are again directed against therapeutically relevant targets.

Furthermore, miRNA molecules may be used for tissue reprogramming procedures, e.g. a differentiated cell line might be transformed by expression of miRNA molecules into a different cell type or a stem cell.

For diagnostic or therapeutic applications, the claimed RNA molecules are preferably provided as a pharmaceutical composition. This pharmaceutical composition comprises as an active agent at least one nucleic acid molecule as described above and optionally a pharmaceutically acceptable carrier.

The administration of the pharmaceutical composition may be carried out by known methods, wherein a nucleic acid is introduced into a desired target cell in vitro or in vivo.

Commonly used gene transfer techniques include calcium phosphate, DEAE-dextran, electroporation and microinjection and viral methods [30, 31, 32, 33, 34]. A recent addition to this arsenal of techniques for the introduction of DNA into cells is the use of cationic liposomes [35].

Commercially available cationic lipid formulations are e.g. Tfx 50 (Promega) or Lipofectamiri 2000 (Life Technologies).

The composition may be in form of a solution, e.g. an injectable solution, a cream, ointment, tablet, suspension or the like. The composition may be administered in any suitable way, e.g. by injection, by oral, topical, nasal, rectal application etc. The carrier may be any suitable pharmaceutical carrier. Preferably, a carrier is used, which is capable of increasing the efficacy of the RNA molecules to enter the target-cells. Suitable examples of such carriers are liposomes, particularly cationic liposomes.

Further, the invention relates to a method of identifying novel microRNA-molecules and precursors thereof, in eukaryotes, particularly in vertebrates and more particularly in mammals, such as humans or mice. This method comprises: ligating 5'- and 3'-adapter-molecules to the end of a size-fractionated RNA-population, reverse transcribing said adapter-ligated RNA-population, and characterizing said reverse transcribed RNA-molecules, e.g. by amplification, concatamerization, cloning and sequencing.

A method as described above already has been described in (8), however, for the identification of siRNA molecules. Surprisingly, it was found now that the method is also suitable for identifying the miRNA molecules or precursors thereof as claimed in the present application.

Further, it should be noted that as 3'-adaptor for derivatization of the 3'-OH group not only 4-hydroxymethylbenzyl but other types of derivatization groups, such as alkyl, alkyl amino, ethylene glycol or 3'-deoxy groups are suitable.

Further, the invention shall be explained in more detail by the following Figures and Examples:

FIGURE LEGENDS

FIG. 1A. Expression of *D. melanogaster* miRNAs. Northern blots of total RNA isolated from staged populations of *D. melanogaster* were probed for the indicated miRNAs. The position of 76-nt val-tRNA is also indicated on the blots. 5S rRNA serves as loading control. E, embryo; L, larval stage; P, pupae; A, adult; S2, Schneider-2 cells. It should be pointed out, that S2 cells are polyclonal, derived from an unknown subset of embryonid tissues, and may have also lost some features of their tissue of origin while maintained in culture. miR-3 to miR-6 RNAs were not detectable in S2 cells (data not shown). miR-14 was not detected by Northern blotting and may be very weakly expressed, which is consistent with its cloning frequency. Similar miRNA sequences are difficult to distinguish by Northern blotting because of potential cross-hybridization of probes.

Figure 1B:
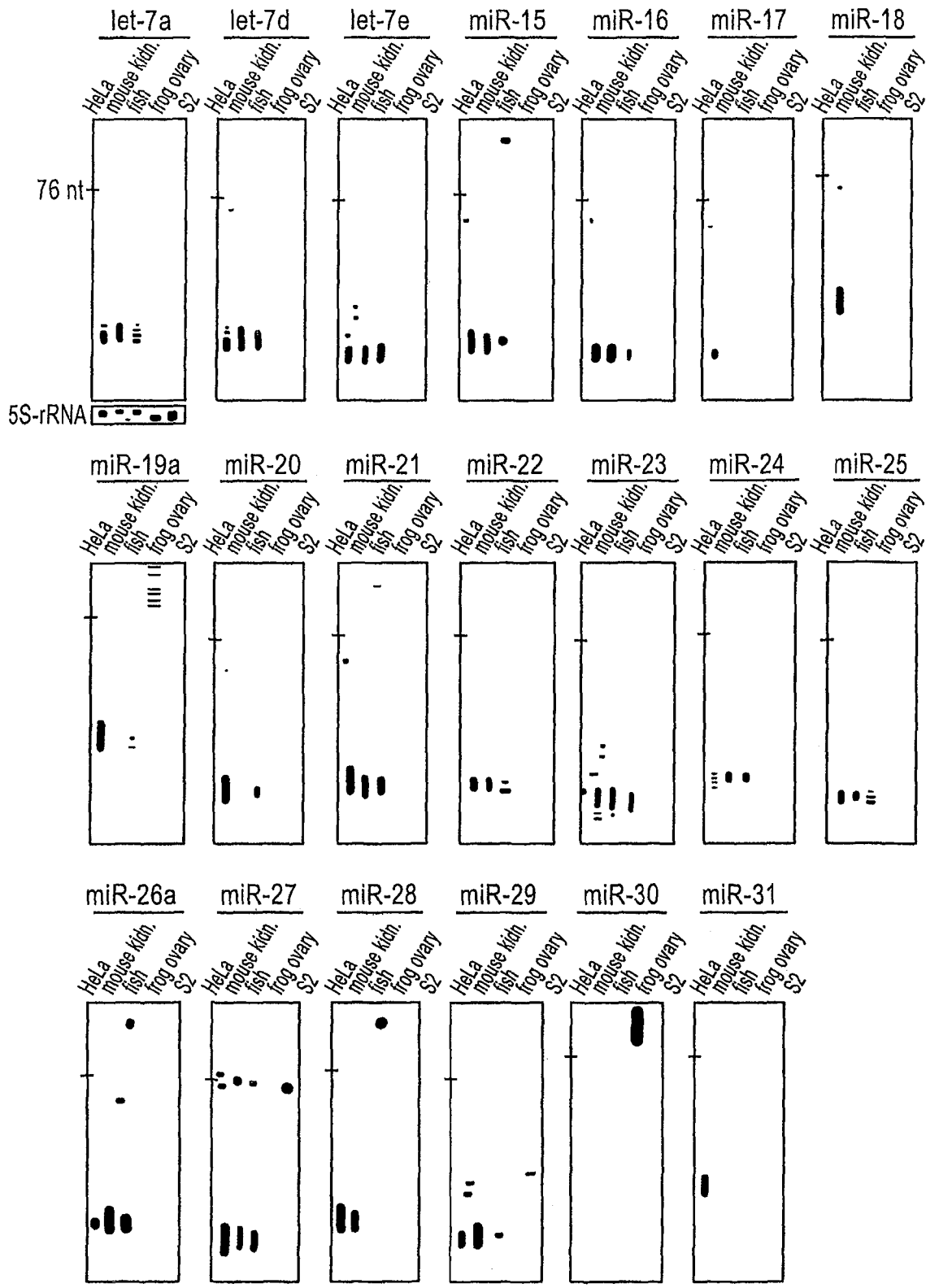

FIG. 1B: Expression of vertebrate miRNAs. Northern blots of total RNA isolated from HeLa cells, mouse kidneys, adult zebrafish, frog ovaries, and S2 cells were probed for the indicated miRNAs. The position of 76-nt val-tRNA is also indicated on the blots. 5S rRNA from the preparations of total RNA from the indicated species is also shown. The gels used for probing of miR-18, miR-19a, miR-30, and miR-31 were not run as far as the other gels (see tRNA marker position). miR-32 and miR-33 were not detected by Northern blotting, which is consistent with their low cloning frequency. Oligodeoxynucleotides used as Northern probes were:

```
                                           (SEQ ID NO: 1)
let-7a, 5' TACTATACAACCTACTACCTCAATTTGCC;

(SEQ ID NO: 2)
let-7d, 5' ACTATGCAACCTACTACCTCT;

(SEQ ID NO: 3)
let-7e, 5' ACTATACAACCTCCTACCTCA;

(SEQ ID NO: 4)
D. melanogaster val-tRNA, 5' TGGTGTTTCCGCCCGGGAA;
``` miR-1, 5' TGGAATGTAAAGAAGTATGGAG; (SEQ ID NO: 5)

miR-2b, 5' GCTCCTCAAAGCTGGCTGTGATA; (SEQ ID NO: 6)

miR-3, 5' TGAGACACACTTTGCCCAGTGA; (SEQ ID NO: 7)

miR-4, 5' TCAATGGTTGTCTAGCTTTAT; (SEQ ID NO: 8)

miR-5, 5' CATATCACAACGATCGTTCCTTT; (SEQ ID NO: 9)

miR-6, 5' AAAAAGAACAGCCACTGTGATA; (SEQ ID NO: 10)

miR-7, 5' TGGAAGACTAGTGATTTTGTTGT; (SEQ ID NO: 11)

miR-8, 5' GACATCTTTACCTGACAGTATTA; (SEQ ID NO: 12)

miR-9, 5' TCATACAGCTAGATAACCAAAGA; (SEQ ID NO: 13)

miR-10, 5' ACAAATTCGGATCTACAGGGT; (SEQ ID NO: 14)

miR-11, 5' GCAAGAACTCAGACTGTGATG; (SEQ ID NO: 15)

miR-12, 5' ACCAGTACCTGATGTAATACTCA; (SEQ ID NO: 16)

miR-13a, 5' ACTCGTCAAAATGGCTGTGATA; (SEQ ID NO: 17)

miR-14, 5' TAGGAGAGAGAAAAAGACTGA; (SEQ ID NO: 18)

miR-15, 5' TAGCAGCACATAATGGTTTGT; (SEQ ID NO: 19)

miR-16, 5' GCCAATATTTACGTGCTGCTA; (SEQ ID NO: 20)

miR-17, 5' TACAAGTGCCTTCACTGCAGTA; (SEQ ID NO: 21)

miR-18, 5' TATCTGCACTAGATGCACCTTA; (SEQ ID NO: 22)

miR-19a, 5' TCAGTTTTGCATAGATTTGCACA; (SEQ ID NO: 23)

miR-20, 5' TACCTGCACTATAAGCACTTTA; (SEQ ID NO: 24)

miR-21, 5' TCAACATCAGTCTGATAAGCTA; (SEQ ID NO: 25)

miR-22, 5' ACAGTTCTTCAACTGGCAGCTT; (SEQ ID NO: 26)

miR-23, 5' GGAAATCCCTGGCAATGTGAT; (SEQ ID NO: 27)

miR-24, 5' CTGTTCCTGCTGAACTGAGCCA; (SEQ ID NO: 28)

miR-25, 5' TCAGACCGAGACAAGTGCAATG; (SEQ ID NO: 29)

miR-26a, 5' AGCCTATCCTGGATTACTTGAA; (SEQ ID NO: 30)

miR-27; 5' AGCGGAACTTAGCCACTGTGAA; (SEQ ID NO: 31)

miR-28, 5' CTCAATAGACTGTGAGCTCCTT; (SEQ ID NO: 32)

miR-29, 5' AACCGATTTCAGATGGTGCTAG; (SEQ ID NO: 33)

miR-30, 5' GCTGCAAACATCCGACTGAAAG; (SEQ ID NO: 34)

miR-31, 5' CAGCTATGCCAGCATCTTGCCT; (SEQ ID NO: 35)

miR-32, 5' GCAACTTAGTAATGTGCAATA; (SEQ ID NO: 36)

miR-33, 5' TGCAATGCAACTACAATGCACC. (SEQ ID NO: 37)

Figure 2:
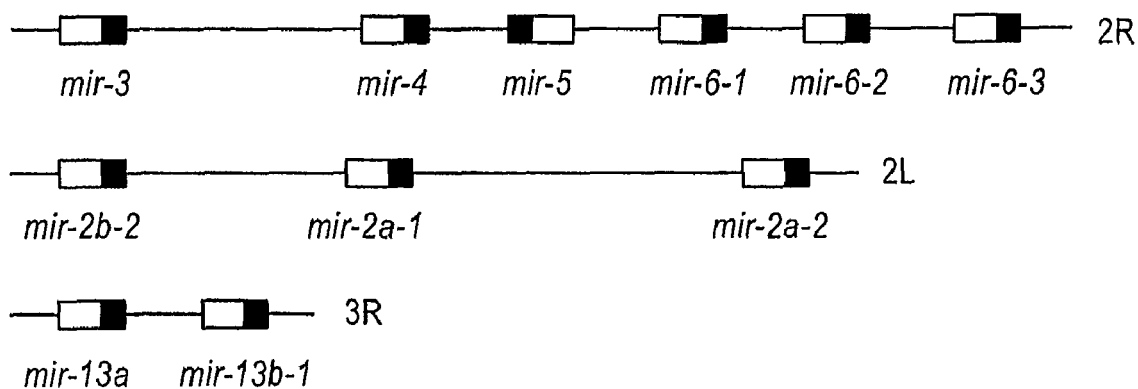
Figure 2:
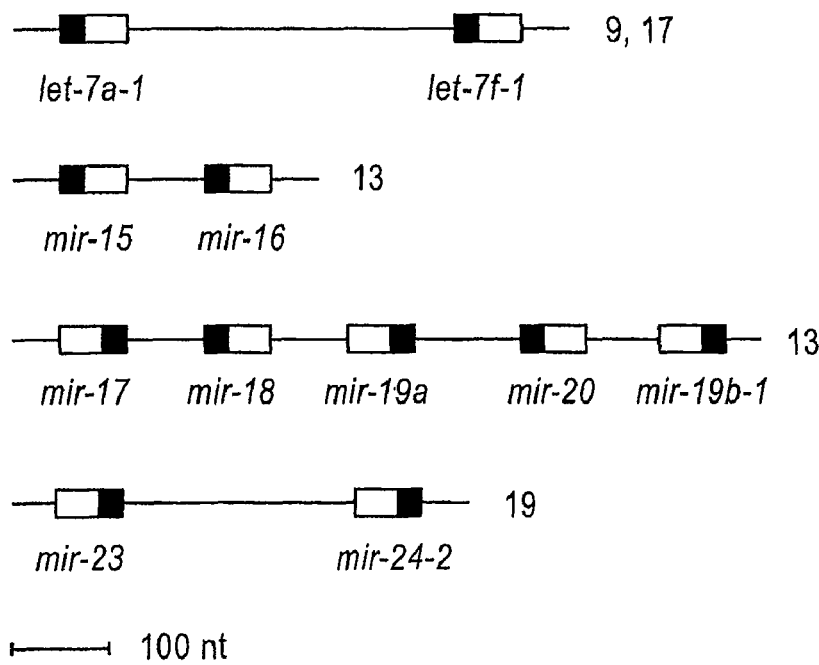

FIG. 2. Genomic organization of miRNA gene clusters. The precursor structure is indicated as box and the location of the miRNA within the precursor is shown in gray; the chromosomal location is also indicated to the right. (A) *D. melanogaster* miRNA gene clusters. (B) Human miRNA gene clusters. The cluster of let-7a-1 and let-7f-1 is separated by 26500 nt from a copy of let-7d on chromosome 9 and 17. A cluster of let-7a-3 and let-7b, separated by 938 nt on chromosome 22, is not illustrated.

Figure 3:
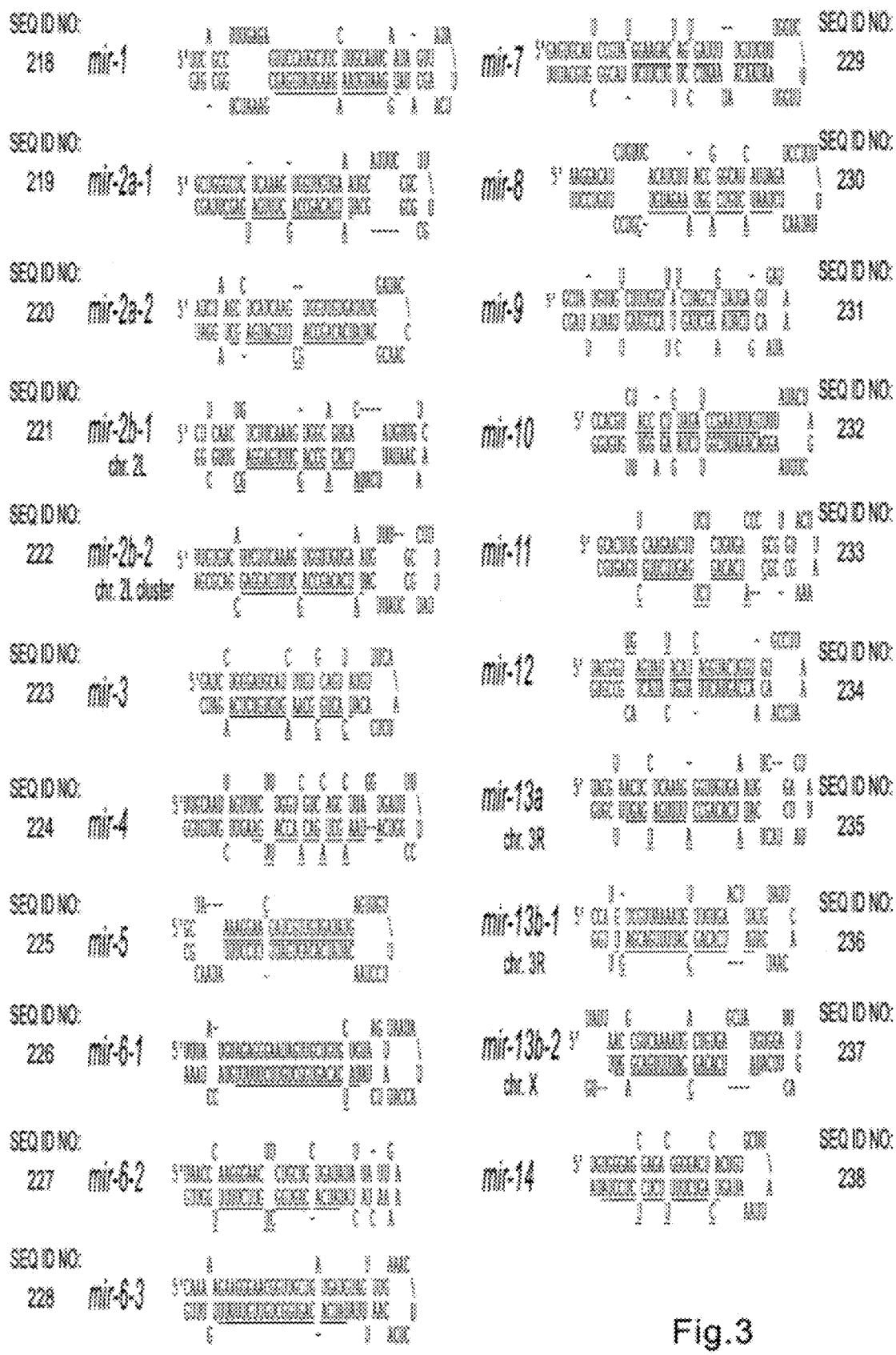

FIG. 3. Predicted precursor structures of *D. melanogaster* miRNAs. RNA secondary structure prediction was performed using mfold version 3.1 [28] and manually refined to accommodate G/U wobble base pairs in the helical segments. The miRNA sequence is underlined. The actual size of the stem-loop structure is not known experimentally and may be slightly shorter or longer than represented. Multicopy miRNAs and their corresponding precursor structures are also shown.

Figure 4:
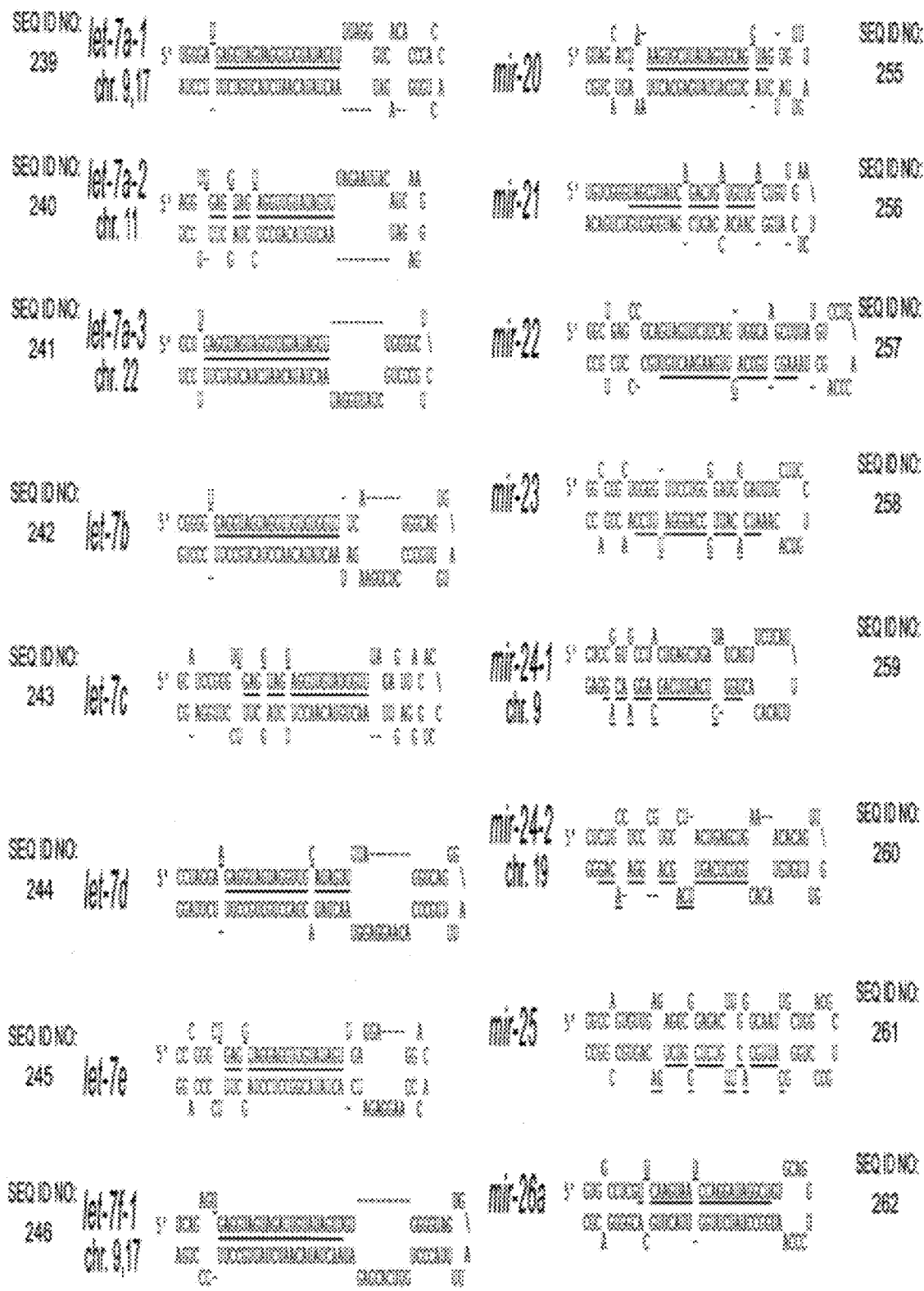

FIG. 4. Predicted precursor structures of human miRNAs. For legend, see FIG. 3.

Figure 5:
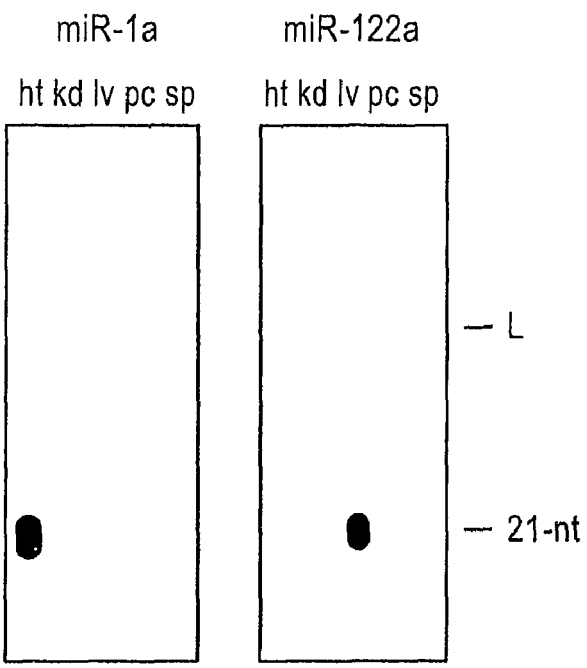
Figure 5:
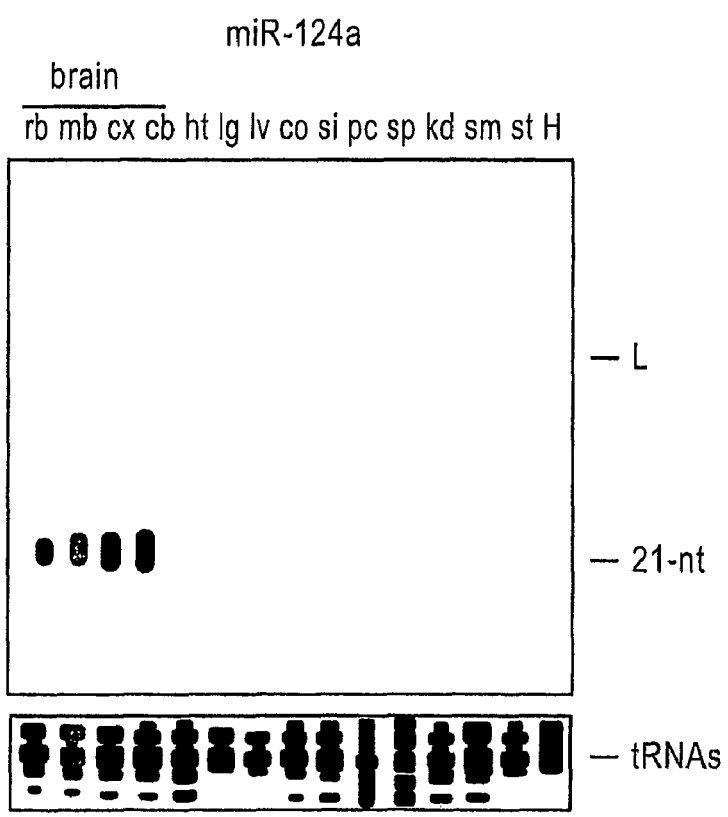
Figure 5:
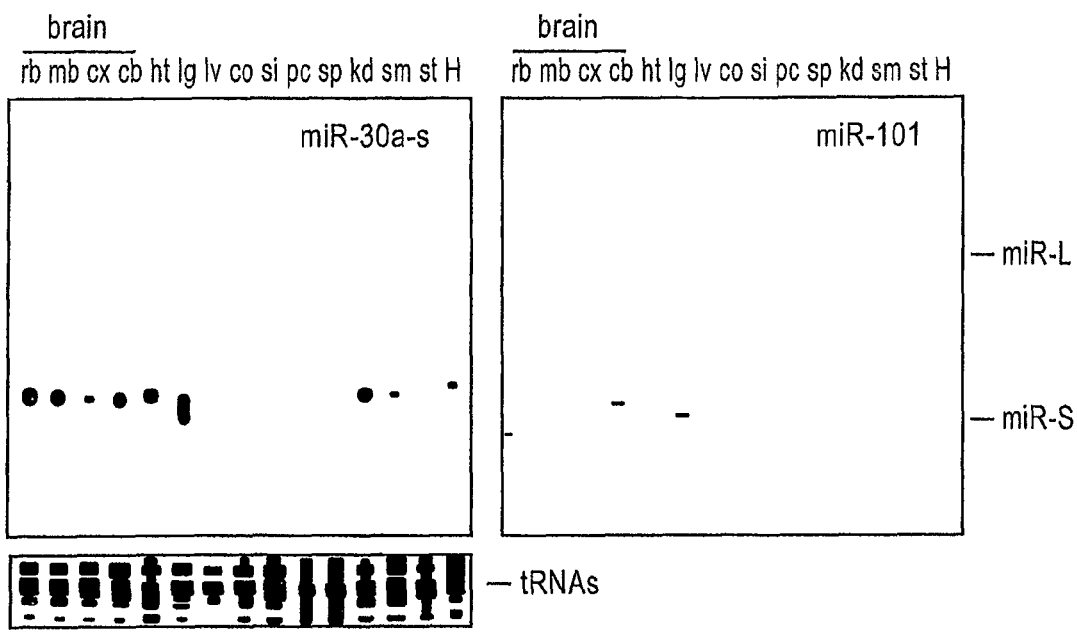
Figure 5:
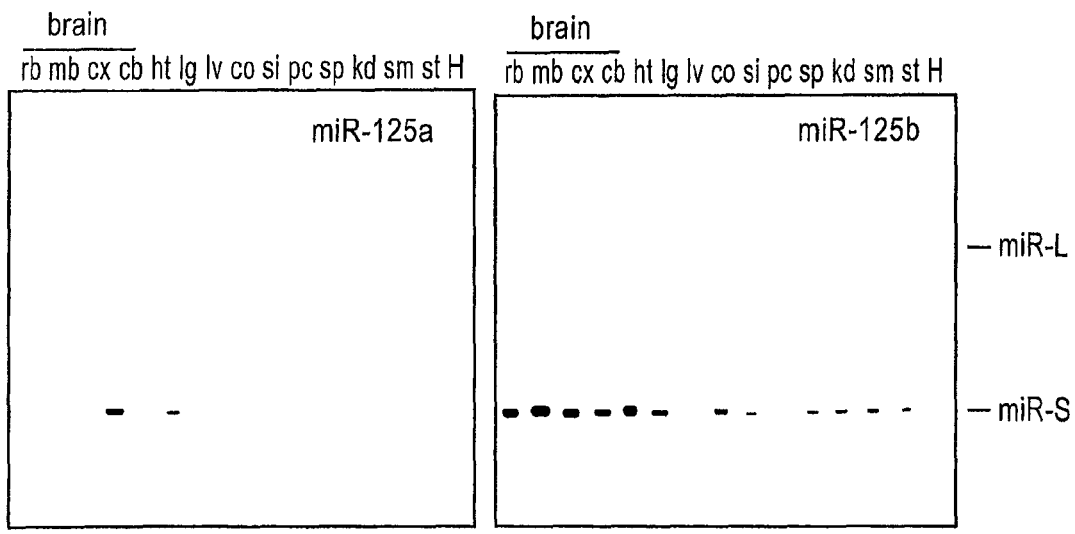
Figure 5:
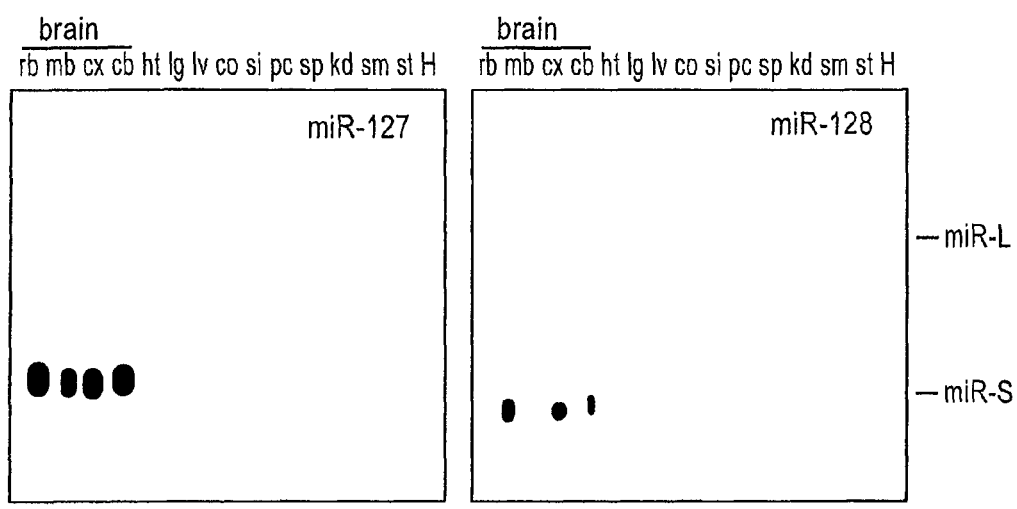
Figure 5:
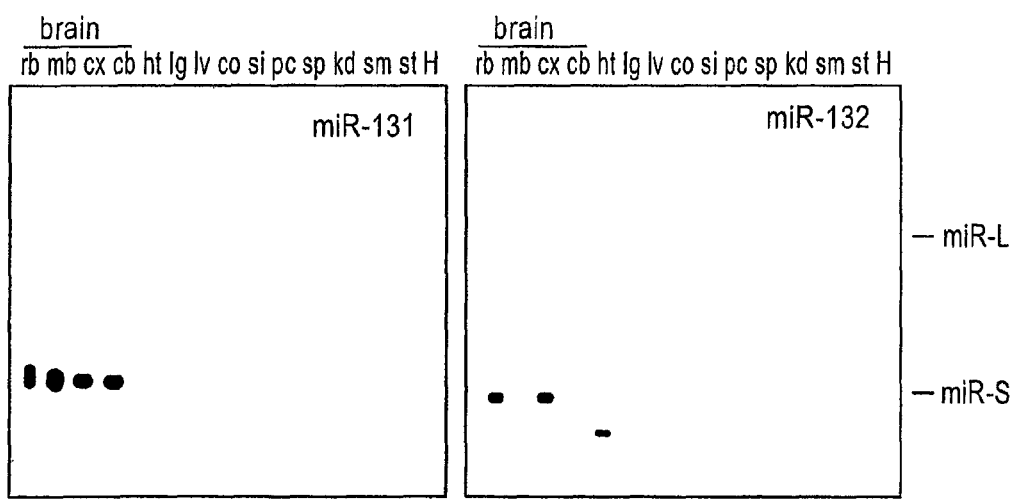
Figure 5:
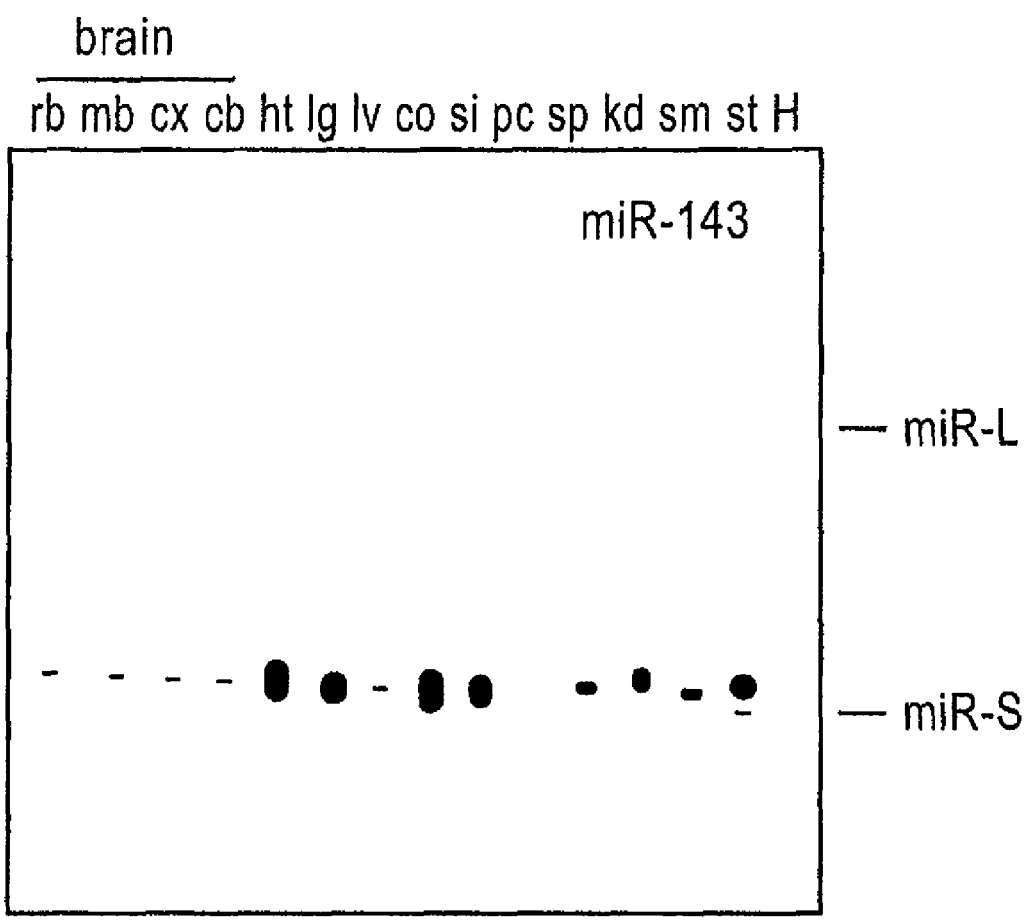

FIG. 5. Expression of novel mouse miRNAs. Northern blot analysis of novel mouse miRNAs. Total RNA from different mouse tissues was blotted and probed with a 5'-radiolabeled oligodeoxynucleotide complementary to the indicated miRNA. Equal loading of total RNA on the gel was verified by ethidium bromide staining prior to transfer; the band representing tRNAs is shown. The fold-back precursors are indicated with capital L. Mouse brains were dissected into midbrain, mb, cortex, cx, cerebellum, cb. The rest of the brain, rb, was also used. Other tissues were heart, ht, lung, lg, liver, lv, colon, co, small intestine, si, pancreas, pc, spleen, sp, kidney, kd, skeletal muscle, sm, stomach, st, H, human Hela SS3 cells. Oligodeoxynucleotides used as Northern probes were:

miR-1a, CTCCATACTTCTTTACATTCCA; (SEQ ID NO: 38)

miR-30b, GCTGAGTGTAGGATGTTTACA; (SEQ ID NO: 39)

miR-30a-s, GCTTCCAGTCGAGGATGTTTACA; (SEQ ID NO: 40)

miR-99b, CGCAAGGTCGGTTCTACGGGTG; (SEQ ID NO: 41)

miR-101, TCAGTTATCACAGTACTGTA; (SEQ ID NO: 42)

miR-122a, ACAAACACCATTGTCACACTCCA; (SEQ ID NO: 43)

```
                                            (SEQ ID NO: 44)
miR-124a,  TGGCATTCACCGCGTGCCTTA;

(SEQ ID NO: 45)
miR-125a,  CACAGGTTAAAGGGTCTCAGGGA;

(SEQ ID NO: 46)
miR-125b,  TCACAAGTTAGGGTCTCAGGGA;

(SEQ ID NO: 47)
miR-127,   AGCCAAGCTCAGACGGATCCGA;

(SEQ ID NO: 48)
miR-128,   AAAAGAGACCGGTTCACTCTGA;

(SEQ ID NO: 49)
miR-129,   GCAAGCCCAGACCGAAAAAAG;

(SEQ ID NO: 50)
miR-130,   GCCCTTTTAACATTGCACTC;

(SEQ ID NO: 51)
miR-131,   ACTTTCGGTTATCTAGCTTTA;

(SEQ ID NO: 52)
miR-132,   ACGACCATGGCTGTAGACTGTTA;

(SEQ ID NO: 53)
miR-143,   TGAGCTACAGTGCTTCATCTCA.
```

Figure 6:
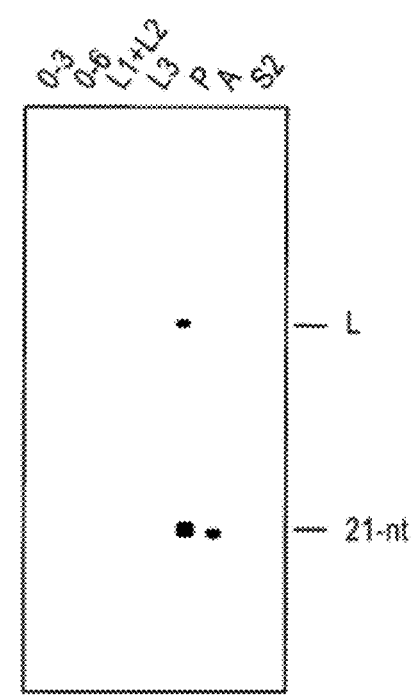

FIG. 6. Potential orthologs of lin-4 stRNA. (A) Sequence alignment of *C. elegans* lin-4 stRNA with mouse miR-125a and miR-125b and the *D. melanogaster* miR-125. Differences are highlighted by gray boxes. (B) Northern blot of total RNA isolated from staged populations of *D. melanogaster*, probed for miR-125. E, embryo; L, larval stage; P, pupae; A, adult; S2, Schneider-2 cells.

Figure 7:
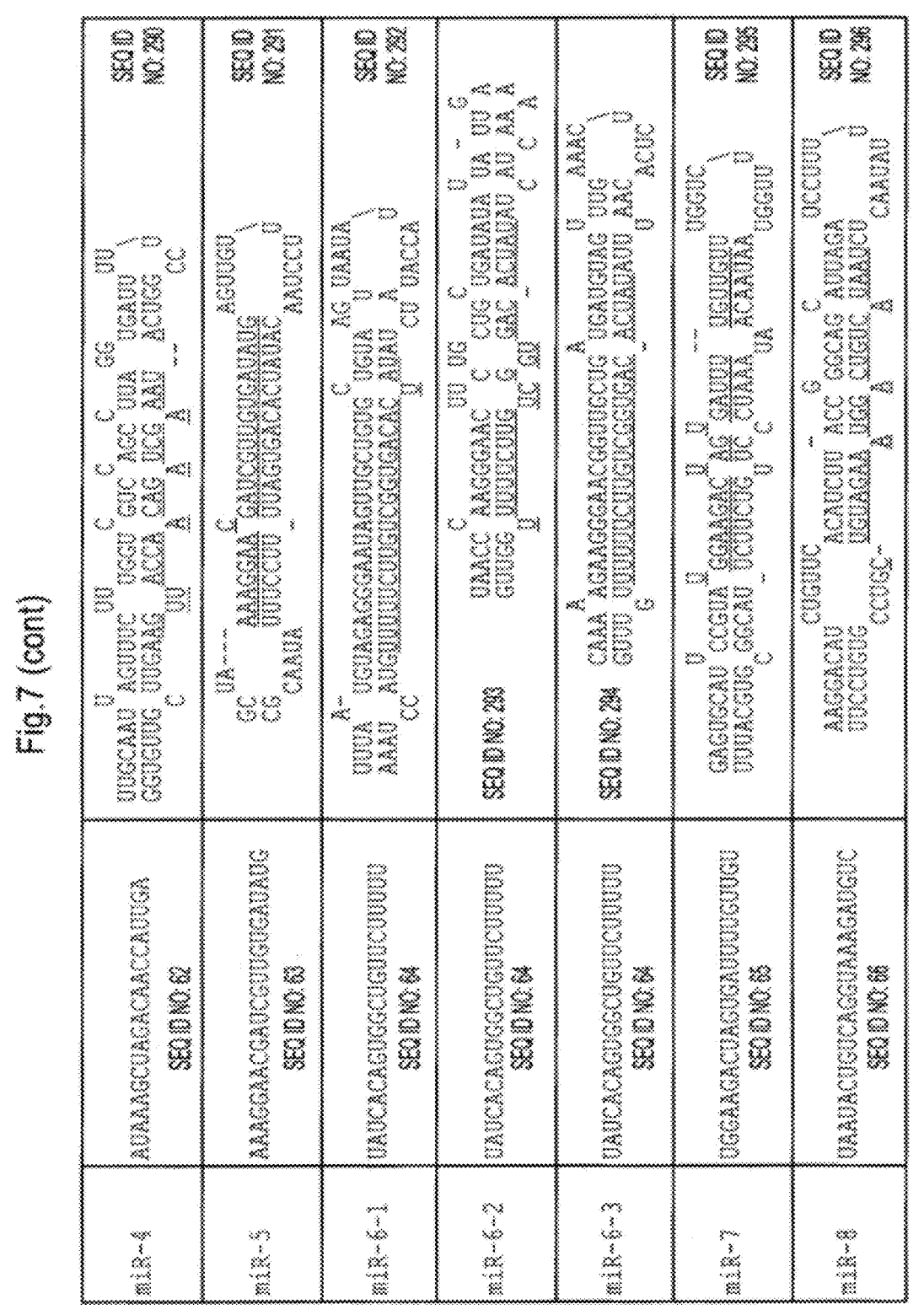
Figure 7:
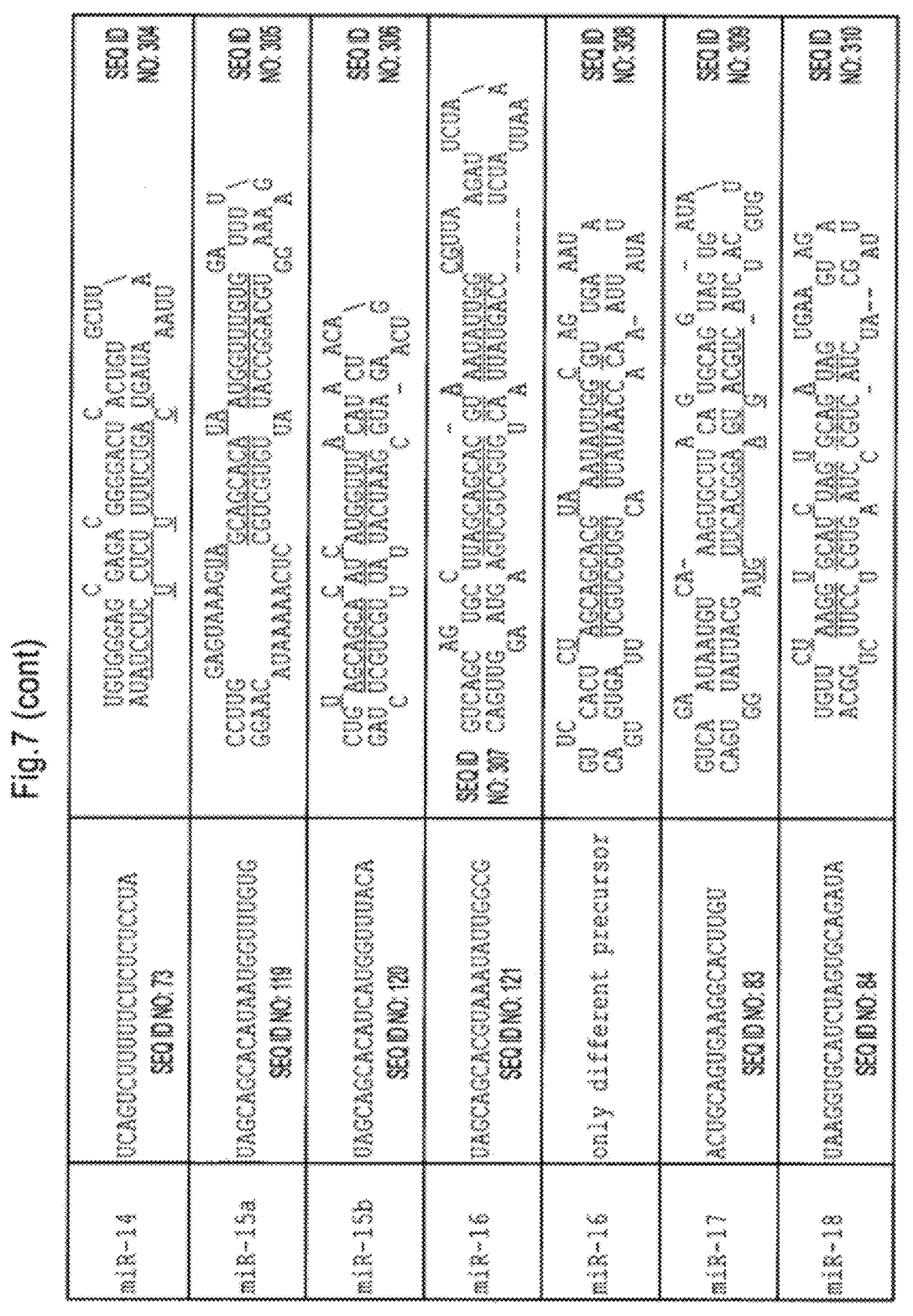
Figure 7:
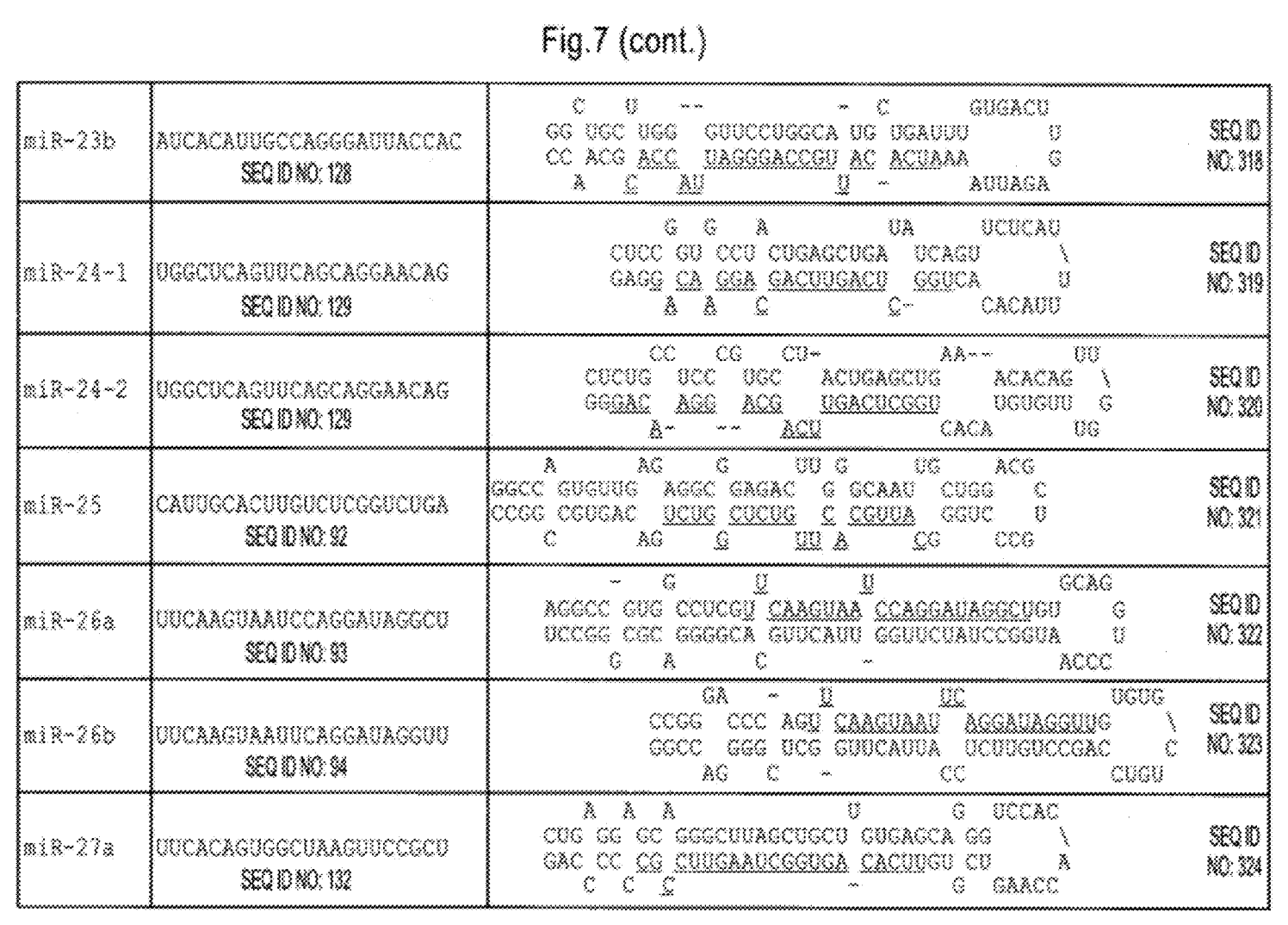

FIG. 7. Predicted precursor structures of miRNAs, sequence accession numbers and homology information. RNA secondary structure prediction was performed using mfold version 3.1 and manually refined to accommodate G/U wobble base pairs in the helical segments. Dashes were inserted into the secondary structure presentation when asymmetrically bulged nucleotides had to be accommodated. The excised miRNA sequence is underlined. The actual size of the stem-loop structure is not known experimentally and may be slightly shorter or longer than represented. Multicopy miRNAs and their corresponding precursor structures are also shown. In cases where no mouse precursors were yet which correspond to *D. melanogaster* or human sequences are included. Published *C. elegans* miRNAs [36, 37] are also included in the table. A recent set of new HeLa cell miRNAs is also indicated [46]. If several ESTs were retrieved for one organism in the database, only those with different precursor sequences are listed: miRNA homologs found in other species are indicated. Chromosomal location and sequence accession numbers, and clusters of miRNA genes are indicated: Sequences from cloned miRNAs were searched against mouse and human in GenBank (including trace data), and against *Fugu rubripes* and *Dania rerio* at www.jgi.doe.gov and www.sanger.ac.uk, respectively.

EXAMPLE 1

Micrornas From *D. melanogaster* And Human

We previously developed a directional cloning procedure to isolate siRNAs after processing of long dsRNAs in *Drosophila melanogaster* embryo lysate (8). Briefly, 5' and 3' adapter molecules were ligated to the ends of a size-fractionated RNA population, followed by reverse transcription, PCR amplification, concatamerization, cloning and sequencing. This method, originally intended to isolate siRNAs, led to the simultaneous identification of 14 novel 20- to 23-nt short RNAs which are encoded in the *D. melanogaster* genome and which are expressed in 0 to 2 h embryos (Table 1). The method was adapted to clone RNAs in a similar size range from HeLa cell total RNA (14), which led to the identification of 19 novel human stRNAs (Table 2), thus providing further evidence for the existence of a large class of small RNAs with potential regulatory roles. According to their small size, we refer to these novel RNAs as microRNAs or miRNAs. The miRNAs are abbreviated as miR-1 to miR-33, and the genes encoding miRNAs are named mir-1 to mir-33. Highly homologous miRNAs are classified by adding a lowercase letter, followed by a dash and a number for designating multiple genomic copies of a mir gene.

The expression and size of the cloned, endogenous short RNAs was also examined by Northern blotting (FIG. 1, Table 1 and 2). Total RNA isolation was performed by acid guanidinium thiocyanate-phenol-chloroform extraction [45]. Northern analysis was performed as described [1], except that the total RNA was resolved on a 15% denaturing polyacrylamide gel, transferred onto Hybond-N+membrane (Amersham Pharmacia Biotech), and the hybridization and wash steps were performed at 50° C. Oligodeoxynucleotides used as Northern probes were 5'-32P-phosphorylated, complementary to the miRNA sequence and. 20 to 25 nt in length.

5S rRNA was detected by ethidium staining of polyacrylamide gels prior to transfer. Blots were stripped by boiling in 0.1% aqueous sodium dodecylsulfate/0.1×SSC (15 mM sodium chloride, 1.5 mM sodium citrate, pH 7.0) for 10 min, and were re-probed up to 4 times until the 21-nt signals became too weak for detection. Finally, blots were probed for val-tRNA as size marker.

For analysis of *D. melanogaster* RNAs, total RNA was prepared from different developmental stages, as well as cultured Schneider-2 (S2) cells, which originally derive from 20-24 h *D. melanogaster* embryos [15] (FIG. 1, Table 1). miR-3 to miR-7 are expressed only during embryogenesis and not at later developmental stages. The temporal expression of miR-1, miR-2 and miR-8 to miR-13 was less restricted. These miRNAs were observed at all developmental stages though significant variations in the expression levels were sometimes observed. Interestingly, miR-1, miR-3 to miR-6, and miR-8 to miR-11 were completely absent from cultured Schneider-2 (S2) cells, which were originally derived from 20-24 h *D. melanogaster* embryos [15], while. miR-2, miR-7, miR-12, and miR-13 were present in S2 cells, therefore indicating cell type-specific miRNA expression. miR-1, miR-8, and miR-12 expression patterns are similar to those of lin-4 stRNA in *C. elegans*, as their expression is strongly upregulated in larvae and sustained to adulthood [16]. miR-9 and miR-11 are present at all stages but are strongly reduced in the adult which may reflect a maternal contribution from germ cells or expression in one sex only.

The mir-3 to mir-6 genes are clustered (FIG. 2A), and mir-6 is present as triple repeat with slight variations in the mir-6 precursor sequence but not in the miRNA sequence itself: The expression profiles of miR-3 to miR-6 are highly similar (Table 1), which -suggests that a single embryo-specific precursor transcript may give rise to the different miRNAs, or that the same enhancer regulates miRNA-specific promoters. Several other fly miRNAs are also found in gene clusters (FIG. 2A).

The expression of HeLa cell miR-15 to miR-33 was examined by Northern blotting using HeLa cell total RNA, in addition to total RNA prepared from mouse kidneys, adult zebrafish, *Xenopus laevis* ovary, and *D. melanogaster* S2 cells. (FIG. 1B, Table 2). miR-15 and miR-16 are encoded in a gene cluster (FIG. 2B) and are detected in mouse kidney, fish, and very weakly in frog ovary, which may result from miRNA expression in somatic ovary tissue rather than oocytes. mir-17 to mir-20 are also clustered (FIG. 2B), and are expressed in HeLa cells and fish, but undetectable in mouse kidney and frog ovary (FIG. 1, Table 2), and therefore represent a likely case of tissue-specific miRNA expression.

The majority of vertebrate and invertebrate miRNAs identified in this study are not related by sequence, but a few exceptions, similar to the highly conserved let-7 RNA [6], do exist. Sequence analysis of the D. melanogaster miRNAs revealed four such examples of sequence conservation between invertebrates and vertebrates. miR-1 homologs are encoded in the genomes of C. elegans, C. briggsae, and humans, and are found in cDNAs from zebrafish, mouse, cow and human. The expression of mir-1 was detected by Northern blotting in total RNA from adult zebrafish and C. elegans, but not in total RNA from HeLa cells or mouse kidney (Table 2 and data not shown). Interestingly, while mir-1 and let-7 are expressed both in adult flies (FIG. 1A) [6] and are both undetected in S2 cells, miR-1 is, in contrast to let-7, undetectable in HeLa cells. This represents another case of tissue-specific expression of a miRNA, and indicates that miRNAs may not only play a regulatory role in developmental timing, but also in tissue specification. miR-7 homologs were found by database searches in mouse and human genomic and expressed sequence tag sequences (ESTs). Two mammalian miR-7 variants are predicted by sequence analysis in mouse and human, and were detected by Northern blotting in HeLa cells and fish, but not in mouse kidney (Table 2). Similarly, we identified mouse and human miR-9 and miR-10 homologs by database searches but only detected mir-10 expression in mouse kidney.

The identification of evolutionary related miRNAs, which have already acquired multiple sequence mutations, was not possible by standard bioinformatic searches. Direct comparison of the D. melanogaster miRNAs with the human miRNAs identified an 11-nt segment shared between D. melanogaster miR-6 and HeLa miR-27, but no further relationships were detected. One may speculate that most miRNAs only act on a single target and therefore allow for rapid evolution by covariation, and that highly conserved miRNAs act on more than one target sequence, and therefore have a reduced probability for evolutionary drift by covariation [6]. An alternative interpretation is that the sets of miRNAs from D. melanogaster and humans are fairly incomplete and that many more miRNAs remain to be discovered, which will provide the missing evolutionary links.

lin-4 and let-7 stRNAs were predicted to be excised from longer transcripts that contain approximately 30 base-pair stem-loop structures [1, 6]. Database searches for newly identified miRNAs revealed that all miRNAs are flanked by sequences that have the potential to form stable stem-loop structures (FIGS. 3 and 4). In many cases, we were able to detect the predicted, approximately 70-nt precursors by Northern blotting (FIG. 1).

Some miRNA precursor sequences were also identified in mammalian cDNA (EST) databases [27], indicating that primary transcripts longer than 70-nt stem-loop precursors do also exist. We never cloned a 22-nt RNA complementary to any of the newly identified miRNAs, and it is as yet unknown how the cellular processing machinery distinguishes between the miRNA and its complementary strand. Comparative analysis of the precursor stem-loop structures indicates that the loops adjacent to the base-paired miRNA segment can be located on either side of the miRNA sequence (FIGS. 3 and 4), suggesting that the 5' or 3' location of the stem-closing loop is not the determinant of miRNA excision. It is also unlikely that the structure, length or stability of the precursor stem is the critical determinant as the base-paired structures are frequently imperfect and interspersed by less stable, non-Watson-Crick base pairs such as G/A, U/U, C/U, A/A, and G/U wobbles. Therefore, a sequence-specific recognition process is a likely determinant for miRNA excision, perhaps mediated by members of the Argonaute (rde-1/ago1/piwi) protein family. Two members of this family, alg-1 and alg-2, have recently been shown to be critical for stRNA processing in C. elegans [13]. Members of the Argonaute protein family are also involved in RNAi and PTGS. In D. melanogaster, these include argonaute2, a component of the siRNA-endonuclease complex (RISC) [17], and its relative aubergine, which is important for silencing of repeat genes [18]. In other species, these include rde-1, argonautel, and qde-2, in C. elegans [19], Arabidopsis thaliana [20], and Neurospora crassa [21], respectively. The Argonaute protein family therefore represents, besides the RNase III Dicer [12, 13], another evolutionary link between RNAI and miRNA maturation.

Despite advanced genome projects, computer-assisted detection of genes encoding functional RNAs remains problematic [22]. Cloning of expressed, so short functional RNAs, similar to EST approaches (RNomics), is a powerful alternative and probably the most efficient method for identification of such novel gene products [23-26]. The number of functional RNAs has been widely underestimated and is expected to grow rapidly because of the development of new functional RNA cloning methodologies.

The challenge for the future is to define the function and the potential targets of these novel miRNAs by using bioinformatics as well as genetics, and to establish a complete catalogue of time- and tissue-specific distribution of the already identified and yet to be uncovered miRNAs. lin-4 and let-7 stRNAs negatively regulate the expression of proteins encoded by mRNAs whose 3' untranslated regions contain sites of complementarity to the stRNA [3-5].

Thus, a series of 33 novel genes, coding for 19- to 23-nucleotide microRNAs (miRNAs), has been cloned from fly embryos and human cells. Some of these miRNAs are highly conserved between vertebrates and invertebrates and are developmentally or tissue-specifically expressed. Two of the characterized human miRNAs may function as tumor suppressors in B-cell chronic lymphocytic leukemia. miRNAs are related to a small class of previously described 21- and 22-nt RNAs (lin-4 and let-7 RNAs), so-called small temporal RNAs (stRNAs), and regulate developmental timing in C. elegans and other species. Similar to stRNAs, miRNAs are presumed to regulate translation of specific target mRNAs by binding to partially complementary sites, which are present in their 3'-untranslated regions.

Deregulation of miRNA expression may be a cause of human disease, and detection of expression of miRNAs may become useful as a diagnostic. Regulated expression of miRNAs in cells or tissue devoid of particular miRNAs may be useful for tissue engineering, and delivery or transgenic expression of miRNAs may be useful for therapeutic intervention. miRNAs may also represent valuable drug targets itself. Finally, miRNAs and their precursor sequences may be engineered to recognize therapeutic valuable targets.

EXAMPLE 2 miRNAs From Mouse

To gain more detailed insights into the distribution and function of miRNAs in mammals, we investigated the tissue-specific distribution of miRNAs in adult mouse. Cloning of miRNAs from specific tissues was preferred over whole organism-based cloning because low-abundance miRNAs that normally go undetected by Northern blot analysis are identified clonally. Also, in situ hybridization techniques for detecting 21-nt RNAs have not yet been developed. Therefore, 19- to 25-nucleotide RNAs were cloned and sequenced from total RNA, which was isolated from 18.5-weeks old BL6 mice. Cloning of miRNAs was performed as follows: 0.2 to 1 mg, of total RNA was separated on a 15% denaturing polyacrylamide gel and RNA of 19- to 25-nt size was recovered. A 5'-phosphorylated 3'-adapter oligonucleotide (5'-pUUaaccgcgaattccagx: uppercase, RNA; lowercase, DNA; p, phosphate; x, 3'-Amino-Modifier C-7, ChemGenes, Ashland, Mass., USA, Cat. No. NSS-1004; SEQ ID NO:54) and a 5'-adapter oligonucleotide (5'-acggaattcctcactAAA: uppercase, RNA; lowercase, DNA; SEQ ID NO:55) were ligated to the short RNAs. RT/PCR was performed with 3'-primer (5'-GACTAGCTGGAATTCGCGGTTAAA; SEQ ID NO:56) and 5'-primer (5'-CAGCCAACGGAATTCCTCACTAAA; SEQ ID NO:57). In order to introduce Ban I restriction sites, a second PCR was performed using the primer pair 5'-CAGCCAACAGGCACCGAATTCCTCACTAAA (SEQ ID NO: 412) and 5'-GACTAGCTTGGTGCCGAATTCGCGGTTAAA (SEQ ID NO: 413), followed by concatamerization after Ban I digestion and T4 DNA ligation. Concatamers of 400 to 600 basepairs were cut out from 1.5% agarose gels and recovered by Biotrap (Schleicher & Schuell) electroelution (1.times.TAE buffer) and by ethanol precipitation. Subsequently, the 3' ends of the concatamers were filled in by incubating for 15 min at 72.degree. C. with Taq polymerase in standard PCR reaction mixture. This solution was diluted 3-fold with water and directly used for ligation into pCR2.1 TOPO vectors. Clones were screened for inserts by PCR and 30 to 50 samples were subjected to sequencing. Because RNA was prepared from combining tissues of several mice, minor sequence variations that were detected multiple times in multiple clones may reflect polymorphisms rather than RT/PCR mutations. Public database searching was used to identify the genomic sequences encoding the approx. 21-nt RNAs. The occurrence of a 20 to 30 base pair fold-back structure involving the immediate upstream or downstream flanking sequences was used to assign miRNAs [36-38].

We examined 9 different mouse tissues and identified 34 novel miRNAs, some of which are highly tissue-specifically expressed (Table 3 and FIG. 5). Furthermore, we identified 33 new miRNAs from different mouse tissues and also from human Soas-2 osteosarcoma cells (Table 4). miR-1 was previously shown by Northern analysis to be strongly expressed in adult heart, but not in brain, liver, kidney, lung or colon [37]. Here we show that miR-1 accounts for 45% of all mouse miRNAs found in heart, yet miR-1 was still expressed at a low level in liver and midbrain even though it remained undetectable by Northern analysis. Three copies or polymorphic alleles of miR-1 were found in mice. The conservation of tissue-specific miR-1 expression between mouse and human provides additional evidence for a conserved regulatory role of this miRNA. In liver, variants of miR-122 account for 72% of all cloned miRNAs and miR-122 was undetected in all other tissues analyzed. In spleen, miR-143 appeared to be most abundant, at a frequency of approx. 30%. In colon, miR-142-as, was cloned several times and also appeared at a frequency of 30%. In small intestine, too few miRNA sequences were obtained to permit statistical analysis. This was due to strong RNase activity in this tissue, which caused significant breakdown of abundant non-coding RNAs, e.g. rRNA, so that the fraction of miRNA in the cloned sequences was very low. For the same reason, no miRNA sequences were obtained from pancreas.

To gain insights in neural tissue miRNA distribution, we analyzed cortex, cerebellum and midbrain. Similar to heart, liver and small intestine, variants of a particular miRNA, miR-124, dominated and accounted for 25 to 48% of all brain miRNAs. miR-101, -127, -128, -131, and -132, also cloned from brain tissues, were further analyzed by Northern blotting and shown to be predominantly brain-specific. Northern blot analysis was performed as described in Example 1. tRNAs and 5S rRNA were detected by ethidium staining of polyacrylamide gels prior to transfer to verify equal loading. Blots were stripped by boiling in deionized water for 5 min, and reprobed up to 4 times until the 21-nt signals became too weak for detection.

miR-125a and miR-125b are very similar to the sequence of *C. elegans* lin-4 stRNA and may represent its orthologs (FIG. 6A). This is of great interest because, unlike let-7 that was readily detected in other species, lin-4 has acquired a few mutations in the central region and thus escaped bioinformatic database searches. Using the mouse sequence miR-125b, we could readily identify its ortholog in the *D. melanogaster* genome. miR-125a and miR-125b differ only by a central diuridine insertion and a U to C change. miR-125b is very similar to lin-4 stRNA with the differences located only in the central region, which is presumed to be bulged out during target mRNA recognition [41]. miR-125a and miR-125b were cloned from brain tissue, but expression was also detected by Northern analysis in other tissues, consistent with the role for lin-4 in regulating neuronal remodeling by controlling lin-14 expression [43]. Unfortunately, orthologs to *C. elegans* lin-14 have not been described and miR-125 targets remain to be identified in *D. melanogaster* or mammals. Finally, miR-125b expression is also developmentally regulated and only detectable in pupae and adult but not in embryo or larvae of *D. melanogaster* (FIG. 6B).

Sequence comparison of mouse miRNAs with previously described miRNA reveals that miR-99b and miR-99a are similar to *D. melanogaster*, mouse and human miR-10 as well as *C. elegans* miR-51 [36], miR-141 is similar to *D. melanogaster* miR-8 miR-29b is similar to *C. elegans* miR-83, and miR-131 and miR-142-s are similar to *D. melanogaster* miR-4 and *C. elegans* miR-79 [36]. miR-124a is conserved between invertebrates and vertebrates. In this respect it should be noted that for almost every miRNA cloned from mouse was also encoded in the human genome, and frequently detected in other vertebrates, such as the pufferfish, *Fugu rubripes*, and the zebrafish, *Danio rerio*. Sequence conservation may point to conservation in function of these miRNAs. Comprehensive information about orthologous sequences is listed in FIG. 7.

In two cases both strands of miRNA precursors were cloned (Table 3), which was previously observed once for a *C. elegans* miRNA [36]. It is thought that the most frequently cloned strand of a miRNA precursor represents the functional miRNA, which is miR-30c-s and miR-142-as, s and as indicating the 5' or 3'side of the fold-back structure, respectively.

The mir-142 gene is located on chromosome 17, but was also found at the breakpoint junction of a t(8;17) translocation, which causes an aggressive B-cell leukemia due to strong up-regulation of a translocated MYC gene [44]. The translocated MYC gene, which was also truncated at the first exon, was located only 4-nt downstream of the 3'-end of the miR-142 precursor. This suggests that translocated MYC was under the control of the upstream miR-142 promoter. Alignment of mouse and human miR-142 containing EST sequences indicate an approximately 20 nt conserved sequence element downstream of the mir-142 hairpin. This element was lost in the translocation. It is conceivable that the absence of the conserved downstream sequence element in the putative miR-142/mRNA fusion prevented the recognition of the transcript as a miRNA precursor and therefore may have caused accumulation of fusion transcripts and overexpression of MYC.

miR-155, which was cloned from colon, is excised from the known noncoding BIC RNA [47]. BIC was originally identified as a gene transcriptionally activated by promoter insertion at a common retroviral integration site in B cell lymphomas induced by avian leukosis virus. Comparison of BIC cDNAs from human, mouse and chicken revealed 78% identity over 138 nucleotides [47]. The identity region covers the miR-155 fold-back precursor and a few conserved boxes downstream of the fold-back sequence. The relatively high level of expression of BIC in lymphoid organs and cells in human, mouse and chicken implies an evolutionary conserved function, but BIC RNA has also been detected at low levels in non-hematopoietic tissues [47].

Another interesting observation was that segments of perfect complementarity to miRNAs are not observed in mRNA sequences or in genomic sequences outside the miRNA inverted repeat. Although this could be fortuitous, based on the link between RNAi and miRNA processing [11, 13, 43] it may be speculated that miRNAs retain the potential to cleave perfectly complementary target RNAs. Because translational control without target degradation could provide more flexibility it may be preferred over mRNA degradation.

In summary, 63 novel miRNAs were identified from mouse and 4 novel miRNAs were identified from human Soas-2 osteosarcoma cells (Table 3 and Table 4), which are conserved in human and often also in other non-mammalian vertebrates. A few of these miRNAs appear to be extremely tissue-specific, suggesting a critical role for some miRNAs in tissue-specification and cell lineage decisions. We may have also identified the fruitfly and mammalian ortholog of *C. elegans* lin-4 stRNA. The establishment of a comprehensive list of miRNA sequences will be instrumental for bioinformatic approaches that make use of completed genomes and the power of phylogenetic comparison in order to identify miRNA-regulated target mRNAs.

References And Notes

1. R. C. Lee, R. L. Feinbaum, V. Ambros, Cell 75, 843 (1993).
2. B. J. Reinhart et al., Nature 403, 901 (2000).
3. V. Ambros, Curr. Opin. Genet. Dev. 10, 428 (2000).
4. E. G. Moss, Curr. Biol. 10, R436 (2000).
5. F. Slack, G. Ruvkun, Annu. Rev. Genet. 31, 611 (1997).
6. A. E. Pasquinelli et al., Nature 408, 86 (2000).
7. S. M. Elbashir et al., Nature 411, 494 (2001).
8. S. M. Elbashir, W. Lendeckel, T. Tuschl, Genes & Dev. 15, 188 (2001).
9. A. J. Hamilton, D. C. Baulcombe, Science 286, 950 (1999).
10. S. M. Hammond, E. Bernstein, D. Beach, G. J. Hannon, Nature 404, 293 (2000).
11. P. D. Zamore, T. Tuschl, P. A. Sharp, D. P. Bartel, Cell 101, 25 (2000).
12. G. Hutvágner, J. McLachlan, É. Báint, T. Tuschl, P. D. Zamore, Science 93, 834 (2001).
13. A. Grishok et al., Cell 106, 23 (2001).
14. Cloning of 19- to 24-nt RNAs from *D. melanogaster* 0-2 h embryo lysate was performed as described (8). For cloning of HeLa miRNAs, 1 mg of HeLa total RNA was separated on a 15% denaturing polyacrylamide gel and RNA of 19- to 25-nt size was recovered. A 5' phosphorylated 3' adapter oligonucleotide (5' pUUU-aaccgc-gaattccagx: uppercase, RNA; lowercase, DNA; p, phosphate; x, 4-hydroxymethylbenzyl; SEQ ID NO:54) and a 5' adapter oligonucleotide (5' acggaattcctcactAAA: uppercase, RNA; lowercase, DNA; SEQ ID NO:55) were ligated to the short HeLa cell RNAs. RT/PCR was performed with 3 primer (5 'GACTAGCTGGAAT-TCGCGGTTAAA; SEQ ID NO:56) and 5' primer (5' CAGCCAACGGAATTCCTCACTAAA; SEQ ID NO:57), and followed by concatamerization after Eco RI digestion and T4 DNA ligation (8). After ligation of concatamers into pCR2.1 TOPO vectors, about 100 clones were selected and subjected to sequencing.
15. I. Schneider, J Embryol Exp Morphol 27, 353 (1972).
16. R. Feinbaum, V. Ambros, Dev. Biol. 210, 87 (1999).
17. S. M. Hammond, S. Boettcher, A. A. Caudy, R. Kobayashi, G. J. Harmon, Science 293, 1146 (2001).
18. A. A. Aravin et al., Curr. Biol. 11, 1017 (2001).
19. H. Tabara et al., Cell 99, 123 (1999).
20. M. Fagard, S. Boutet, J. B. Morel, C. Bellini, H. Vaucheret, Proc. Natl. Acad. Sci. USA 97, 11650 (2000).
21. C. Catalanotto, G. Azzalin, G. Macino, C. Cogoni, Nature 404, 245 (2000).
22. S. R. Eddy, Curr. Opin. Genet. Dev. 9, 695 (1999).
23. J. Cavaille et al., Proc. Natl. Acad. Sci. USA 97, 14311 (2000).
24. A; Hüttenhofer et al., EMBO J. 20, 2943 (2001).
25. L. Argaman et al., Curr. Biol. 11, 941 (2001).
26. K. M. Wasserman, F. Repoila, C. Rosenow, G. Storz, S. Gottesman, Genes & Dev. 15, 1637 (2001).
27. Supplementary Web material is available on Science Online at www.sciencemag.org/cgi/content/full/xxx
28. D. H. Mathews, J. Sabina, M. Zuker, D. H. Turner, J. Mol. Biol. 288, 911 (1999).
29. E. Bernstein, A. A. Caudy, S. M. Hammond, G. J. Hannon, Nature 409, 363 (2001).
30. Graham, F. L. and van der Eb, A. J., (1973), Virol. 52, 456.
31. McCutchan, J. H. and Pagano, J. S., (1968), J. Natl. Cancer Inst. 41, 351.
32. Chu, G. et al., (1987), Nucl. Acids Res. 15, 1311.
33. Fraley, R. et al., (1980), J. Biol. Chem. 255, 10431.
34. Capecchi, M. R., (1980), Cell 22, 479.
35. Feigner, P. L. et al., (1987), Proc. Natl. Acad. Sci USA 84, 7413.
36. Lau N. C., Lim L. P., Weinstein E. G., Bartel D. P., (2001), Science 294, 858-862.
37. Lee R. C., Ambros V., (2001), Science 294, 862-864.
38. Ambros V., (2001), Cell 107, 823-826.
39. Ambros V., Horvitz H. R., (1984), Science 226, 409-416.
40. Wightman B., Ha I., Ruvkun G., (1993), Cell 75, 855-862.
41. Rougvie A. E., (2001), Nat. Rev. Genet. 2, 690-701.
42. Ketting R. F., Fischer S. E., Bernstein E., Sijen T., Hannon G. J., Plasterk R. N., (2001), Genes & Dev. 15, 2654-2659.
43. Hallam S. J., Jin Y., (1998), Nature 395, 78-82.
44. Gauwerky C. E., Huebner K., Isobe M.; Nowell P. C., Croce C. M., (1989), Proc. Natl. Acad. Sci. USA 86, 8867-8871.
45. P. Chomczynski, N. Sacchi, Anal Biochem 162, 156, (1987).
46. Mourelatos Z., Dostie J., Paushkin S., Sharma A., Charroux B., Abel L., J. R., Mann M., Dreyfuss G., (2002), Genes & Dev., in press.
47. Tam W., (2001), Gene 274, 157-167. *D. melanogaster* miRNAs. The sequences given represent the most abundant and typically longest miRNA sequence identified by cloning; miRNAs frequently vary in length by one or two nucleotides at their 3'termini. From 222 short RNAs sequenced, 69 (31%) correspond to miRNAs, 103 (46%) to already characterized functional RNAs (rRNA, 7SL RNA, tRNAs), 30 (14%) to transportaion RNA fragments, and 20 (10%) sequences with no database entry. The frequency (freq.) for cloning a particular miRNA relative to all identified miRNAs is indicated in percent. Results of Northern blotting of total RNA isolated from staged populations Of *D. melanogaster* are summarized. E, embryo; L; larval stage; P; pupae; A, adult; S2, Schneider-2 cells. The strength of the signal within each blot is represented from the strongest (+++) to undetected (−). let-7 stRNA was probed as control. Genbank accession numbers and homologs of miRNAs identified by database searching in other species are provided as supplementary material.

TABLE 1

D. melanogaster miRNAs.

| miRNA | sequence (5' to 3') | freq. (%) | E 0-3 h | E 0-6 h | L1 + L2 | L3 | P | A | S2 |
|---|---|---|---|---|---|---|---|---|---|
| miR-1 | UGGAAUGUAAAGAAGUAUGGAG (SEQ ID NO: 58) | 32 | + | + | +++ | +++ | ++ | +++ | − |
| miR-2a* | UAUCACAGCCAGCUUUGAUGAGC (SEQ ID NO: 59) | 3 | | | | | | | |
| miR-2b* | UAUCACAGCCAGCUUUGAGGAGC (SEQ ID NO: 60) | 3 | ++ | ++ | ++ | +++ | ++ | + | +++ |
| miR-3 | UCACUGGGCAAAGUGUGUCUCA# | 9 | +++ | +++ | − | − | − | − | − |
| miR-4 | AUAAAGCUAGACAACCAUUGA (SEQ ID NO: 62) | 6 | +++ | +++ | − | − | − | − | − |
| miR-5 | AAAGGAACGAUCGUUGUGAUAUG (SEQ ID NO: 63) | 1 | +++ | +++ | +/− | +/− | − | − | − |
| miR-6 | UAUCACAGUGGCUGUUCUUUUU (SEQ ID NO: 64) | 13 | +++ | +++ | +/− | +/− | − | − | − |
| miR-7 | UGGAAGACUAGUGAUUUUGUUGU (SEQ ID NO: 65) | 4 | +++ | ++ | +/− | +/− | +/− | +/− | +/− |
| miR-8 | UAAUACUGUCAGGUAAAGAUGUC (SEQ ID NO: 66) | 3 | +/− | +/− | +++ | +++ | + | +++ | − |
| miR-9 | UCUUUGGUUAUCUAGCUGUAUGA (SEQ ID NO: 67) | 7 | +++ | ++ | +++ | +++ | +++ | +/− | − |
| miR-10 | ACCCUGUAGAUCCGAAUUUGU (SEQ ID NO: 68) | 1 | + | + | ++ | +++ | +/− | + | − |
| miR-11 | CAUCACAGUCUGAGUUCUUGC (SEQ ID NO: 69) | 7 | +++ | +++ | +++ | +++ | +++ | + | − |
| miR-12 | UGAGUAUUACAUCAGGUACUGGU (SEQ ID NO: 70) | 7 | + | + | ++ | ++ | + | +++ | +/− |
| miR-13a* | UAUCACAGCCAUUUUGACGAGU (SEQ ID NO: 71) | 1 | +++ | +++ | +++ | +++ | + | +++ | +++ |
| miR-13b* | UAUCACAGCCAUUUUGAUGAGU (SEQ ID NO: 72) | 0 | | | | | | | |
| miR-14 | UCAGUCUUUUUCUCUCUCCUA (SEQ ID NO: 73) | 1 | − | − | − | − | − | − | − |
| let-7 | UGAGGUAGUAGGUUGUAUAGUU (SEQ ID NO: 74) | 0 | − | − | − | − | +++ | +++ | − |

# = (SEQ ID NO: 61)
*Similar miRNA sequences are difficult to distinguish by Northern blotting because of potential cross-hybridization of probes.
The sequences given represent the most abundant, and typically longest miRNA sequence identified by cloning; miRNAs frequently vary in length by one or two nucleotides at their 3' termini.
From 222 short RNAs sequenced, 69 (31%) corresponded to miRNAs, 103 (46%) to already characterized functional RNAs (rRNA, 7SL RNA, tRNAs), 30 (14%) to transposon RNA fragments, and 20 (10%) sequences with no database entry.
The frequency (freq.) for cloning a particular miRNA relative to all identified miRNAs is indicated in percent.
Results of Northern blotting of total RNA isolated from staged populations of D. melanogaster are summarized.
E, embryo;
L; larval stage;
P; pupae;
A, adult;
S2, Schneider-2 cells.
The strength of the signal within each blot is represented from strongest (+++) to undetected (−). let-7 stRNA was probed as control.
Genbank accession numbers and homologs of miRNAs identified by database searching in other species are provided as supplementary material.

Human miRNAs, From 220 short RNAs sequenced, 100 (45%) corresponded to miRNAs, 53 (24%) to already characterized functional RNAs (rRNA, snRNAs, tRNAs), and 67 (30%) sequences with no database entry. Results of Northern blotting of total RNA isolated from different vertebrate species and S2 cells are indicated. For legend, see Table 1.

TABLE 2

Human miRNAs.

| miRNA | sequence (5' to 3') | freq. (%) | HeLa cells | mouse kidney | adult fish | frog ovary | S2 |
|---|---|---|---|---|---|---|---|
| let-7a* | UGAGGUAGUAGGUUGUAUAGUU# | 10 | +++ | +++ | +++ | − | − |
| let-7b* | UGAGGUAGUAGGUUGUGUGGUU (SEQ ID NO: 76) | 13 | | | | | |
| let-7c* | UGAGGUAGUAGGUUGUAUGGUU (SEQ ID NO: 77) | 3 | | | | | |
| let-7d* | AGAGGUAGUAGGUUGCAUAGU (SEQ ID NO: 78) | 2 | +++ | +++ | +++ | − | − |
| let-7e* | UGAGGUAGGAGGUUGUAUAGU (SEQ ID NO: 79) | 2 | +++ | +++ | +++ | − | − |
| let-7f* | UGAGGUAGUAGAUUGUAUAGUU (SEQ ID NO: 80) | 1 | | | | | |
| miR-15 | UAGCAGCACAUAAUGGUUUGUG (SEQ ID NO: 81) | 3 | +++ | ++ | + | +/− | − |
| miR-16 | UAGCAGCACGUAAAUAUUGGCG (SEQ ID NO: 82) | 10 | +++ | + | +/− | +/− | − |
| miR-17 | ACUGCAGUGAAGGCACUUGU (SEQ ID NO: 83) | 1 | +++ | − | − | − | − |
| miR-18 | UAAGGUGCAUCUAGUGCAGAUA (SEQ ID NO: 84) | 2 | +++ | − | − | − | − |
| miR-19a* | UGUGCAAAUCUAUGCAAAACUGA (SEQ ID NO: 85) | 1 | +++ | − | +/− | − | − |
| miR-19b* | UGUGCAAAUCCAUGCAAAACUGA (SEQ ID NO: 86) | 3 | | | | | |
| miR-20 | UAAAGUGCUUAUAGUGCAGGUA (SEQ ID NO: 87) | 4 | +++ | − | + | − | − |
| miR-21 | UAGCUUAUCAGACUGAUGUUGA (SEQ ID NO: 88) | 10 | +++ | + | ++ | − | − |
| miR-22 | AAGCUGCCAGUUGAAGAACUGU (SEQ ID NO: 89) | 10 | +++ | +++ | + | +/− | − |
| miR-23 | AUCACAUUGCCAGGGAUUUCC (SEQ ID NO: 90) | 2 | +++ | +++ | +++ | + | − |
| miR-24 | UGGCUCAGUUCAGCAGGAACAG (SEQ ID NO: 91) | 4 | ++ | +++ | ++ | − | − |
| miR-25 | CAUUGCACUUGUCUCGGUCUGA (SEQ ID NO: 92) | 3 | +++ | + | ++ | − | − |
| miR-26a* | UUCAAGUAAUCCAGGAUAGGCU (SEQ ID NO: 93) | 2 | + | ++ | +++ | − | − |
| miR-26b* | UUCAAGUAAUUCAGGAUAGGUU (SEQ ID NO: 94) | 1 | | | | | − |
| miR-27 | UUCACAGUGGCUAAGUUCCGCU (SEQ ID NO: 95) | 2 | +++ | +++ | ++ | − | − |
| miR-28 | AAGGAGCUCACAGUCUAUUGAG (SEQ ID NO: 96) | 2 | +++ | +++ | − | − | − |
| miR-29 | CUAGCACCAUCUGAAAUCGGUU (SEQ ID NO: 97) | 2 | + | +++ | +/− | − | − |
| miR-30 | CUUUCAGUCGGAUGUUUGCAGC (SEQ ID NO: 98) | 2 | +++ | +++ | +++ | − | − |

TABLE 2-continued

Human miRNAs.

| miRNA | sequence (5' to 3') | freq. (%) | HeLa cells | mouse kidney | adult fish | frog ovary | S2 |
|---|---|---|---|---|---|---|---|
| miR-31 | GGCAAGAUGCUGGCAUAGCUG (SEQ ID NO: 99) | 2 | +++ | – | – | – | – |
| miR-32 | UAUUGCACAUUACUAAGUUGC (SEQ ID NO: 100) | 1 | – | – | – | – | – |
| miR-33 | GUGCAUUGUAGUUGCAUUG (SEQ ID NO: 101) | 1 | – | – | – | – | – |
| miR-1 | UGGAAUGUAAAGAAGUAUGGAG (SEQ ID NO: 102) | 0 | – | – | + | – | – |
| miR-7 | UGGAAGACUAGUGAUUUUGUUGU (SEQ ID NO: 103) | 0 | + | – | +/– | – | +/– |
| miR-9 | UCUUUGGUUAUCUAGCUGUAUGA (SEQ ID NO: 104) | 0 | – | – | – | – | – |
| miR-10 | ACCCUGUAGAUCCGAAUUUGU (SEQ ID NO: 105) | 0 | – | + | – | – | – |

= (SEQ ID NO: 75)
*Similar miRNA sequences are difficult to distinguish by Northern blotting because of potential cross-hybridization of probes.
From 220 short RNAs sequenced, 100 (45%) corresponded to miRNAs, 53 (24%) to already characterized functional RNAs (rRNA, snRNAs, tRNAs), and 67 (30%) sequences with no database entry.
Results of Northern blotting of total RNA isolated from different vertebrate species and S2 cells are indicated.
For legend, see Table 1.

Mouse miRNAs. The sequences indicated represent the longest miRNA sequences identified by cloning. The 3'-terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variation's between related miRNAs are generally found near the ends of the miRNA sequence and are thought to not compromise target RNA recognition. Minor sequence variations may also represent A to G and C to U changes, which are accommodated as G-U wobble base pairs during target recognition. miRNAs with the suffix -s or -as indicate RNAs derived from either the 5'-half or the 3'-half of a miRNA precursor. Mouse brains were dissected into midbrain, mb, cortex, cx, cerebellum, cb. The tissues analyzed were heart, ht; liver, lv; small intestine, si; colon, co; cortex, ct; cerebellum, cb; midbrain, mb.

TABLE 3

Mouse miRNAs.

| miRNA | sequence (5' to 3') | Number of clones | | | | | | | |
|---|---|---|---|---|---|---|---|---|---|
| | | ht | lv | sp | si | co | cx | cb | mb |
| let-7a | UGAGGUAGUAGGUUGUAUAGUU (SEQ ID NO: 106) | 3 | | | 1 | 1 | | | 7 |
| let-7b | UGAGGUAGUAGGUUGUGUGGUU (SEQ ID NO: 107) | 1 | 1 | | | | | 2 | 5 |
| let-7c | UGAGGUAGUAGGUUGUAUGGUU (SEQ ID NO: 108) | 2 | | | | | 2 | 5 | 19 |
| let-7d | AGAGGUAGUAGGUUGCAUAGU (SEQ ID NO: 109) | 2 | | | 2 | 2 | | | 2 |
| let-7e | UGAGGUAGGAGGUUGUAUAGU (SEQ ID NO: 110) | | 1 | | | | | | 2 |
| let-7f | UGAGGUAGUAGAUUGUAUAGUU (SEQ ID NO: 111) | | 2 | | | | | 3 | 3 |
| let-7g | UGAGGUAGUAGUUUGUACAGUA (SEQ ID NO: 112) | | | | | | | 1 | 1 | 2 |
| let-7h | UGAGGUAGUAGUGUGUACAGUU (SEQ ID NO: 113) | | | | | | | 1 | 1 |

TABLE 3-continued

Mouse miRNAs.

| miRNA | sequence (5' to 3') | ht | lv | sp | si | co | cx | cb | mb |
|---|---|---|---|---|---|---|---|---|---|
| let-7i | UGAGGUAGUAGUUUGUGCU (SEQ ID NO: 114) | | | | | | | 1 | 1 |
| miR-1b | UGGAAUGUAAAGAAGUAUGUAA (SEQ ID NO: 115) | 4 | 2 | | | | | | 1 |
| miR-1c | UGGAAUGUAAAGAAGUAUGUAC (SEQ ID NO: 116) | 7 | | | | | | | |
| miR-1d | UGGAAUGUAAAGAAGUAUGUAUU (SEQ ID NO: 117) | 16 | | | | | | | 1 |
| miR-9 | UCUUUGGUUAUCUAGCUGUAUGA (SEQ ID NO: 118) | | | | | | 3 | 4 | 4 |
| miR-15a | UAGCAGCACAUAAUGGUUUGUG (SEQ ID NO: 119) | 1 | | | | | | | 2 |
| miR-15b | UAGCAGCACAUCAUGGUUUACA (SEQ ID NO: 120) | 1 | | | | | | | |
| miR-16 | UAGCAGCACGUAAAUAUUGGCG (SEQ ID NO: 121) | 1 | | | 1 | 2 | 1 | 2 | 3 |
| miR-18 | UAAGGUGCAUCUAGUGCAGAUA (SEQ ID NO: 122) | | | 1 | | | | | |
| miR-19b | UGUGCAAAUCCAUGCAAAACUGA (SEQ ID NO: 123) | | | 1 | | | | | |
| miR-20 | UAAAGUGCUUAUAGUGCAGGUAG (SEQ ID NO: 124) | | | | | 1 | | | |
| miR-21 | UAGCUUAUCAGACUGAUGUUGA (SEQ ID NO: 125) | 1 | | 1 | 2 | 1 | | | |
| miR-22 | AAGCUGCCAGUUGAAGAACUGU (SEQ ID NO: 126) | 2 | 1 | | 1 | | | 1 | 2 |
| miR-23a | AUCACAUUGCCAGGGAUUUCC (SEQ ID NO: 127) | 1 | | | | | | | |
| miR-23b | AUCACAUUGCCAGGGAUUACCAC (SEQ ID NO: 128) | | | | | | 1 | | |
| miR-24 | UGGCUCAGUUCAGCAGGAACAG (SEQ ID NO: 129) | 1 | | | 1 | 1 | | | 1 |
| miR-26a | UUCAAGUAAUCCAGGAUAGGCU (SEQ ID NO: 130) | | | | | | | 3 | 2 |
| miR-26b | UUCAAGUAAUUCAGGAUAGGUU (SEQ ID NO: 131) | | 2 | | | | 4 | 1 | |
| miR-27a | UUCACAGUGGCUAAGUUCCGCU (SEQ ID NO: 132) | 1 | | 2 | | 1 | 1 | 2 | 1 |
| miR-27b | UUCACAGUGGCUAAGUUCUG (SEQ ID NO: 133) | | | | | | | | 1 |
| miR-29a | CUAGCACCAUCUGAAAUCGGUU (SEQ ID NO: 134) | 1 | | | | 1 | 1 | | |
| miR-29b/miR-102 | UAGCACCAUUUGAAAUCAGUGUU (SEQ ID NO: 135) | 1 | | | 1 | 5 | | 3 | |
| miR-29c/ | UAGCACCAUUUGAAAUCGGUUA (SEQ ID NO: 136) | 1 | | | | 3 | | 1 | |
| miR-30a-s/miR-97 | UGUAAACAUCCUCGACUGGAAGC (SEQ ID NO: 137) | | 1 | | | 1 | | 1 | |

TABLE 3-continued

Mouse miRNAs.

| miRNA | sequence (5' to 3') | ht | lv | sp | si | co | cx | cb | mb |
|---|---|---|---|---|---|---|---|---|---|
| miR-30a-as[a] | CUUUCAGUCGGAUGUUUGCAGC (SEQ ID NO: 138) | | | | | | | 1 | |
| miR-30b | UGUAAACAUCCUACACUCAGC (SEQ ID NO: 139) | | | 1 | | | | 2 | |
| miR-30c | UGUAAACAUCCUACACUCUCAGC (SEQ ID NO: 140) | 2 | | | | | 1 | 1 | |
| miR-30d | UGUAAACAUCCCCGACUGGAAG (SEQ ID NO: 141) | | 1 | | | | | | |
| miR-99a/miR-99 | ACCCGUAGAUCCGAUCUUGU (SEQ ID NO: 142) | | | | | | | 1 | |
| miR-99b | CACCCGUAGAACCGACCUUGCG (SEQ ID NO: 143) | | | | | | | 1 | |
| miR-101 | UACAGUACUGUGAUAACUGA (SEQ ID NO: 144) | | | | | | 2 | 1 | 1 |
| miR-122a | UGGAGUGUGACAAUGGUGUUUGU (SEQ ID NO: 145) | | 3 | | | | | | |
| miR-122b | UGGAGUGUGACAAUGGUGUUUGA (SEQ ID NO: 146) | | 11 | | | | | | |
| miR-122a,b | UGGAGUGUGACAAUGGUGUUUG (SEQ ID NO: 147) | | 23 | | | | | | |
| miR-123 | CAUUAUUACUUUUGGUACGCG (SEQ ID NO: 148) | 1 | 2 | | | | | | |
| miR-124a[b] | UUAAGGCACGCGG-UGAAUGCCA (SEQ ID NO: 149) | | | | | 1 | 37 | 41 | 24 |
| miR-124b | UUAAGGCACGCGGGUGAAUGC (SEQ ID NO: 150) | | | | | | 1 | 3 | |
| miR-125a | UCCCUGAGACCCUUUAACCUGUG (SEQ ID NO: 151) | | | | | | 1 | 1 | |
| miR-125b | UCCCUGAGACCCU--AACUUGUGA (SEQ ID NO: 152) | | | | | | | 1 | |
| miR-126 | UCGUACCGUGAGUAAUAAUGC (SEQ ID NO: 153) | 4 | | | | | | 1 | |
| miR-127 | UCGGAUCCGUCUGAGCUUGGCU (SEQ ID NO: 154) | | | | | | | 1 | |
| miR-128 | UCACAGUGAACCGGUCUCUUUU (SEQ ID NO: 155) | | | | | | 2 | 2 | 2 |
| miR-129 | CUUUUUUCGGUCUGGGCUUGC (SEQ ID NO: 156) | | | | | | | 1 | |
| miR-130 | CAGUGCAAUGUUAAAAGGGC (SEQ ID NO: 157) | | | | | | | 1 | |
| miR-131 | UAAAGCUAGAUAACCGAAAGU (SEQ ID NO: 158) | | | | | | 1 | 1 | 1 |
| miR-132 | UAACAGUCUACAGCCAUGGUCGU (SEQ ID NO: 159) | | | | | | | 1 | |
| miR-133 | UUGGUCCCCUUCAACCAGCUGU (SEQ ID NO: 160) | 4 | | | | | 1 | | |
| miR-134 | UGUGACUGGUUGACCAGAGGGA (SEQ ID NO: 161) | | | | | | | 1 | |

TABLE 3-continued

Mouse miRNAs.

| miRNA | sequence (5' to 3') | ht | lv | sp | si | co | cx | cb | mb |
|---|---|---|---|---|---|---|---|---|---|
| miR-135 | UAUGGCUUUUUAUUCCUAUGUGAA (SEQ ID NO: 162) | | | | | | 1 | | |
| miR-136 | ACUCCAUUUGUUUUGAUGAUGGA (SEQ ID NO: 163) | | | | | | 1 | | |
| miR-137 | UAUUGCUUAAGAAUACGCGUAG (SEQ ID NO: 164) | | | | | | 1 | 1 | |
| miR-138 | AGCUGGUGUUGUGAAUC (SEQ ID NO: 165) | | | | | | 1 | | |
| miR-139 | UCUACAGUGCACGUGUCU (SEQ ID NO: 166) | | | | | 1 | 1 | | |
| miR-140 | AGUGGUUUUACCCUAUGGUAG (SEQ ID NO: 167) | | | | 1 | | | | |
| miR-141 | AACACUGUCUGGUAAAGAUGG (SEQ ID NO: 168) | | | 1 | 1 | | 1 | | |
| miR-142-s | CAUAAAGUAGAAAGCACUAC (SEQ ID NO: 169) | | | | 1 | 1 | | | |
| miR-142-as[b] | UGUAGUGUUUCCUACUUUAUGG (SEQ ID NO: 170) | | | 1 | 1 | 6 | | | |
| miR-143 | UGAGAUGAAGCACUGUAGCUCA (SEQ ID NO: 171) | 3 | | 7 | | | 2 | | 1 |
| miR-144 | UACAGUAUAGAUGAUGUACUAG (SEQ ID NO: 172) | 2 | | | | 1 | | | |
| miR-145 | GUCCAGUUUUCCCAGGAAUCCCUU (SEQ ID NO: 173) | 1 | | | | | | | |
| miR-146 | UGAGAACUGAAUUCCAUGGGUUU (SEQ ID NO: 174) | 1 | | | | | | | |
| miR-147 | GUGUGUGGAAAUGCUUCUGCC (SEQ ID NO: 175) | | | | 1 | | | | |
| miR-148 | UCAGUGCACUACAGAACUUUGU (SEQ ID NO: 176) | | | | 1 | | | | |
| miR-149 | UCUGGCUCCGUGUCUUCACUCC (SEQ ID NO: 177) | 1 | | | | | | | |
| miR-150 | UCUCCCAACCCUUGUACCAGUGU (SEQ ID NO: 178) | | | | | | 1 | | |
| miR-151 | CUAGACUGAGGCUCCUUGAGGU (SEQ ID NO: 179) | | | | | | 1 | | |
| miR-152 | UCAGUGCAUGACAGAACUUGG (SEQ ID NO: 180) | | | | | | 1 | | |
| miR-153 | UUGCAUAGUCACAAAAGUGA (SEQ ID NO: 181) | | | | | | | | 1 |
| miR-154 | UAGGUUAUCCGUGUUGCCUUCG (SEQ ID NO: 182) | | | | | | | | 1 |
| miR-155 | UUAAUGCUAAUUGUGAUAGGGG (SEQ ID NO: 183) | | | | 1 | | | | |

[a]The originally described miR-30 was renamed to miR-30a-as in order to distinguish it from the miRNA derived from the opposite strand of the precursor encoded by the mir-30a gene. miR-30a-s is equivalent to miR-97 [46].
[b]A 1-nt length heterogeneity is found on both 5' and 3' end. The 22-nt miR sequence is shown, but only 21-nt miRNAs were cloned.
The sequences indicated represent the longest miRNA sequences identified by cloning.

TABLE 3-continued

Mouse miRNAs.

| | | Number of clones |
|---|---|---|
| miRNA | sequence (5' to 3') | ht lv sp si co cx cb mb |

The 3'-terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter.
Minor sequence variations between related miRNAs are generally found near the ends of the miRNA sequence and are thought to not compromise target RNA recognition.
Minor sequence variations may also represent A to G and C to U changes, which are accommodated as G-U wobble base pairs during target recognition.
miRNAs with the suffix-s or -as indicate RNAs derived from either the 5'-half or the 3'-half of a miRNA precursor.
Mouse brains were dissected into midbrain, mb, cortex, cx, cerebellum, cb.
The tissues analyzed were heart, ht; liver, lv; small intestine, si; colon, co; cortex, ct; cerebellum, cb; midbrain, mb.

Mouse and human miRNAs. The sequences indicated represent the longest miRNA sequences identified by cloning. The 3' terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target. RNA recognition. Minor sequence variations may also represent A to G and C to U changes; which are accommodated as G-U wobble base pairs during target recognition. Mouse brains were dissected into midbrain, mb, cortex, cx, cerebellum, cb. The tissues analyzed were lung, ln; liver, lv; spleen, sp; kidney, kd; skin, sk; testis, ts; ovary, ov; thymus, thy; eye, ey; cortex, ct; cerebellum, cb; midbrain, mb. The human osteosarcoma cells SAOS-2 cells contained an inducible p53 gene (p53-, uninduced p53; p53+, induced p53); the differences in miRNAs identified from induced and uninduced SAOS cells were not statistically significant.

TABLE 4

Mouse and human miRNAs.

| | | number of clones | | |
|---|---|---|---|---|
| | | mouse tissues | | human SAOS-2 cells |
| miRNA | Sequence (5' to 3') | ln lv sp kd sk ts ov thy ey | p53- p53+ | |
| miR-C1 | AACAUUCAACGCUGUCGGUGAGU | 1        1        2 | | (SEQ ID NO. 184) |
| miR-C2 | UUUGGCAAUGGUAGAACUCACA |                    1 | | (SEQ ID NO. 185) |
| miR-C3 | UAUGGCACUGGUAGAAUUCACUG |                    1 | | (SEQ ID NO. 186) |
| miR-C4 | CUUUUUGCGGUCUGGGCUUGUU |              1     1 | 1 | (SEQ ID NO. 187) |
| miR-C5 | UGGACGGAGAACUGAUAAGGGU |                    2 | | (SEQ ID NO. 188) |
| miR-C6 | UGGAGAGAAAGGCAGUUC |                    1 | | (SEQ ID NO. 189) |
| miR-C7 | CAAAGAAUUCUCCUUUUGGGCUU |                    1 | 1 | (SEQ ID NO. 190) |
| miR-C8 | UCGUGUCUUGUGUUGCAGCCGG |        1 | | (SEQ ID NO. 191) |
| miR-C9 | UAACACUGUCUGGUAACGAUG |        1 | | (SEQ ID NO. 192) |
| miR-C10 | CAUCCCUUGCAUGGUGGAGGGU |        1 | | (SEQ ID NO. 193) |
| miR-C11 | GUGCCUACUGAGCUGACAUCAGU |        1 | | (SEQ ID NO. 194) |
| miR-C12 | UGAUAUGUUUGAUAUAUUAGGU |        2 | | (SEQ ID NO. 195) |
| miR-C13 | CAACGGAAUCCCAAAAGCAGCU |     2  1 | | (SEQ ID NO. 196) |
| miR-C14 | CUGACCUAUGAAUUGACA |     2  1 | | (SEQ ID NO. 197) |
| miR-C15 | UACCACAGGGUAGAACCACGGA |        1 | | (SEQ ID NO. 198) |
| miR-C16 | AACUGGCCUACAAAGUCCCAG |        1 | | (SEQ ID NO. 199) |
| miR-C17 | UGUAACAGCAACUCCAUGUGGA |        1 | | (SEQ ID NO. 200) |
| miR-C18 | UAGCAGCACAGAAAUAUUGGC |     2     1  1 | | (SEQ ID NO. 201) |

TABLE 4-continued

Mouse and human miRNAs.

| | | number of clones | | | | | | | | | | |
|---|---|---|---|---|---|---|---|---|---|---|---|---|
| | | mouse tissues | | | | | | | | | human SAOS-2 cells | | |
| miRNA | Sequence (5' to 3') | ln | lv | sp | kd | sk | ts | ov | thy | ey | p53- | p53+ | |
| miR-C19 | UAGGUAGUUUCAUGUUGUUGG | | | | | | | | | | 1 | | (SEQ ID NO. 202) |
| miR-C20 | UUCACCACCUUCUCCACCCAGC | | | | | | | | | | 1 | 1 | (SEQ ID NO. 203) |
| miR-C21 | GGUCCAGAGGGGAGAUAGG | | | | | | | | | | 1 | | (SEQ ID NO. 204) |
| miR-C22 | CCCAGUGUUCAGACUACCUGUU | | | | | | | | | | 1 | | (SEQ ID NO. 205) |
| miR-C23 | UAAUACUGCCUGGUAAUGAUGAC | 2 | | | 1 | | | | | | | | (SEQ ID NO. 206) |
| miR-C24 | UACUCAGUAAGGCAUUGUUCU | | | | 1 | | | | | | | | (SEQ ID NO. 207) |
| miR-C25 | AGAGGUAUAGCGCAUGGGAAGA | | | | 1 | | | | | | | | (SEQ ID NO. 208) |
| miR-C26 | UGAAAUGUUUAGGACCACUAG | | | | 1 | | | | | | | | (SEQ ID NO. 209) |
| miR-C27 | UUCCCUUUGUCAUCCUAUGCCUG | | | | | | | 1 | | | | | (SEQ ID NO. 210) |
| miR-C28 | UCCUUCAUUCCACCGGAGUCUG | | | 1 | | | | | | | | | (SEQ ID NO. 211) |
| miR-C29 | GUGAAAUGUUUAGGACCACUAGA | | | 2 | | | | | | | | | (SEQ ID NO. 212) |
| miR-C30 | UGGAAUGUAAGGAAGUGUGUGG | | | 2 | | | | | | | | | (SEQ ID NO. 213) |
| miR-C31 | UACAGUAGUCUGCACAUUGGUU | | | 1 | | | | | | | | | (SEQ ID NO. 214) |
| miR-C32 | CCCUGUAGAACCGAAUUUGUGU | | | 1 | 1 | | | | | | | | (SEQ ID NO. 215) |
| miR-C33 | AACCCGUAGAUCCGAACUUGUGAA | | | 1 | | | | | | | | | (SEQ ID NO. 216) |
| miR-C34 | GCUUCUCCUGGCUCUCCUCCCUC | | | | | | | 1 | | | | | (SEQ ID NO. 217) |

The sequences indicated represent the longest miRNA sequences identified by cloning.
The 3' terminus of miRNAs is often truncated by one or two nucleotides.
miRNAs that are more than 85% identical in sequence (i.e. share 18 out of 21 nucleotides) or contain 1- or 2-nucleotide internal deletions are referred to by the same gene number followed by a lowercase letter.
Minor sequence variations between related miRNAs are generally found near the ends of the miRNA sequence and are thought to not compromise target RNA recognition.
Minor sequence variations may also represent A to G and C to U changes; which are accommodated as G-U wobble base pairs during target recognition,
Mouse brains were dissected into midbrain, mb, cortex, cx, cerebellum, cb.
The tissues analyzed were lung, ln; liver, lv; spleen, sp; kidney, kd; skin, sk; testis, ts; ovary, ov; thymus, thy; eye, ey; cortex, ct; cerebellum, cb; midbrain, mb.
The human osteosarcoma cells SAOS-2 cells contained an inducible p53 gene (p53-, uninduced p53; p53+, induced p53); the differences in miRNAs identified from induced and uninduced SAOS cells were not statistically significant.

*D. melanogaster* miRNA sequences and genomic location. The sequences given represent the most abundant, and typically longest miRNA sequences identified by cloning. It was frequently observed that miRNAs vary in length by one or two nucleotides at their 3'-terminus. From 222 Short RNAs sequenced; 69 (31%) corresponded to miRNAs), 103 (46%) to already characterized functional RNAs (rRNA, 7SL RNA, tRNAs), 30 (14%) to transportation RNA fragments, and 20 (10%) sequences with no database entry. RNA sequences with a 5'-guanosine are likely to be underrepresented due to the cloning procedure (8). miRNA homologs found in other species are indicated. Chromosomal location (chr.) and GenBank accesion numbers (acc. nb.) are indicated. No ESTs matching miR-1 to miR-14 were detectable by database searching.

TABLE 5

*D. melanogaster* miRNA sequences and genomic location.

| miRNA | sequence (5' to 3') | chr., acc. nb. | remarks |
|---|---|---|---|
| miR-1 | UGGAAUGUAAAGAAGUAUGGAG (SEQ ID ID: 58) | 2L, AE003667 | homologs: *C. briggsae*, G20U, AC87074; *C. elegans* G20U, U97405; mouse, G20U, G22U, AC020867; human, chr. 20, G20U, G22U, AL449263; ESTs: zebrafish, G20U, G22U, BF157- |

TABLE 5-continued

*D. melanogaster* miRNA sequences and genomic location.

| miRNA | sequence (5' to 3') | chr., acc. nb. | remarks |
|---|---|---|---|
| | | | 601; cow, G20U, G22U, BE722-224; human, G20U, G22U, AI220268 |
| miR-2a | UAUCACAGCCAGCUUUGAUGAGC (SEQ ID NO: 59) | 2L, AE003663 | 2 precursor variants clustered with a copy of mir-2b |
| miR-2b | UAUCACAGCCAGCUUUGAGGAGC (SEQ ID NO: 60) | 2L, AE003620 2L, AE003663 | 2 precursor variants |
| miR-3 | UCACUGGGCAAAGUGUGUCUCA (SEQ ID NO: 61) | 2R, AE003795 | in cluster mir-3 to mir-6 |
| miR-4 | AUAAAGCUAGACAACCAUUGA (SEQ ID NO: 62) | 2R, AE003795 | in cluster mir-3 to mir-6 |
| miR-5 | AAAGGAACGAUCGUUGUGAUAUG (SEQ ID NO: 63) | 2R, AE003795 | in cluster mir-3 to mir-6 |
| miR-6 | UAUCACAGUGGCUGUUCUUUUU (SEQ ID NO: 64) | 2R, AE003795 | in cluster mir-3 to mir-6 with 3 variants |
| miR-7 | UGGAAGACUAGUGAUUUUGUUGU (SEQ ID NO: 65) | 2R, AE003791 | homologs: human, chr. 19 AC006537, EST BF373391; mouse chr. 17 AC026385, EST AA881786 |
| miR-8 | UAAUACUGUCAGGUAAAGAUGUC (SEQ ID NO: 66) | 2R, AE003805 | |
| miR-9 | UCUUUGGUUAUCUAGCUGUAUGA (SEQ ID NO: 67) | 3L, AE003516 | homologs: mouse, chr. 19, AF155142; human, chr. 5, AC026701, chr. 15, AC005316 |
| miR-10 | ACCCUGUAGAUCCGAAUUUGU (SEQ ID NO: 68) | AE001574 | homologs: mouse, chr 11, AC011194; human, chr. 17, AF287967 |
| miR-11 | CAUCACAGUCUGAGUUCUUGC (SEQ ID NO: 69) | 3R, AE003735 | intronic location |
| miR-12 | UGAGUAUUACAUCAGGUACUGGU (SEQ ID NO: 70) | X, AE003499 | intronic location |
| miR-13a | UAUCACAGCCAUUUUGACGAGU (SEQ ID NO: 71) | 3R, AE003708 X, AE003446 | mir-13a clustered with mir-13b on chr. 3R |
| miR-13b | UAUCACAGCCAUUUUGAUGAGU (SEQ ID NO: 72) | 3R, AE003708 | mir-13a clustered with mir-13b on chr. 3R |
| miR-14 | UCAGUCUUUUCUCUCUCCUA (SEQ ID NO: 73) | 2R, AE003833 | no signal by Northern analysis |

The sequences given represent the most abundant, and typically longest miRNA sequences identified by cloning.
It was frequently observed that miRNAs vary in length by one or two nucleotides at their 3'-terminus.
From 222 short RNAs sequenced; 69 (31%) corresponded to miRNAs, 103 (46%) to already characterized functional RNAs (rRNA, 7SL RNA, tRNAs), 30 (14%) to transposon RNA fragments, and 20 (10%) sequences with no database entry.
RNA sequences with a 5'-guanosine are likely to be underrepresented due to the cloning procedure (8).
miRNA homologs found in other species are indicated.
Chromosomal location (chr.) and GenBank accession numbers (acc. nb.) are indicated.
No ESTs matching miR-1 to miR-14 were detectable by database searching.

Human miRNA sequences and genomic location. From 220 short RNAs sequenced, 100 (45%) correspond to miRNAs, 53 (24%) to already characterized functional RNAs (rRNA, snRNAs, tRNAs), and 67 (30%) sequences with no database entry. For legend, see Table 1.

TABLE 6

Human miRNA sequences and genomic location.

| miRNA | sequence (5' to 3') | chr. or EST, acc. nb. | remarks* |
|---|---|---|---|
| let-7a | UGAGGUAGUAGGUUGUAUAGUU (SEQ ID NO: 75) | 9, AC007924, 11, AP001359, 17, AC087784, 22, AL049853 | sequences of chr 9 and 17 identical and clustered with let-7f, homologs: *C. elegans*, AF274345; *C. briggsae*, AF210771, *D. melanogaster*, AE003659 |
| let-7b | UGAGGUAGUAGGUUGUGUGGUU (SEQ ID NO: 76) | 22, AL049853†, ESTs, AI382133, AW028822 | homologs: mouse, EST AI481799; rat, EST, BE120662 |
| let-7c | UGAGGUAGUAGGUUGUAUGGUU (SEQ ID NO: 77) | 21, AP001667 | Homologs: mouse, EST, AA575575 |
| let-7d | AGAGGUAGUAGGUUGCAUAGU (SEQ ID NO: 78) | 17, AC087784, 9, AC007924 | identical precursor sequences |
| let-7e | UGAGGUAGGAGGUUGUAUAGU (SEQ ID NO: 79) | 19, AC018755 | |
| let-7f | UGAGGUAGUAGAUUGUAUAGUU (SEQ ID NO: 80) | 9, AC007924, 17, AC087784, X, AL592046 | sequences of chr 9 and 17 identical and clustered with let-7a |
| miR-15 | UAGCAGCACAUAAUGGUUUGUG (SEQ ID NO: 81) | 13, AC069475 | in cluster with mir-16 homolog |
| miR-16 | UAGCAGCACGUAAAUAUUGGCG (SEQ ID NO: 82) | 13, AC069475 | in cluster with mir-15 homolog |
| miR-17 | ACUGCAGUGAAGGCACUUGU (SEQ ID NO: 83) | 13, AL138714 | in cluster with mir-17 to mir-20 |
| miR-18 | UAAGGUGCAUCUAGUGCAGAUA (SEQ ID NO: 84) | 13, AL138714 | in cluster with mir-17 to mir-20 |
| miR-19a | UGUGCAAAUCUAUGCAAAACUGA (SEQ ID NO: 85) | 13, AL138714 | in cluster with mir-17 to mir-20 |
| miR-19b | UGUGCAAAUCCAUGCAAAACUGA (SEQ ID NO: 86) | 13, AL138714, X, AC002407 | in cluster with mir-17 to mir-20 |
| miR-20 | UAAAGUGCUUAUAGUGCAGGUA (SEQ ID NO: 87) | 13, AL138714 | in cluster with mir-17 to mir-20 |
| miR-21 | UAGCUUAUCAGACUGAUGUUGA (SEQ ID NO: 88) | 17, AC004686, EST, BF326048 | homologs: mouse, EST, AA209594 |
| miR-22 | AAGCUGCCAGUUGAAGAACUGU (SEQ ID NO: 89) | ESTs, AW961681†, AA456477, AI752503, BF030303, HS1242049 | human ESTs highly similar; homologs: mouse, ESTs, e.g. AA823029; rat, ESTs, e.g. BF543690 |
| miR-23 | AUCACAUUGCCAGGGAUUUCC (SEQ ID NO: 90) | 19, AC020916 | homologs: mouse, EST, AW124037; rat, EST, BF402515 |
| miR-24 | UGGCUCAGUUCAGCAGGAACAG (SEQ ID NO: 91) | 9, AF043896, 19, AC020916 | homologs: mouse, ESTs, AA111466, AI286629; pig, EST, BE030976 |
| miR-25 | CAUUGCACUUGUCUCGGUCUGA (SEQ ID NO: 92) | 7, AC073842, EST, BE077684 | human chr 7 and EST identical; highly similar precursors in mouse ESTs (e.g. AI595464); fish precursor different STS: G46757 |
| miR-26a | UUCAAGUAAUCCAGGAUAGGCU (SEQ ID NO: 93) | 3, AP000497 | |
| miR-26b | UUCAAGUAAUUCAGGAUAGGUU (SEQ ID NO: 94) | 2, AC021016 | |
| miR-27 | UUCACAGUGGCUAAGUUCCGCU (SEQ ID NO: 95) | 19, AC20916 | U22C mutation in human genomic sequence |

TABLE 6-continued

Human miRNA sequences and genomic location.

| miRNA | sequence (5' to 3') | chr. or EST, acc. nb. | remarks* |
|---|---|---|---|
| miR-28 | AAGGAGCUCACAGUCUAUUGAG (SEQ ID NO: 96) | 3, AC063932 | |
| miR-29 | CUAGCACCAUCUGAAAUCGGUU (SEQ ID NO: 97) | 7, AF017104 | |
| miR-30 | CUUUCAGUCGGAUGUUUGCAGC (SEQ ID NO: 98) | 6, AL035467 | |
| miR-31 | GGCAAGAUGCUGGCAUAGCUG (SEQ ID NO: 99) | 9, AL353732 | |
| miR-32 | UAUUGCACAUUACUAAGUUGC (SEQ ID NO: 100) | 9, AL354797 | not detected by Northern blotting |
| miR-33 | GUGCAUUGUAGUUGCAUUG (SEQ ID NO: 101) | 22, Z99716 | not detected by Northern blotting |

*If several ESTs were retrieved for one organism in the database, only those with different precursor sequences are listed.
†precursor structure shown in FIG. 4.
From 220 short RNAs sequenced, 100 (45%) corresponded to miRNAs, 53 (24%) to already characterized functional RNAs (rRNA, snRNAs, tRNAs), and 67 (30%) sequences with no database entry.
For legend, see Table 1.

The invention claimed is:

1. An isolated nucleic acid molecule selected from the group consisting of: (a) a nucleotide sequence as shown in SEQ ID NO: 199 or SEQ ID NO: 393; (b) a nucleotide sequence which is the complement of (a); (c) a nucleotide sequence consisting of 18 to 25 nucleotides which has an identity of at least 80% to SEQ ID NO: 199 or the complement thereof; and (d) a nucleotide sequence consisting of 60-80 nucleotides which has an identity of at least 80% to SEQ ID NO: 393 or the complement thereof.

2. The nucleic acid molecule of claim 1, wherein the identity of sequence (c) is at least 90%.

3. The nucleic acid molecule of claim 1, wherein the identity of sequence (c) is at least 95%.

4. The nucleic acid molecule of claim 1 which is a miRNA precursor molecule having the nucleobase sequence as shown in SEQ ID NO: 393, or a DNA molecule coding therefor.

5. The nucleic acid molecule of claim 1, which is single-stranded.

6. The nucleic acid molecule of claim 1, which is at least partially double-stranded.

7. The nucleic acid molecule of claim 1, which is selected from RNA, DNA or nucleic acid analog molecules.

8. The nucleic acid molecule of claim 7, which is a molecule containing at least one modified nucleotide analog.

9. A composition comprising at least one nucleic acid molecule of claim 1 and a pharmaceutically acceptable carrier.

10. The composition of claim 9 wherein said pharmaceutically acceptable carrier is suitable for diagnostic applications.

11. The composition of claim 9 wherein said pharmaceutically acceptable carrier is suitable for therapeutic applications.

12. The composition of claim 9 as a marker or modulator of developmental disorders.

13. The composition of claim 9 as a marker or modulator of gene expression.

14. The nucleic acid molecule of claim 1, wherein the identity of sequence (c) is 100%.

15. The nucleic acid molecule of claim 8, wherein said modified nucleotide analog is a 2' modified nucleotide.

16. The nucleic acid molecule of claim 8, wherein said modified nucleotide analog is a backbone-modified nucleotide.

17. The nucleic acid molecule of claim 8, wherein said molecule has at least one locked nucleic acid.

18. The nucleic acid molecule of claim 1 having a length of 21, 22 or 23 nucleotides.

19. The composition of claim 12 wherein the developmental disorder is cancer.

20. A recombinant expression vector comprising at least one nucleic acid molecule of claim 1.

21. A hybridisation probe comprising the nucleic acid molecule of claim 1.

22. The isolated nucleic acid molecule according to claim 1, wherein said nucleotide sequence is selected from the group consisting of
   (a) a nucleotide sequence as shown SEQ ID NO: 199; and
   (b) a nucleotide sequence which is the complement of (a).

23. The isolated nucleic acid molecule according to claim 1, wherein said nucleotide sequence consists of both SEQ ID NO: 199 and the complement of SEQ ID NO: 199.

24. The isolated nucleic acid molecule according to claim 1, wherein said nucleotide sequence consists of SEQ ID NO: 199 hybridized to the complement of SEQ ID NO: 199.

* * * * *